(12) United States Patent
Dempah et al.

(10) Patent No.: US 11,655,237 B2
(45) Date of Patent: May 23, 2023

(54) SOLID FORMS OF A COT INHIBITOR COMPOUND

(71) Applicant: Gilead Sciences, Inc., Foster City, CA (US)

(72) Inventors: Kassibla E. Dempah, San Francisco, CA (US); Bing Shi, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 35 days.

(21) Appl. No.: 17/212,228

(22) Filed: Mar. 25, 2021

(65) Prior Publication Data

US 2021/0309637 A1    Oct. 7, 2021

Related U.S. Application Data

(60) Provisional application No. 63/001,810, filed on Mar. 30, 2020.

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC ............... C07D 401/14; C07B 2200/13; A61P 29/00; A61P 35/00
See application file for complete search history.

(56) References Cited

U.S. PATENT DOCUMENTS

| | | | |
|---|---|---|---|
| 3,845,770 A | 11/1974 | Theeuwes et al. |
| 3,930,837 A | 1/1976 | Serban |
| 4,151,298 A | 4/1979 | Drabek et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,565,408 A | 10/1996 | Hagen et al. |
| 5,616,345 A | 4/1997 | Geoghegan et al. |
| 7,297,795 B2 | 11/2007 | Sutherland et al. |
| 7,432,279 B2 | 10/2008 | Green et al. |
| 7,741,354 B2 | 6/2010 | Thormann et al. |
| 8,008,481 B2 | 8/2011 | Ericsson et al. |
| 9,173,395 B2 | 11/2015 | Frackenpohl et al. |
| 9,453,026 B2 | 9/2016 | Harriman et al. |
| 9,815,818 B2 | 11/2017 | Bacon et al. |
| 9,878,995 B2 | 1/2018 | Bacon et al. |
| 9,878,996 B2 | 1/2018 | Silverman |
| 10,059,695 B2 | 8/2018 | Balan et al. |
| 10,316,017 B2 | 6/2019 | Bacon et al. |
| 10,577,352 B2 | 3/2020 | Balan et al. |
| 10,702,503 B2 | 7/2020 | Haneda et al. |
| 10,947,259 B2 | 3/2021 | Canales et al. |
| 11,066,414 B2 | 7/2021 | Bacon et al. |
| 11,325,930 B2 | 5/2022 | Canales et al. |
| 2005/0043537 A1 | 2/2005 | Sutherland et al. |
| 2006/0264460 A1 | 11/2006 | Green et al. |
| 2011/0009410 A1 | 1/2011 | Corkey et al. |
| 2013/0116206 A1 | 5/2013 | Pisaneschi et al. |
| 2013/0123231 A1 | 5/2013 | Harriman et al. |
| 2013/0197037 A1 | 8/2013 | Notte |
| 2013/0225579 A1 | 8/2013 | Zhang et al. |
| 2014/0171422 A1 | 6/2014 | Otsubo et al. |
| 2014/0221659 A1 | 8/2014 | Kinzel et al. |
| 2014/0275006 A1 | 9/2014 | Yoshinaga et al. |
| 2015/0297573 A1 | 10/2015 | Dalle et al. |
| 2016/0244430 A1 | 8/2016 | Brown et al. |
| 2016/0280683 A1 | 9/2016 | Andres et al. |
| 2017/0008873 A1 | 1/2017 | Bacon et al. |
| 2017/0008905 A1 | 1/2017 | Bacon et al. |
| 2017/0152240 A1 | 6/2017 | Bacon et al. |
| 2017/0267690 A1 | 9/2017 | Alexander et al. |

(Continued)

FOREIGN PATENT DOCUMENTS

| CN | 103408572 A | 11/2013 |
|---|---|---|
| CN | 103483363 A | 1/2014 |

(Continued)

OTHER PUBLICATIONS

Bunz et al. (1988), "Bridgehead-Coupled Bicyclo[1.1.1]pentanes: Synthesis and Structure", Chem Ber, 121(10):1785-1790.

Cooksey et al. (1968), "N-Substituted Heterocyclic Cations. Part VIII. Substituent Effects and the Acidity of Quinolinium Ions. Hydroxide Addition versus Proton Loss", J Chem Soc (B), 1191-1197.

Della et al. (1996), "Experimental and Theoretical Study of Substituent Effects on $^3J(^{13}C1-^1H)$ Coupling Constants in 1-X-bicyclo[1.1.1]pentanes", J Phys Org Chem, 9(3):168-178.

Eller et al. (1922), "Über die Einwirkung von Sulfurylchlorid auf aromatische Amine", Berichte der Deutschen Chemischen Gesellschaft [Abteilung] B: Abhandlungen, 55B:217-224.

(Continued)

*Primary Examiner* — John M Mauro

(74) *Attorney, Agent, or Firm* — Fish & Richardson P.C.

(57) ABSTRACT

Disclosed are solid forms of a Cot (cancer Osaka thyroid) inhibitor and corresponding methods of preparation thereof, wherein the Cot inhibitor has the following formula:

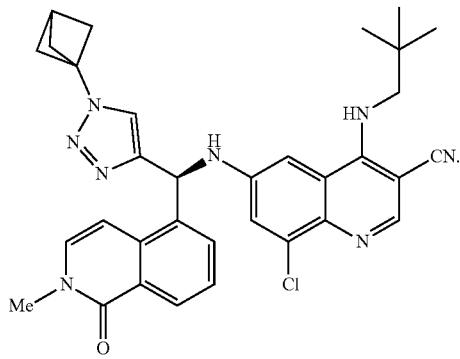

47 Claims, 32 Drawing Sheets

(56) References Cited

U.S. PATENT DOCUMENTS

| | | |
|---|---|---|
| 2017/0268069 A1 | 9/2017 | Garraway et al. |
| 2017/0273952 A1 | 9/2017 | Watkins |
| 2017/0362201 A1 | 12/2017 | Bacon et al. |
| 2018/0002316 A1 | 1/2018 | Balan et al. |
| 2018/0013320 A1 | 1/2018 | Brooks et al. |
| 2018/0021341 A1 | 1/2018 | Harriman et al. |
| 2018/0237455 A1 | 8/2018 | Bacon et al. |
| 2018/0280394 A1 | 10/2018 | Bates et al. |
| 2018/0298025 A1 | 10/2018 | Geier et al. |
| 2018/0333401 A1 | 11/2018 | Bates et al. |
| 2019/0016705 A1 | 1/2019 | Balan et al. |
| 2019/0031612 A1 | 1/2019 | Li et al. |
| 2019/0134041 A1 | 5/2019 | Bates et al. |
| 2019/0248807 A1 | 8/2019 | Bacon et al. |
| 2020/0123172 A1 | 4/2020 | Bacon et al. |
| 2020/0281911 A1 | 9/2020 | Dalton et al. |
| 2020/0392170 A1 | 12/2020 | Canales et al. |
| 2021/0061831 A1 | 3/2021 | Canales et al. |
| 2021/0147454 A1 | 5/2021 | Canales et al. |
| 2022/0235078 A1 | 7/2022 | Canales et al. |
| 2022/0259234 A1 | 8/2022 | Canales et al. |

FOREIGN PATENT DOCUMENTS

| | | |
|---|---|---|
| JP | H2036181 A | 2/1990 |
| WO | WO-94/27969 A1 | 12/1994 |
| WO | WO 1998/043960 | 10/1998 |
| WO | WO-99/11124 A1 | 3/1999 |
| WO | WO-00/02887 A2 | 1/2000 |
| WO | WO 2000/018740 | 4/2000 |
| WO | WO-2004/078176 A1 | 9/2004 |
| WO | WO-2005/019201 A2 | 3/2005 |
| WO | WO 2005/028443 | 3/2005 |
| WO | WO 2005/082891 | 9/2005 |
| WO | WO-2006/030032 A1 | 3/2006 |
| WO | WO-2006/124692 A2 | 11/2006 |
| WO | WO 2008/055950 | 5/2008 |
| WO | WO-2008/092292 A1 | 8/2008 |
| WO | WO-2010/055164 A2 | 5/2010 |
| WO | WO-2015/089170 A1 | 6/2015 |
| WO | WO-2015/134710 A1 | 9/2015 |
| WO | WO-2016/044331 A1 | 3/2016 |
| WO | WO 2017/007689 | 1/2017 |
| WO | WO 2017/007694 | 1/2017 |
| WO | WO 2018/005435 | 1/2018 |
| WO | WO 2020/185685 | 9/2020 |
| WO | WO 2020/252151 | 12/2020 |
| WO | WO 2021/030142 | 2/2021 |
| WO | WO 2021/202224 | 10/2021 |
| WO | WO-2021/202688 A1 | 10/2021 |

OTHER PUBLICATIONS

Garofalo et al. (2013), "Discovery of 4-alkylamino-7-aryl-3-cyanoquinoline LRRK2 kinase inhibitors", Bioorg Med Chem Lett, 23(7):1974-1977.

Gianatassio et al. (2016), "Strain-release amination", Science, 351(6270):241-246.

Goh et al. (2014), "A New Route to Bicyclo[1.1.1]pentan-1-amine from 1-Azido-3-iodobicyclo[1.1.1]pentane", Org Lett, 16(7):1884-1887.

Green et al. (2007), "Inhibitors of Tumor Progression Loci-2 (Tpl2) Kinase and Tumor Necrosis Factor α (TNF-α) Production: Selectivity and in Vivo Antiinflammatory Activity of Novel 8-Substituted-4-anilino-6-aminoquinoline-3-carbonitriles", J Med Chem, 50(19):4728-4745.

Grignard et al. (1928), "Sur le monomagnésien de l'acétylène", Académie Des Sciences, Sep. 24, 1928, 517-520.

Hanselmann et al. (2010), "Synthesis of an Antibacterial Compound Containing a 1,4-Substituted 1H-1,2,3-Triazole: A Scaleable Alternative to the "Click" Reaction", Org Process Res Dev, 14(1):152-158.

Hu et al. (2006), "Inhibition of Tpl2 kinase and TNFα production with quinoline-3-carbonitriles for the treatment of rheumatoid arthritis", Bioorg Med Chem Lett, 16(23):6067-6072.

Intl. Search Report—Written Opinion dated Jul. 5, 2021 for Intl. Appl. No. PCT/US2021/024067 (corresponding to U.S. Appl. No. 17/212,228).

Kitamura et al. (2011), "Synthesis of α,α-diarylacetamides from benzyl aryl ketones using 2-azido-1,3-dimethylimidazolinium hexafluorophosphate", Tetrahedron Lett, 52(24):3158-3161.

Kokhan et al. (2017), "Bicyclo[1.1.1]pentane-Derived Building Blocks for Click Chemistry", Eur J Org Chem, 2017(43):6450-6456.

Korner, G. (1913), "o-Halogenated p-nitroaniline and its derivatives", Atti della Accademia Nazionale dei Lincei, Classe di Scienze Fisiche, Matematiche e Naturali, Rendiconti, 22(I):823-836.

Kranenburg et al. (1998), "The Effect of the Bite Angle of Diphosphane Ligands on Activity and Selectivity in Palladium-Catalyzed Cross-Coupling", Eur J Inorg Chem, 1998(2):155-157.

Kötz et al. (1913), "Gleichzeitige Reduktion und Oxydation. (Erste Abhandlung.) Dichlorbrenztraubensäure, -nitril und-ester aus Trichlormilchsäure, -nitril und-ester", Journal Fuer Praktische Chemie-chemiker-zeitung, 88:531-552.

Lopchuk et al. (2017), "Strain-Release Heteroatom Functionalization: Development, Scope, and Stereospecificity", J Am Chem Soc, 139(8):3209-3226.

Mitter et al. (1925), "Condensation of Amidines with Ethoxymethylene Derivatives of β-Ketonic Esters, β-Diketones and Cyanacetic Ester. Part II", Quarterly Journal of the Indian Chemical Society, vol. II:61-70.

Newton et al. (1972), "Theoretical Studies of Tricyclo[1.1.1.$0^{1,3}$]pentane and Bicyclo[1.1.1]pentane", J Am Chem Soc, 94(3):773-778.

Osborn et al. (1956), "Studies of the Amino-isoquinolines, -cinnolines, and -quinazolines", J Chem Soc, 4191-4206.

Passalacqua, T. (1914), "Ethoxymethylenemalononitrile and its Derivatives", Gazzetta Chimica Italiana, 43(II):566-569.

Petyunin et al. (1957), "Chemistry of heterocycles. XXX. 2,4-Dihalo derivatives of 9-phenylacridine", Zhurnal Obshchei Khimii, 27:1558-1562.

Pisarenko et al. (2009), "Synthesis and hydroxylation of 1-alkyl- and 7-alkyl-1,3,7-triazapyrenium salts", Chem Heterocycl Compd, 45(5):580-586.

Qian et al. (2000), "Asymmetric glyoxylate-ene reaction catalyzed by $C_2$-symmetric chiral bis(oxazoline)-lanthanide complexes", Tetrahedron Asymmetry, 11(11):2347-2357.

Robak et al. (2010), "Synthesis and Applications of tert-Butanesulfinamide", Chem Rev, 110(6):3600-3740.

Saal et al. (2013), "Pharmaceutical salts: A summary on doses of salt formers from the Orange Book", Eur J Pharm Sci.; 49(4):614-623.

Sakai et al. (1986), "Reactions of α-Polyhalo Ketone Tosylhydrazones with Sulfide Ion and Primary Amines. Cyclization to 1,2,3-Thiadiazoles and 1,2,3-Triazoles", Bull Chem Soc Jpn, (59)1:179-183.

Semmler et al. (1985), "Tetracyclo[5.1.0.0$^{1,6}$.0$^{2,7}$]octane, a [1.1.1]Propellane Derivative, and a New Route to the Parent Hydrocarbon", J Am Chem Soc, 107(22):6410-6411.

Thirumoorthi et al. (2015), "Expedient synthesis of 3-phenylbicyclo[1.1.1]pentan-1-amine via metal-free homolytic aromatic alkylation of benzene", Chem Commun, 51:3139-3142.

Tomisawa et al. (1973), "Studies on 1-Alkyl-2(1H)-pyridone Derivatives. XVI. The Friedel-Crafts Reaction of 2-Methyl-1(2H)-isoquinolone", Chem Pharm Bull, 21(12):2585-2589.

Van Berkel et al. (2012), "Traceless Tosylhydrazone-Based Triazole Formation: A Metal-Free Alternative to Strain-Promoted Azide-Alkyne Cycloaddition", Angew Chem Int Ed, 51(22):5343-5346.

Walter et al. (1934), "The Reduction of Cyanides", J Am Chem Soc, 56(7):1614-1616.

Wang et al. (2009), "Cyanoacetamide Multicomponent Reaction (I): Parallel Synthesis Of Cyanoacetamides", J Comb Chem, 11(5):920-927.

Wiberg et al. (1970), "Bicyclo[1.1.1]pentane Derivatives", J Org Chem, 35(2):369-373.

(56) References Cited

OTHER PUBLICATIONS

Akriviadis et al., "Treatment of alcoholic hepatitis: is this a "dead-end"?," Ann Gastroenterol., 2016, 29(2):236-237.
Australian Office Action in Patent Application No. 2020257055, dated Mar. 30, 2021, 3 pages.
Brazilian Office Action in Patent Application No. BR102016015656-4, dated May 25, 2021, 4 pages.
Brown et al., "Bromination of Isoquinoline, Quinoline, Quinazoline and Quinoxaline in Strong Acid," Synthesis, 2002, 1:83-86.
Chemical Abstract Registry No. 1092351-39-7, dated Dec. 31, 2008, retrieved on Mar. 25, 2020.
Chemical Abstract Registry No. 1349435-18-2, indexed in the Registry File on STN CAS Online Dec. 6, 2011.
Chemical Abstract Registry No. 1415564-65-6, dated Dec. 27, 2012, retrieved on Mar. 25, 2020.
Chemical Abstracts, Database accession No. 292605-14-2.
Cohen et al., "Targeting protein kinases for the development of anti-inflammatory drugs", Curr Opin Cell Biol., 2009, 21:317-24.
Costa Rican Office Action in Patent Application No. 2017-0599, dated Apr. 13, 2021, 21 pages (with English translation).
Cusack et al., "Identification of a selective thieno[2,3-c]pyridine inhibitor of COT kinase and TNF-oc production" Bioorganic & Medicinal Chemistry Letters, 2009, 19:1722-25.
Detz et al., "Enantioselective Copper-Catalyzed Propargylic Amination," Angew. Chem. Int. Ed., 2008, 47:3777-3780.
Eisenberg et al., "Why can't we find a new treatment for SLE?", J Autoimmun, 2009, 32:223-30.
Exam Report dated Dec. 21, 2018 for New Zealand Appl. No. 738525, 1 page.
Exam Report dated Jul. 25, 2019 for Indian Appl. No. 201817004204, 6 pages (with English translation).
Exam Report dated Oct. 24, 2019 for Australian Appl. No. 2019203122, 6 pages.
Exam Report dated Jul. 12, 2021 for Indian Appl. No. 201817004204, 3 pages.
Exam Report in Pakastani Appln. No. 401/2016, dated Nov. 30, 2019, 2 pages.
Foster, "Deuterium Isotope Effects in Studies of Drug Metabolism," Trends Pharmacol. Sci., 1984, 5(12):524-527.
Gamage et al., "Structure-Activity Relationships for Pyrido-, Imidazo-, Pyrazolo-, Pyrazino-, and Pyrrolophenazinecarboxamides as Topoisomerase-Targeted Anticancer Agents", J Med Chem, 2002, 45(3):740-743.
Gantke et al., "Regulation and function of TPL-2, an IkB kinase-regulated MAP kinase kinase kinase", Cell Res., 2010, 21 (1):131-45.
Gavrin et al., "Inhibition of Tpl2 kinase and TNF-oc production with 1,7-naphthyridine-3-carbonitriles: Synthesis and structure-activity relationships" Bioorganic & Medicinal Chemistry Letters, 2005, 15:5288-5292.
GenBank Accession No. NP_004985, "matrix metalloproteinase-9 preproprotein [*Homo sapiens*]," Jul. 4, 2020, 3 pages.
George et al., "Cot/Tpl-2 Pratein Kinase as a Target for the Treatment of Inflammatory Disease", Current Topics in Medicinal Chemistry, 2009, 9:611-622.
George et al., "Discovery of thieno[2,3-c]pyridines as potent COT inhibitors" Bioorganic & Medicinal Chemistry Letters, 2008, 18:4952-4955.
Ghosh, "Anti-TNF therapy in Crohn's disease," Inflammatory Bowel Disease: Crossroads of Microbes, Epithelium and Immune Systems, Novartis Foundation Symposium, Nov. 2004, 263:193-205.
Gisbert et al., "Vedolizumab en el tratamiento de la enfermedad de Crohn," Gastroenterologia y Hepatologia, Jan. 2015, 38(5): 338-348 (with English abstract).
Glatthar et al., "Discovery of Imidazoquinolines as a Novel Class of Potent, Selective, and in Vivo Efficacious Cancer Osaka Thyroid (COT) Kinase Inhibitors", Journal of Medicinal Chemistry, 2016, 59:7544-7560.
Gonzalez-Cabrera et al., "SIP signaling: new therapies and opportunties," F1000Prime Reports, Dec. 2014, 6(109):1-7.

Goyal et al., "Models for anti-inflammatory activity of 8-substituted-4-anilino-6-aminoquinoline-3-carbonitriles", Med Chem Res, 2011, 21:1044-55.
Gu et al., "A highly specific inhibitor of matrix metalloproteinase-9 rescues laminin from proteolysis and neurons from apoptosis in transient focal cerebral ischemia," The Journal of Neuroscience, 2005, 25(27):6401-6408.
Gupta et al., "Homolytic displacement at carbon. Part 3. First example of alpha-attack on the allenyl- and prop-2-ynyl-cobaloximes," J. Chem. Soc., Perkin Trans. 2, 1988, 1377-1383.
Guyatt et al., "A new measure of health status for clinical trials in inflammatory bowel disease," Gastroenterology, 1989, 96:804-810.
Hall et al., "Pharmacologic Inhibition of Tpl2 Blocks Inflammatory Responses in Primary Human Monocytes, Synoviocytes, and Blood", The Journal of Biological Chemistry, 2007, 282(46): 33295-33304.
Hamad Elgazwy, "Studies of (Pd0-Mediated) Stille Cross-Coupling Reactions of Thiophenestannane with Aryl Halide Derivatives," Phosphorus, Sulfur, and Silicon and the Related Elements.; 164(1):131-143.
Hirata et al., "Inhibition of tumor progression locus 2 protein kinase decreases lipopolysaccharide-induced tumor necrosis factor alpha production due to the inhibition of the tip-associated protein induction in RAW264.7 cells", Biol Pharm Bull, 2010, 33(7):1233-7.
Hu et al., "Discovery of indazoles as inhibitors of Tpl2 kinase", Bioorganic & Medicinal Chemistry Letters, 2011, 21(16): 4758-4761.
IL Office Action in Israeli Appln. No. 274568, dated Jul. 12, 2020, 5 pages (with English translation).
International Search Report and Written Opinion in International Appln. No. PCT/US2016/040520, dated Aug. 16, 2018, 11 pages.
International Search Report and Written Opinion in International Appln. No. PCT/US2016/040552, dated Sep. 23, 2016, 9 pages.
International Search Report and Written Opinion in International Appln. No. PCT/US2017/039418, dated Sep. 20, 2017, 9 pages.
International Search Report and Written Opinion in International Appln. No. PCT/US2021/025118, dated Jul. 27, 2021, 15 pages.
International Search Report and Written Opinion in International Appln. No. PCT/US2020/037214, dated Aug. 25, 2020, 13 pages.
Kaila et al., "Identification of a novel class of selective Tpl2 kinase inhibitors: 4-Alkvlamino-fl, 7lnaohthvridine-3-carbonitriles", Bioorganic & Medicinal Chemistry, 2007, 15:6425-6442.
Kitamura et al., "A reagent for safe and efficient diazo-transfer to primary amines: 2-azido-1,3-dimethylimidazolinium hexafluorophosphate", Org. Biomol. Chem., 2014, 12:4397-4406.
Marshall et al., "Selective Allosteric Inhibition of MMP9 Is Efficacious in Preclinical Models of Ulcerative Colitis and Colorectal Cancer," PLoS One, May 2015, 10(5): pp. 1-26.
McMahon et al., "VEGF Receptor Signaling in Tumor Angiogenesis", The Oncologist, 2000, 5:3-10.
Nathubhai et al., "N3-alkylation during formation of quinazolin-4-ones from condensation of anthranilamides and orthoamides," Organic and Biomolecular Chemistry, 2011, 9(17):6089-6099.
Notice of Allowance dated Jun. 9, 2017 for U.S. Appl. No. 15/199,779, 11 pages.
Notice of Allowance dated Oct. 25, 2017 for U.S. Appl. No. 15/429,086, 10 pages.
Notice of Allowance dated Apr. 26, 2018 for U.S. Appl. No. 15/634,314, 5 pages.
Notice of Allowance dated Mar. 14, 2019 for U.S. Appl. No. 15/697,755, 12 pages.
Nunes et al., "Oral locally active steroids in inflammatory bowel disease," Journal of Crohn's and Colitis, Apr. 2013, 7(3): 183-191.
Office Action dated Mar. 23, 2017 for U.S. Appl. No. 15/429,086, 19 pages.
Office Action dated Jun. 30, 2017 for U.S. Appl. No. 15/429,086, 15 pages.
Office Action dated Sep. 7, 2017 for U.S. Appl. No. 15/199,534, 37 pages.
Office action dated Oct. 18, 2017 for Taiwan Appl. No. 105121281, 3 pages (with English translation).
Office Action dated Dec. 18, 2017 for U.S. Appl. No. 15/634,314, 10 pages.

(56) References Cited

OTHER PUBLICATIONS

Office Action dated Jul. 5, 2018 for U.S. Appl. No. 15/697,755, 54 pages.
Office Action dated Feb. 14, 2019 for Chilean Appl. No. 201703356, 23 pages (with English translation).
Office Action dated Apr. 25, 2019 for Panamanian Appl. No. 91923, 8 pages (with English translation).
Office Action dated Jun. 19, 2019 for U.S. Appl. No. 16/045,518, 12 pages.
Office Action dated Aug. 2, 2019 for Mexican Appl No. MX/a/2017/004737, 6 pages (with English translation).
Office Action dated Aug. 7, 2019 for Taiwanese Appl No. 107117905, 4 pages.
Office Action dated Aug. 22, 2019 for U.S. Appl. No. 16/391,673, 7 pages.
Office Action dated Aug. 26, 2019 for India Appl. No. 201817004197, 7 pages (with English translation).
Office Action dated Sep. 27, 2019 for European Appl. No. 16741446.5, 4 pages.
Office Action dated Oct. 4, 2019 for U.S. Appl. No. 15/891,163, 24 pages.
Office Action dated Mar. 12, 2020 for Ukrainian Appl. No. a201712984, 6 pages (with English translation).
Office Action in AR Appln. No. 20160102051, dated Jun. 1, 2020, 7pages (with English translation).
Office Action in ARIPO Appln. No. AP/P/2017/010402, dated Jun. 16, 2020, 5 pages.
Office Action in BR Appln. No. BR102016015656-4, dated Mar. 30, 2021, 4 pages (English Translation Only).
Office Action in CN Appln. No. 201910292757.5, dated Dec. 23, 2020, 15 pages (with English translation).
Office Action in CN Appln. No. 201910292757.5, dated Jul. 27, 2021, 12 pages (with English translation).
Office Action in CR Appln. No. 2017-0599, dated Oct. 28, 2020, 17 pages (with English translation).
Office Action in DO Appln,. No. P2017-0311, dated Jul. 7, 2021, 6 pages (with English Translation).
Office Action in DO Appln. No. 2017-0311, dated Aug. 24, 2020, 5 pages (with English translation).
Office Action in EP Appln. No. 18186568.4, dated May 5, 2020, 4 pages.
Office Action in GC Appln. No. 39905, dated Aug. 8, 2021, 4 pages.
Office Action in GC Appln. No. 2016-31644, dated May 6, 2020, 3 pages.
Office Action in JP Appln. No. 2018-171794, dated Jun. 23, 2020, 6 pages (with English translation).
Office Action in JP Appln. No. 2019-137759, dated Jun. 16, 2020, 4 pages (with English translation).
Office Action in MX Appln. No. MX/a/2020/000232, dated Mar. 25, 2021, 9 pages (with partial English translation).
Office Action in MX Appln. No. MX/a/2020/000232, dated Sep. 28, 2021, 20 pages (with English translation).
Office Action in MX Appln. No. MX_a_2020-000232, dated Oct. 8, 2020, 5 pages.
Office Action in PE Appln. No. 002804-2017/DIN, dated Jun. 30, 2021, 14 pages (with English translation).
Office Action in PH Appln. No. 1-2018-500031, dated Jun. 23, 2020, 4 pages.
Office Action in SA Appln. No. 517381350, dated Sep. 20, 2020, 7 pages (with English translation).
Office Action in Taiwanese Appl. No. 110111737, dated Jan. 22, 2022, 10 pages (with English translation).
Office Action in TW Appln No. 109119416, dated Aug. 11, 2021, 20 pages (with English translation).
Office Action dated Jan. 10, 2018 for Colombian Appl. No. NC2017/0013351, 6 pages.

PCT International Preliminary Report on Patentability in International Application No. PCT/US2016/040520, dated Jan. 9, 2019, 8 pages.
PCT International Preliminary Report on Patentability in International Application No. PCT/US2016/040552, dated Jan. 9, 2018, 7 pages.
PCT International Preliminary Report on Patentability in International Application No. PCT/US2017/039418, dated Jan. 1, 2019, 6 pages.
Perugorria et al., "Tumor progression locus 2/Cot is required for activation of extracellular regulated kinase in liver injury and toll-like receptor-induced TIMP-1 gene transcription in hepatic stellate cells in mice," Hepatology, 2013, 57:1238-1249.
Pinedo et al., "Translational Research: The Role of VEGF in Tumor Angiogenesis", The Oncologist, 2000,5:1-2.
Preliminary Rejection dated Jun. 17, 2019 for Korean Appl. No. 10-2018-7003220, 12 pages (with English translation).
PubChem Database (2006) 4-Chloro-3-cyano-7-ethoxy-6-nitroquinoline, CID11011305, 14 pages.
PubChem Database (2006) 4-Chloro-6-nitro-quinoline-3-carbonitrile, CID11085690, 20 pages.
PubChem Database (2006) 4-Chloro-7-methoxy-6-nitroquinoline-3-carbonitrile, CID11139975, 20 pages.
PubChem Database (2006) 4-Chloro-8-methoxy-6-nitro-quinoline-3-carbonitrile, CID11129151, 20 pages.
PubChem Database (2007) 4,8-Dichloro-6-nitroquinoline-3-carbonitrile, CID17759323, 20 pages.
PubChem Database (2007) 4-Chloro-8-methyl-6-nitro-3 quinolinecarbonitrile, CID22466621, 20 pages.
PubChem Database (2013) 4-Chloro-7-[3-(morpholin-4-yl)propoxy]-6-nitroquinoline-3-carbonitrile, CID71425067, 9 pages.
Restriction Requirement dated Feb. 16, 2017 for U.S. Appl. No. 15/199,534, 13 pages.
Restriction Requirement dated Mar. 8, 2017 for U.S. Appl. No. 15/199,779, 10 pages.
Restriction Requirement dated Aug. 11, 2017 for U.S. Appl. No. 15/634,314, 6 pages.
Restriction Requirement dated Mar. 26, 2018 for U.S. Appl. No. 15/697,755, 6 pages.
Restriction Requirement dated Jun. 29, 2018 for U.S. Appl. No. 15/891,163, 12 pages.
Restriction Requirement dated Feb. 8, 2019 for U.S. Appl. No. 16/045,518, 5 pages.
Search Report dated Feb. 5, 2019 for European Appl. No. 18186568.4, 5 pages.
Smith et al., "Vedolizumab: An α4β7 Integrin Inhibitor for Inflammatory Bowel Diseases", Annals of Pharmacotherapy, Sep. 2014, 7 pages.
Teli et al., "Pharmacophore generation and atom-based 3D-QSAR of novel quinoline-3-carbonitrile derivatives as Tpl2 kinase inhibitors", Journal of Enzyme Inhibition and Medicinal Chemistry, 2012, 27(4): 558-570.
Truelove et al., "Cortisone in ulcerative colitis: final report on a therapeutic trial," Br Med J., 1955, 2(4947):1041-1048.
Vyrla et al., "TPL2 Kinase Is a Crucial Signaling Factor and Mediator of NKT Effector Cytokine Expression in Immune-Mediated Liver Injury," The Journal of Immunology, 2016, 196(10):4298-310.
Wissner et al., "Syntheses and EGFR kinase inhibitory activity of 6-substituted-4-anilino [1,7] and [1,8] naphthyridine-3-carbonitriles", Bioorg. Med. Chem. Lett., 2004, 14(6):1411-6.
Wu et al., "Selective inhibitors of tumor progression loci-2 (Tpl2) kinase with potent inhibition of TNF-α production in human whole blood", Bioorganic & Medicinal Chemistry Letters, 2009, 19(13):3485-3488.
Zhu et al., "Anti-TNF-alpha therapies in systemic lupus erythematosus", J Biomed Biotechnol., 2010, 8 pages.

SOLID FORMS OF A COT INHIBITOR COMPOUND

CROSS-REFERENCES TO RELATED APPLICATIONS

This application claims the benefit of U.S. Provisional Application 63/001,810 filed on Mar. 30, 2020, the entirety of which is incorporated herein by reference.

FIELD

The present disclosure relates to solid forms of a Cot (cancer Osaka thyroid) inhibitor compound and methods of preparation of such forms.

BACKGROUND

Cot (cancer Osaka thyroid) protein is a serine/threonine kinase that is a member of the MAP kinase kinase kinase (MAP3K) family. It is also known as "Tpl2" (tumor progression locus), "MAP3K8" (mitogen-activated protein kinase kinase kinase 8) or "EST" (Ewing sarcoma transformant). Cot was identified by its oncogenic transforming activity in cells and has been shown to regulate oncogenic and inflammatory pathways.

Cot is known to be upstream in the MEK-ERK pathway and is essential for LPS induced tumor necrosis factor-α (TNF-α) production. Cot has been shown to be involved in both production and signaling of TNFα. TNFα is a pro-inflammatory cytokine and plays an important role in inflammatory diseases, such as rheumatoid arthritis (RA), multiple sclerosis (MS), inflammatory bowel disease (IBD), diabetes, sepsis, psoriasis, misregulated TNFα expression and graft rejection.

There remains a need to develop solid forms of Cot inhibitor compounds, including solid forms of Compound 1:

Compound 1

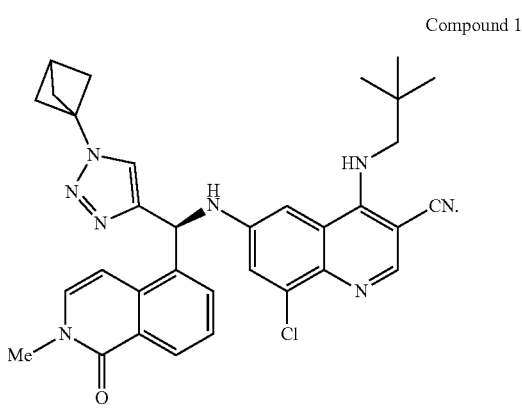 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

SUMMARY

Provided in one aspect is a solid form of Compound 1 (Freebase Form I). In some aspects, Freebase Form I is characterized by an XRPD pattern comprising peaks at 10.4, 13.0, and 18.1 degrees 2θ (±0.2 degrees 2θ), wherein the XRPD is made using Cu Kα radiation.

Provided in another aspect is a solid form of Compound 1 oxalate (Oxalate Form I). In some aspects, Oxalate Form I is characterized by an XRPD pattern comprising peaks at 5.2, 6.3, and 7.5 degrees 2θ (±0.2 degrees 2θ), wherein the XRPD is made using Cu Kα radiation.

Provided in another aspect is a solid form of Compound 1 maleate. In some aspects, Compound 1 maleate is characterized by an XRPD pattern comprising peaks at 8.2, 8.6, and 11.9 degrees 2θ (±0.2 degrees 2θ), wherein the XRPD is made using Cu Kα radiation.

Provided in another aspect is a solid form of Compound 1 camsylate (Camsylate Form I). In some aspects, Camsylate Form I is characterized by an XRPD pattern comprising peaks at 5.4, 12.0, and 17.5 degrees 2θ (±0.2 degrees 2θ), wherein the XRPD is made using Cu Kα radiation.

Provided in another aspect is a solid form of Compound 1 camsylate (Camsylate Form II). In some aspects, Camsylate Form II is characterized by an XRPD pattern comprising peaks at 2.8, 4.7, and 5.4 degrees 2θ (±0.2 degrees 2θ), wherein the XRPD is made using Cu Kα radiation.

Provided in another aspect is a solid form of Compound 1 camsylate (Camsylate Form III). In some aspects, Camsylate Form III is characterized by an XRPD pattern comprising peaks at 5.5, 8.9, and 18.5 degrees 2θ (±0.2 degrees 2θ), wherein the XRPD is made using Cu Kα radiation.

Provided in one aspect is a pharmaceutical composition comprising any one of the solid forms described herein and a pharmaceutically acceptable carrier.

Provided in one aspect is a method of treating a disease or condition mediated by cancer Osaka thyroid (Cot) in a human subject in need thereof, comprising administering to the subject an effective amount of any one of the compositions described herein.

Provided in some aspects are methods of preparing a solid form of Compound 1.

DETAILED DESCRIPTION

Figure 1:
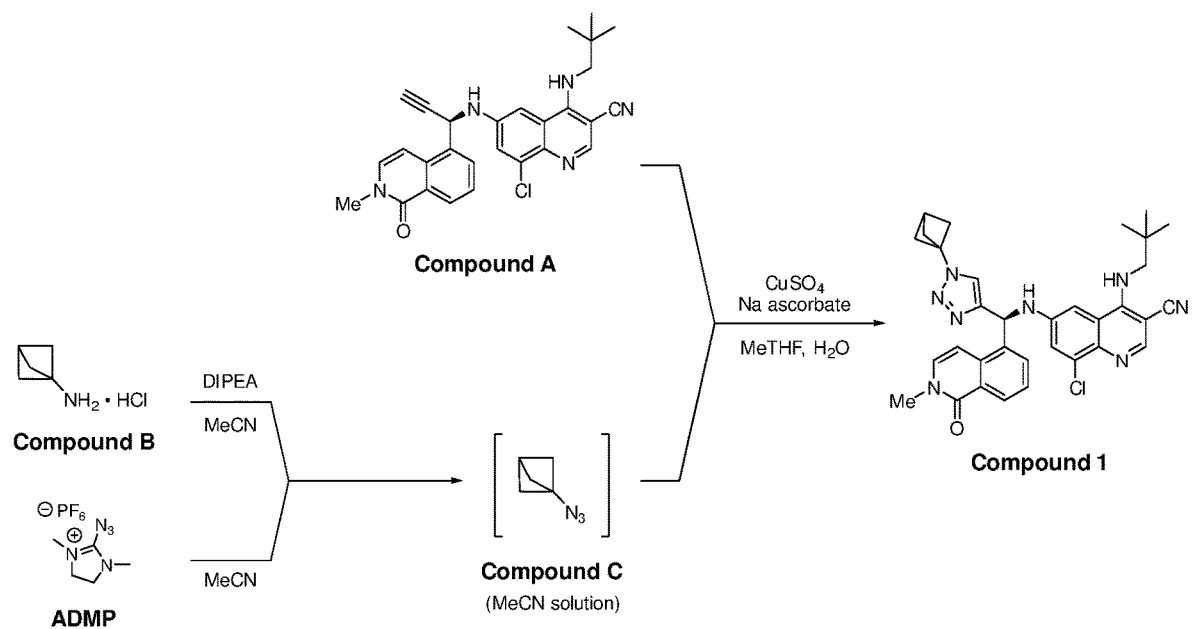
FIG. 1 shows a reaction scheme for the preparation of Compound 1 Freebase Form I.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Definitions

As used above and throughout the description, the following abbreviations, unless otherwise indicated, shall be understood to have the following meanings:

2-MeTHF 2-methyltetrahydrofuran
ADMP 2-azido-1,3-dimethylimidazolium hexafluorophosphate
DCM Dichloromethane
DSC Differential scanning calorimetry
Equiv Equivalents
EtOAc Ethyl acetate
HCl Hydrochloric acid
IPAc Isopropyl acetate
IPE Isopropyl ether
M Molar
MEK Methyl-ethylketone
MIBK Methyl-isobutylketone
MTBE Methyl-t-butyl ether
TGA Thermogravimetric analysis
THF Tetrahydrofuran
XRPD X-ray powder diffraction As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

"Hydrate" refers to a complex formed by the combining of a compound and water. The term includes stoichiometric as well as non-stoichiometric hydrates.

"Solvate" refers to a complex formed by the combining of a compound and a solvent.

As used herein, a "solvent" is a substance that can dissolve a solute to a solution. A solvent can be a polar solvent or a non-polar solvents. Non-limiting examples of solvents include, but are not limited to, water, alkanes such as heptanes, hexanes, and cyclohexane, petroleum ether, alcohols such as methanol, ethanol, propanol, isopropanol, ethylene glycol and polyethylene glycol such as PEG400, alkanoates such as ethyl acetate, propyl acetate, isopropyl acetate, and butyl acetate, acetonitrile, alkanones such as acetone, methyl ethyl ketone (MEK), methyl propyl ketone (MPK) and methyl iso-butyl ketone (MIBK), ethers such as diethyl ether, methyl-t-butyl ether, tetrahydrofuran, methyltetrahydrofuran, 1,2-dimethoxy ethane and 1,4-dioxane, aromatics such as benzene and toluene, halogenated solvents such as methylene chloride, chloroform and carbon tetrachloride, dimethylsulfoxide (DMSO), and dimethylformamide (DMF). Other examples, include but are not limited to, diglyme, cyclopentyl methyl ether, diphenyl ether, trifluorotoluene, xylenes, acetic acid, trifluoroacetic acid, propionic acid, diphenyl ether, dichloroethane, chlorobenzene, tert-butanol, acetonitrile, propionitrile, and butyronitrile.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

As used herein, a pharmaceutical composition comprises a compound described herein, and at least one pharmaceutically acceptable excipient and/or carrier. Examples of a pharmaceutically acceptable excipient, include but are not limited to, a binding agent a flavor agent, a lubricating agent, a disintegration agent, a delay agent, an organic solvent, a suspending agent, an isotonicity agent, a buffer, an emulsifier, stabilizer and a preservative.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Nomenclature

The structure of the compound (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile is as follows:

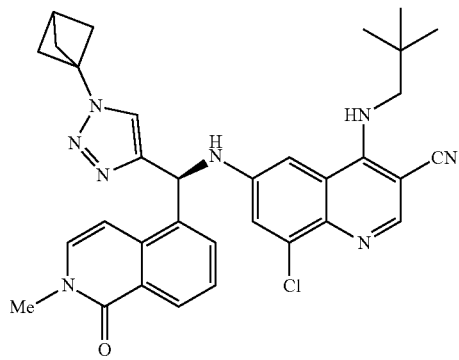 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

In this disclosure, the above compound is referred to as Compound 1.

Compound 1 Freebase Form I

In one aspect, a solid form of Compound 1 (Freebase Form I) is characterized by an XRPD pattern comprising peaks at 10.4, 13.0, and 18.1 degrees 2θ (±0.2 degrees 2θ), wherein the XRPD is made using Cu Kα radiation.

In some embodiments, the solid form of Compound 1 (Freebase Form I) characterized by an XRPD pattern further comprises one or more peaks at 18.8, 22.6, and 25.6 degrees 2θ (±0.2 degrees 2θ), wherein the XRPD is made using Cu Kα radiation. In some embodiments, the solid form of Compound 1 (Freebase Form I) characterized by an XRPD pattern further comprises one or more peaks at 19.2, 21.6, and 24.1 degrees 2θ (±0.2 degrees 2θ), wherein the XRPD is made using Cu Kα radiation.

In one aspect, a solid form of Compound 1 (Freebase Form I) is characterized by an XRPD pattern comprising peaks at 10.4, 13.0, 18.1, 18.8, 19.2, 21.6, 22.6, 24.1, or 25.6 degrees 2θ (±0.2 degrees 2θ), wherein the XRPD is made using Cu Kα radiation. In some embodiments, a solid form of Compound 1 (Freebase Form I) is characterized by an XRPD pattern as substantially shown in FIG. 2.

In some embodiments, a solid form of Compound 1 (Freebase Form I) is characterized by a DSC curve that comprises an endotherm followed by an exotherm at about 270° C. In some embodiments, a solid form of Compound 1 (Freebase Form I) is characterized by a DSC curve as substantially shown in FIG. 3. In some embodiments, a solid form of Compound 1 (Freebase Form I) is characterized by a TGA thermogram as substantially shown in FIG. 4.

Compound 1 Freebase Form III

In one aspect, a solid form of Compound 1 (Freebase Form III) is characterized by an XRPD pattern comprising peaks at 7.7, 11.3, and 18.8 degrees 2θ (±0.2 degrees 2θ), wherein the XRPD is made using Cu Kα radiation.

In some embodiments, the solid form of Compound 1 (Freebase Form III) characterized by an XRPD pattern further comprises one or more peaks at 15.6, 21.0, and 24.9 degrees 2θ (±0.2 degrees 2θ), wherein the XRPD is made using Cu Kα radiation. In some embodiments, the solid form of Compound 1 (Freebase Form III) characterized by an XRPD pattern further comprises one or more peaks at 16.7, 22.4, and 23.1 degrees 2θ (±0.2 degrees 2θ), wherein the XRPD is made using Cu Kα radiation.

In one aspect, a solid form of Compound 1 (Freebase Form I) is characterized by an XRPD pattern comprising peaks at 7.7, 11.3, 15.6, 16.7, 18.8, 21.0, 22.4, 23.1, and 24.9 degrees 2θ (±0.2 degrees 2θ), wherein the XRPD is made using Cu Kα radiation. In some embodiments, a solid form of Compound 1 (Freebase Form III) is characterized by an XRPD pattern as substantially shown in FIG. 5.

In some embodiments, a solid form of Compound 1 (Freebase Form III) is characterized by a DSC curve that comprises two endothermic events having onsets at about 68° C. and about 196° C. In some embodiments, a solid form of Compound 1 (Freebase Form III) is characterized by a DSC curve as substantially shown in FIG. 6. In some embodiments, a solid form of Compound 1 (Freebase Form III) is characterized by a TGA thermogram as substantially shown in FIG. 7.

Compound 1 HCl Material A

In one aspect, a solid form of Compound 1 HCl (HCl Material A) is characterized by an XRPD pattern comprising peaks at 7.3, 14.2, and 16.6 degrees 2θ (±0.2 degrees 2θ), wherein the XRPD is made using Cu Kα radiation.

In some embodiments, the solid form of Compound 1 HCl (HCl Material A) characterized by an XRPD pattern further comprises one or more peaks at 7.7, 8.6, and 17.1 degrees 2θ (±0.2 degrees 2θ), wherein the XRPD is made using Cu Kα radiation. In some embodiments, the solid form of Compound 1 HCl (HCl Material A) characterized by an XRPD pattern further comprises one or more peaks at 18.7, 20.1, and 21.6 degrees 2θ (±0.2 degrees 2θ), wherein the XRPD is made using Cu Kα radiation.

In one aspect, a solid form of Compound 1 HCl (HCl Material A) is characterized by an XRPD pattern comprising peaks at 7.3, 7.7, 8.6, 14.2, 16.6, 17.1, 18.7, 20.1, and 21.6 degrees 2θ (±0.2 degrees 2θ), wherein the XRPD is made using Cu Kα radiation. In some embodiments, a solid form of Compound 1 HCl (HCl Material A) is characterized by an XRPD pattern as substantially shown in FIG. 8.

In some embodiments, a solid form of Compound 1 HCl (HCl Material A) is characterized by a DSC curve that comprises two endothermic events having onsets at about 14° C. and about 180° C. In some embodiments, a solid form of Compound 1 HCl (HCl Material A) is characterized by a DSC curve as substantially shown in FIG. 9. In some embodiments, a solid form of Compound 1 HCl (HCl Material A) is characterized by a TGA thermogram as substantially shown in FIG. 10.

Compound 1 Methanesulfonate Material A

In one aspect, a solid form of Compound 1 methanesulfonate (Methanesulfonate Material A) is characterized by an XRPD pattern comprising peaks at 4.5, 6.1, and 11.6 degrees 2θ (±0.2 degrees 2θ), wherein the XRPD is made using Cu Kα radiation.

In some embodiments, the solid form of Compound 1 methanesulfonate (Methanesulfonate Material A) characterized by an XRPD pattern further comprises one or more peaks at 7.5, 20.7, and 24.5 degrees 2θ (±0.2 degrees 2θ), wherein the XRPD is made using Cu Kα radiation. In some embodiments, the solid form of Compound 1 methanesulfonate (Methanesulfonate Material A) characterized by an XRPD pattern further comprises one or more peaks at 19.6, 22.1, and 23.6 degrees 2θ (±0.2 degrees 2θ), wherein the XRPD is made using Cu Kα radiation.

In one aspect, a solid form of Compound 1 methanesulfonate (Methanesulfonate Material A) is characterized by an XRPD pattern comprising peaks at 4.5, 6.1, 7.5, 11.6, 19.6, 20.7, 22.1, 23.6, and 24.5 degrees 2θ (±0.2 degrees 2θ), wherein the XRPD is made using Cu Kα radiation. In some embodiments, a solid form of Compound 1 methanesulfonate (Methanesulfonate Material A) is characterized by an XRPD pattern as substantially shown in FIG. 11.

In some embodiments, a solid form of Compound 1 methanesulfonate (Methanesulfonate Material A) is characterized by a DSC curve that comprises three endothermic events with onsets at about 42° C., about 193° C., and about 234° C. In some embodiments, a solid form of Compound 1 methanesulfonate (Methanesulfonate Material A) is characterized by a DSC curve as substantially shown in FIG. 12. In some embodiments, a solid form of Compound 1 methanesulfonate (Methanesulfonate Material A) is characterized by a TGA thermogram as substantially shown in FIG. 13.

Compound 1 Methanesulfonate Material B

In one aspect, a solid form of Compound 1 methanesulfonate (Methanesulfonate Material B) is characterized by an XRPD pattern comprising peaks at 6.2, 7.6, and 23.1 degrees 2θ (±0.2 degrees 2θ), wherein the XRPD is made using Cu Kα radiation.

In some embodiments, the solid form of Compound 1 methanesulfonate (Methanesulfonate Material B) characterized by an XRPD pattern further comprises one or more peaks at 18.1, 18.6, and 26.6 degrees 2θ (±0.2 degrees 2θ), wherein the XRPD is made using Cu Kα radiation. In some embodiments, the solid form of Compound 1 methanesulfonate (Methanesulfonate Material B) characterized by an XRPD pattern further comprises one or more peaks at 19.7, 25.3, and 28.3 degrees 2θ (±0.2 degrees 2θ), wherein the XRPD is made using Cu Kα radiation.

In one aspect, a solid form of Compound 1 methanesulfonate (Methanesulfonate Material B) is characterized by an XRPD pattern comprising peaks at 6.2, 7.6, 18.1, 18.6, 19.7, 23.1, 25.3, 26.6, and 28.3 degrees 2θ (±0.2 degrees 2θ), wherein the XRPD is made using Cu Kα radiation. In some embodiments, a solid form of Compound 1 methanesulfonate (Methanesulfonate Material B) is characterized by an XRPD pattern as substantially shown in FIG. 14.

In some embodiments, a solid form of Compound 1 methanesulfonate (Methanesulfonate Material B) is characterized by a DSC curve that comprises an endotherm with an onset at about 19° C. In some embodiments, a solid form of Compound 1 methanesulfonate (Methanesulfonate Material B) is characterized by a DSC curve as substantially shown in FIG. 15. In some embodiments, a solid form of Compound 1 methanesulfonate (Methanesulfonate Material B) is characterized by a TGA thermogram as substantially shown in FIG. 16.

Compound 1 Methanesulfonate Material C

In one aspect, a solid form of Compound 1 methanesulfonate (Methanesulfonate Material C) is characterized by an XRPD pattern comprising peaks at 7.0, 7.5, and 19.6 degrees 2θ (±0.2 degrees 2θ), wherein the XRPD is made using Cu Kα radiation.

In some embodiments, the solid form of Compound 1 methanesulfonate (Methanesulfonate Material C) characterized by an XRPD pattern further comprises one or more peaks at 13.9, 21.2, and 24.2 degrees 2θ (±0.2 degrees 2θ), wherein the XRPD is made using Cu Kα radiation. In some embodiments, the solid form of Compound 1 methanesulfonate (Methanesulfonate Material C) characterized by an XRPD pattern further comprises one or more peaks at 20.7, 22.9, and 24.9 degrees 2θ (±0.2 degrees 2θ), wherein the XRPD is made using Cu Kα radiation.

In one aspect, a solid form of Compound 1 methanesulfonate (Methanesulfonate Material C) is characterized by an XRPD pattern comprising peaks at 7.0, 7.5, 13.9, 19.6, 20.7, 21.2, 22.9, 24.2, and 24.9 degrees 2θ (±0.2 degrees 2θ), wherein the XRPD is made using Cu Kα radiation. In some embodiments, a solid form of Compound 1 methanesulfonate (Methanesulfonate Material C) is characterized by an XRPD pattern as substantially shown in FIG. 17.

Figure 18:
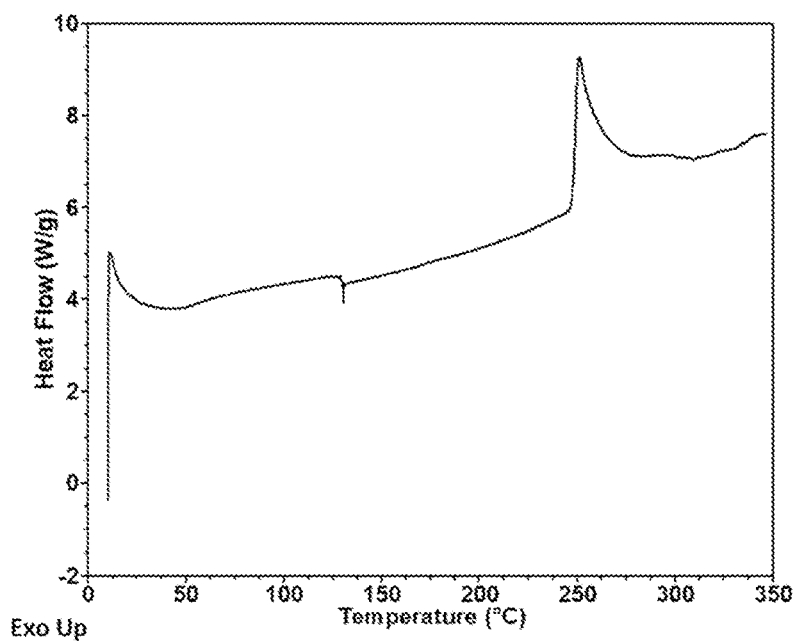
FIG. 18 shows the DSC thermogram of Compound 1 methanesulfonate Material C.

In some embodiments, a solid form of Compound 1 methanesulfonate (Methanesulfonate Material C) is characterized by a DSC curve as substantially shown in FIG. 18. In some embodiments, a solid form of Compound 1 methanesulfonate (Methanesulfonate Material C) is characterized by a TGA thermogram as substantially shown in FIG. 19.

Compound 1 Methanesulfonate Material D

In one aspect, a solid form of Compound 1 methanesulfonate (Methanesulfonate Material D) is characterized by an XRPD pattern comprising peaks at 5.5, 8.8, and 18.2 degrees 2θ (±0.2 degrees 2θ), wherein the XRPD is made using Cu Kα radiation.

In some embodiments, the solid form of Compound 1 methanesulfonate (Methanesulfonate Material D) characterized by an XRPD pattern further comprises one or more peaks at 8.4, 12.4, and 15.0 degrees 2θ (±0.2 degrees 2θ), wherein the XRPD is made using Cu Kα radiation. In some embodiments, the solid form of Compound 1 methanesulfonate (Methanesulfonate Material D) characterized by an XRPD pattern further comprises one or more peaks at 13.6, 21.4, and 26.6 degrees 2θ (±0.2 degrees 2θ), wherein the XRPD is made using Cu Kα radiation.

In one aspect, a solid form of Compound 1 methanesulfonate (Methanesulfonate Material D) is characterized by an XRPD pattern comprising peaks at 5.5, 8.4, 8.8, 12.4, 13.6, 15.0, 18.2, 21.4, and 26.6 degrees 2θ (±0.2 degrees 2θ), wherein the XRPD is made using Cu Kα radiation. In some embodiments, a solid form of Compound 1 methanesulfonate (Methanesulfonate Material D) is characterized by an XRPD pattern as substantially shown in FIG. 20.

Figure 21:
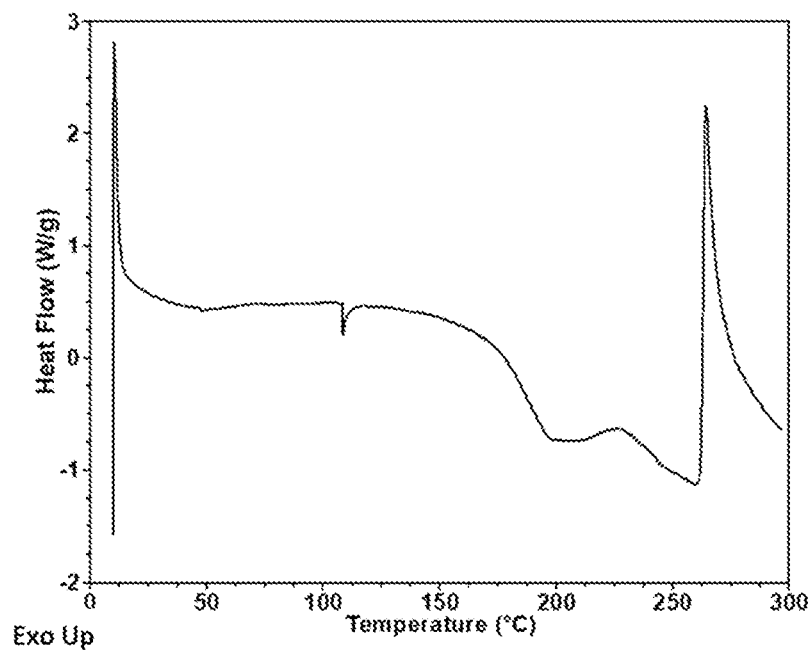
FIG. 21 shows the DSC thermogram of Compound 1 methanesulfonate Material D.

In some embodiments, a solid form of Compound 1 methanesulfonate (Methanesulfonate Material D) is characterized by a DSC curve as substantially shown in FIG. 21. In some embodiments, a solid form of Compound 1 methanesulfonate (Methanesulfonate Material C) is characterized by a TGA thermogram as substantially shown in FIG. 22.

Compound 1 Oxalate Material A

In one aspect, a solid form of Compound 1 oxalate (Oxalate Material A) is characterized by an XRPD pattern comprising peaks at 2.3, 4.0, and 6.3 degrees 2θ (±0.2 degrees 2θ), wherein the XRPD is made using Cu Kα radiation. In some embodiments, the solid form of Compound 1 oxalate (Oxalate Material A) characterized by an XRPD pattern further comprises one or more peaks at 13.4, 17.3, and 23.7 degrees 2θ (±0.2 degrees 2θ), wherein the XRPD is made using Cu Kα radiation. In some embodiments, the solid form of Compound 1 oxalate (Oxalate Material A) characterized by an XRPD pattern further comprises one or more peaks at 12.7, 21.8, and 22.4 degrees 2θ (±0.2 degrees 2θ), wherein the XRPD is made using Cu Kα radiation.

Figure 23:
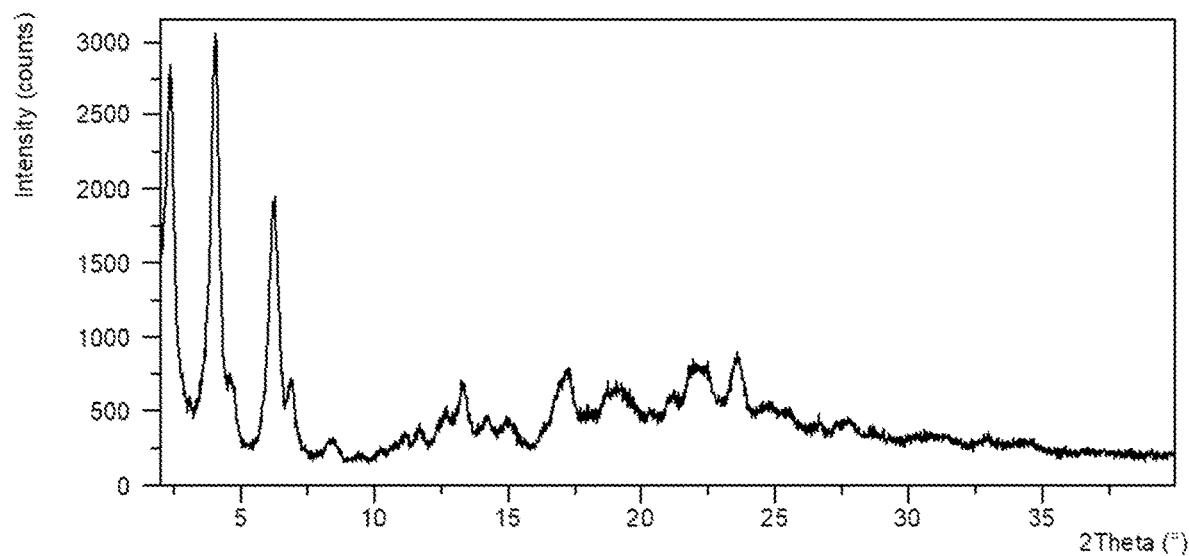
FIG. 23 shows the XRPD pattern of Compound 1 oxalate Material A.

In one aspect, a solid form of Compound 1 oxalate (Oxalate Material A) is characterized by an XRPD pattern comprising peaks at 2.3, 4.0, 6.3, 12.7, 13.4, 17.3, 21.8, 22.4, and 23.7 degrees 2θ (±0.2 degrees 2θ), wherein the XRPD is made using Cu Kα radiation. In some embodiments, the solid form of Compound 1 oxalate (Oxalate Material A) is characterized by an XRPD pattern as substantially shown in FIG. 23.

In some embodiments, the solid form of Compound 1 oxalate (Oxalate Material A) is characterized by a DSC curve that comprises two endotherms with onsets at about 165° C. and about 210° C. In some embodiments, the solid form of Compound 1 oxalate (Oxalate Material A) is characterized by a DSC curve as substantially shown in FIG. 24. In some embodiments, the solid form of Compound 1 oxalate (Oxalate Material A) is characterized by a TGA thermogram as substantially shown in FIG. 25.

Compound 1 Oxalate Form I

In one aspect, a solid form of Compound 1 oxalate (Oxalate Form I) is characterized by an XRPD pattern comprising peaks at 5.2, 6.3, and 7.5 degrees 2θ (±0.2 degrees 2θ), wherein the XRPD is made using Cu Kα radiation. In some embodiments, the solid form of Compound 1 oxalate (Oxalate Form I) characterized by an XRPD pattern further comprises one or more peaks at 10.3, 13.3, and 22.6 degrees 2θ (±0.2 degrees 2θ), wherein the XRPD is made using Cu Kα radiation. In some embodiments, the solid form of Compound 1 oxalate (Oxalate Form I) characterized by an XRPD pattern further comprises one or more peaks at 12.6, 16.4, and 17.9° 2 degrees 2θ (±0.2 degrees 2θ), wherein the XRPD is made using Cu Kα radiation.

In one aspect, a solid form of Compound 1 oxalate (Oxalate Form I) is characterized by an XRPD pattern comprising peaks at 5.2, 6.3, 7.5, 10.3, 12.6, 13.3, 16.4, 17.9, and 22.6 degrees 2θ (±0.2 degrees 2θ), wherein the XRPD is made using Cu Kα radiation. In some embodiments, the solid form of Compound 1 oxalate (Oxalate Form I) is characterized by an XRPD pattern as substantially shown in FIG. 26.

In some embodiments, the solid form of Compound 1 oxalate (Oxalate Form I) is characterized by a DSC curve that comprises an endotherm with an onset at about 220° C. In some embodiments, the solid form of Compound 1 oxalate (Oxalate Form I) is characterized by a DSC curve as substantially shown in FIG. 27. In some embodiments, the solid form of Compound 1 oxalate (Oxalate Form I) is characterized by a TGA thermogram as substantially shown in FIG. 28. In some embodiments, the solid form of Compound 1 oxalate (Oxalate Form I) is characterized by a TGA comprising a weight loss of about 14% at a temperature of about 200° C.

Compound 1 Oxalate Form II

In one aspect, a solid form of Compound 1 oxalate (Oxalate Form II) is characterized by an XRPD pattern comprising peaks at 7.8, 13.4, and 20.7 degrees 2θ (±0.2 degrees 2θ), wherein the XRPD is made using Cu Kα radiation. In some embodiments, the solid form of Compound 1 oxalate (Oxalate Form II) characterized by an XRPD pattern further comprises one or more peaks at 6.4, 17.5, and 24.5 degrees 2θ (±0.2 degrees 2θ), wherein the XRPD is made using Cu Kα radiation. In some embodiments, the solid form of Compound 1 oxalate (Oxalate Form II) characterized by an XRPD pattern further comprises additional peaks at 10.1, 23.6, and 30.6 degrees 2θ (±0.2 degrees 2θ), wherein the XRPD is made using Cu Kα radiation.

In one aspect, a solid form of Compound 1 oxalate (Oxalate Form II) is characterized by an XRPD pattern comprising peaks at 6.4, 7.8, 10.1, 13.4, 17.5, 20.7, 23.6, 24.5, and 30.6 degrees 2θ (±0.2 degrees 2θ), wherein the XRPD is made using Cu Kα radiation. In some embodiments, the solid form of Compound 1 oxalate (Oxalate Form II) is characterized by an XRPD pattern as substantially shown in FIG. 29.

In some embodiments, the solid form of Compound 1 oxalate (Oxalate Form II) is characterized by a DSC curve that comprises two endotherms with onsets at about 163° C. and about 214° C. In some embodiments, the solid form of Compound 1 oxalate (Oxalate Form II) is characterized by a DSC curve as substantially shown in FIG. 30. In some embodiments, the solid form of Compound 1 oxalate (Oxalate Form II) is characterized by a TGA comprising weight losses of about 3%, about 3%, and about 16%. In some embodiments, the solid form of Compound 1 oxalate (Oxalate Form II) is characterized by a TGA thermogram as substantially shown in FIG. 31.

Compound 1 Ethanedisulfonate

In one aspect, a solid form of Compound 1 ethanedisulfonate is characterized by an XRPD pattern comprising peaks at 5.5, 10.7, and 20.1 degrees 2θ (±0.2 degrees 2θ), wherein the XRPD is made using Cu Kα radiation. In some embodiments, the solid form of Compound 1 ethanedisulfonate characterized by an XRPD pattern further comprises one or more peaks at 8.3, 10.4, and 16.8 degrees 2θ (±0.2 degrees 2θ), wherein the XRPD is made using Cu Kα radiation. In some embodiments, the solid form of Compound 1 ethanedisulfonate characterized by an XRPD pattern further comprises one or more peaks at 18.0, 19.8, and 23.4 degrees 2θ (±0.2 degrees 2θ), wherein the XRPD is made using Cu Kα radiation.

In one aspect, a solid form of Compound 1 ethanedisulfonate is characterized by an XRPD pattern comprising peaks at 5.5, 8.3, 10.4, 10.7, 16.8, 18.0, 19.8, 20.1, and 23.4 degrees 2θ (±0.2 degrees 2θ), wherein the XRPD is made using Cu Kα radiation. In some embodiments, the solid form of Compound 1 ethanedisulfonate is characterized by an XRPD pattern as substantially shown in FIG. 32.

In some embodiments, the solid form of Compound 1 ethanedisulfonate is characterized by a DSC curve that comprises an endotherm with onset at about 31° C. In some embodiments, the solid form of Compound 1 ethanedisulfonate is characterized by a DSC curve as substantially shown in FIG. 33. In some embodiments, the solid form of Compound 1 ethanedisulfonate is characterized by a TGA thermogram as substantially shown in FIG. 34.

Compound 1 Maleate

In one aspect, a solid form of Compound 1 maleate is characterized by an XRPD pattern comprising peaks at 8.2, 8.6, and 11.9 degrees 2θ (±0.2 degrees 2θ), wherein the XRPD is made using Cu Kα radiation. In some embodiments, the solid form of Compound 1 maleate characterized by an XRPD pattern further comprises one or more peaks at 9.6, 17.3, and 19.1 degrees 2θ (±0.2 degrees 2θ), wherein the XRPD is made using Cu Kα radiation. In some embodiments, the solid form of Compound 1 maleate characterized by an XRPD pattern further comprises one or more peaks at 15.1, 21.1, and 23.5 degrees 2θ (±0.2 degrees 2θ), wherein the XRPD is made using Cu Kα radiation.

In one aspect, a solid form of Compound 1 maleate is characterized by an XRPD pattern comprising peaks at 8.2, 8.6, 9.6, 11.9, 15.1, 17.3, 19.1 21.1, and 23.5 degrees 2θ (±0.2 degrees 2θ), wherein the XRPD is made using Cu Kα radiation. In some embodiments, the solid form of Compound 1 maleate is characterized by an XRPD pattern as substantially shown in FIG. 35.

In some embodiments, the solid form of Compound 1 maleate is characterized by a DSC curve that comprises an endotherm with onset at about 130° C. and an exotherm with onset at about 160° C. In some embodiments, the solid form of Compound 1 maleate is characterized by a DSC curve as substantially shown in FIG. 36. In some embodiments, the solid form of Compound 1 maleate is characterized by a TGA comprising weight losses of about 5.6% and about 13.8%. In some embodiments, the solid form of Compound 1 maleate is characterized by a TGA thermogram as substantially shown in FIG. 37.

Compound 1 Camsylate (Camsylate Form I)

In one aspect, a solid form of Compound 1 camsylate (Camsylate Form I) is characterized by an XRPD pattern comprising peaks at 5.4, 12.0, and 17.5 degrees 2θ (±0.2 degrees 2θ), wherein the XRPD is made using Cu Kα radiation. In some embodiments, the solid form of Compound 1 camsylate (Camsylate Form I) characterized by an XRPD pattern further comprises one or more peaks at 10.1, 19.5, 22.4 degrees 2θ (±0.2 degrees 2θ), wherein the XRPD is made using Cu Kα radiation. In some embodiments, the solid form of Compound 1 camsylate (Camsylate Form I) characterized by an XRPD pattern further comprises one or more peaks at 6.7, 8.3, and 20.5 degrees 2θ (±0.2 degrees 2θ), wherein the XRPD is made using Cu Kα radiation.

In one aspect, a solid form of Compound 1 camsylate (Camsylate Form I) is characterized by an XRPD pattern comprising peaks at 5.4, 6.7, 8.3, 10.1, 12.0, 17.5, 19.5, 20.5, and 22.4 degrees 2θ (±0.2 degrees 2θ), wherein the XRPD is made using Cu Kα radiation. In some embodiments, the solid form of Compound 1 camsylate (Camsylate Form I) is characterized by an XRPD pattern as substantially shown in FIG. 38.

In some embodiments, a solid form of Compound 1 camsylate (Camsylate Form I) is characterized by a DSC curve that comprises a broad endotherm between ambient temperature to about 120° C. followed by a melting onset at about 196° C. In some embodiments, a solid form of Compound 1 camsylate (Camsylate Form I) is characterized by a DSC curve as substantially shown in FIG. 39. In some embodiments, a solid form of Compound 1 camsylate (Camsylate Form I) is characterized by a TGA comprising a weight loss of about 2% below a temperature of about 100° C. In some embodiments, a solid form of Compound 1 camsylate (Camsylate Form I) is characterized by a TGA thermogram as substantially shown in FIG. 40.

Compound 1 Camsylate (Camsylate Form II)

In one aspect, a solid form of Compound 1 camsylate (Camsylate Form II) is characterized by an XRPD pattern comprising peaks at 2.8, 4.7, and 5.4 degrees 2θ (±0.2 degrees 2θ), wherein the XRPD is made using Cu Kα radiation. In some embodiments, the solid form of Compound 1 camsylate (Camsylate Form II) characterized by an XRPD pattern further comprises one or more additional peaks at 7.2, 8.1, and 10.8 degrees 2θ (±0.2 degrees 2θ), wherein the XRPD is made using Cu Kα radiation. In some embodiments, the solid form of Compound 1 camsylate (Camsylate Form II) characterized by an XRPD pattern further comprises one or more peaks at 9.8, 12.4, and 17.7 degrees 2θ (±0.2 degrees 2θ), wherein the XRPD is made using Cu Kα radiation.

In one aspect, a solid form of Compound 1 camsylate (Camsylate Form II) is characterized by an XRPD pattern comprising peaks at 2.8, 4.7, 5.4, 7.2, 8.1, 9.8, 10.8, 12.4, and 17.7 degrees 2θ (±0.2 degrees 2θ), wherein the XRPD is made using Cu Kα radiation. In some embodiments, the solid form of Compound 1 camsylate (Camsylate Form II) is characterized by an XRPD pattern as substantially shown in FIG. 41.

In some embodiments, the solid form of Compound 1 camsylate (Camsylate Form II) is characterized by a DSC curve that comprises a broad endotherm between ambient temperature to about 120° C. followed by several endotherms at about 130° C., 198° C., and 214° C., respectively. In some embodiments, the solid form of Compound 1 camsylate (Camsylate Form II) is characterized by a DSC curve as substantially shown in FIG. 42. In some embodiments, the solid form of Compound 1 camsylate (Camsylate Form II) is characterized by a TGA comprising weight losses of about 3% at a temperature below about 100° C. and of about 2.4% at a temperature of about 198° C. In some embodiments, the solid form of Compound 1 camsylate (Camsylate Form II) is characterized by a TGA thermogram as substantially shown in FIG. 43.

Compound 1 Camsylate (Camsylate Form III)

In one aspect, a solid form of Compound 1 camsylate (Camsylate Form III) is characterized by an XRPD pattern comprising peaks at 5.5, 8.9, and 18.5 degrees 2θ (±0.2 degrees 2θ), wherein the XRPD is made using Cu Kα radiation. In some embodiments, the solid form of Compound 1 camsylate (Camsylate Form III) characterized by an XRPD pattern further comprises one or more peaks at 4.5, 10.9, and 16.6 degrees 2θ (±0.2 degrees 2θ), wherein the XRPD is made using Cu Kα radiation. In some embodiments, the solid form of Compound 1 camsylate (Camsylate Form III) characterized by an XRPD pattern further comprises one or more peaks at 12.2, 21.5, and 21.8 degrees 2θ (±0.2 degrees 2θ), wherein the XRPD is made using Cu Kα radiation.

In one aspect, the solid form of Compound 1 camsylate (Camsylate Form III) is characterized by an XRPD pattern comprising peaks at 4.5, 5.5, 8.9, 10.9, 12.2, 16.6, 18.5, 21.5, and 21.8 degrees 2θ (±0.2 degrees 2θ), wherein the XRPD is made using Cu Kα radiation. In some embodiments, the solid form of Compound 1 camsylate (Camsylate Form III) is characterized by an XRPD pattern as substantially shown in FIG. 44.

In some embodiments, the solid form of Compound 1 camsylate (Camsylate Form III) is characterized by a DSC curve that comprises a broad endotherm between ambient temperature to about 100° C. followed by a melting endotherm with an onset at about 207° C. In some embodiments, the solid form of Compound 1 camsylate (Camsylate Form III) is characterized by a DSC curve as substantially shown in FIG. 45. In some embodiments, the solid form of Compound 1 camsylate (Camsylate Form III) is characterized by a TGA comprising a weight loss of about 2% at a temperature below about 50° C. In some embodiments, the solid form of Compound 1 camsylate (Camsylate Form III) is characterized by a TGA thermogram as substantially shown in FIG. 46.

Compound 1 Besylate (Besylate Hydrate A)

In one aspect, a solid form of Compound 1 besylate (Besylate Hydrate A) is characterized by an XRPD pattern comprising peaks at 7.7, 9.2, and 12.5 degrees 2θ (±0.2 degrees 2θ), wherein the XRPD is made using Cu Kα radiation. In some embodiments, the solid form of Compound 1 besylate (Besylate Hydrate A) characterized by an XRPD pattern further comprises one or more additional peaks at 9.6, 19.5, and 20.3 degrees 2θ (±0.2 degrees 2θ), wherein the XRPD is made using Cu Kα radiation. In some embodiments, the solid form of Compound 1 besylate (Besylate Hydrate A) characterized by an XRPD pattern further comprises one or more peaks at 15.3, 23.2, and 26.9 degrees 2θ (±0.2 degrees 2θ), wherein the XRPD is made using Cu Kα radiation.

In one aspect, a solid form of Compound 1 besylate (Besylate Hydrate A) is characterized by an XRPD pattern comprising peaks at 7.7, 9.2, 9.6, 12.5, 15.3, 19.5, 20.3, 23.2, and 26.9 degrees 2θ (±0.2 degrees 2θ), wherein the XRPD is made using Cu Kα radiation. In some embodiments, the solid form of Compound 1 besylate (Besylate Hydrate A) is characterized by an XRPD pattern as substantially shown in FIG. 47.

Compound 1 Besylate (Besylate Material A)

In one aspect, a solid form of Compound 1 besylate (Besylate Material A) is characterized by an XRPD pattern comprising peaks at 7.6, 8.8, and 14.8 degrees 2θ (±0.2 degrees 2θ), wherein the XRPD is made using Cu Kα radiation. In some embodiments, the solid form of Compound 1 besylate (Besylate Material A) characterized by an XRPD pattern further comprises one or more peaks at 9.6, 12.4, and 19.3 degrees 2θ (±0.2 degrees 2θ), wherein the XRPD is made using Cu Kα radiation. In some embodiments, the solid form of Compound 1 besylate (Besylate Material A) characterized by an XRPD pattern further comprises one or more peaks at 17.3, 24.9, and 26.5 degrees 2θ (±0.2 degrees 2θ), wherein the XRPD is made using Cu Kα radiation.

In one aspect, a solid form of Compound 1 besylate (Besylate Material A) is characterized by an XRPD pattern comprising peaks at 7.6, 8.8, 9.6, 12.4, 14.8, 17.3, 19.3, 24.9, and 26.5 degrees 2θ (±0.2 degrees 2θ), wherein the XRPD is made using Cu Kα radiation. In some embodiments, the solid form of Compound 1 besylate (Besylate Material A) is characterized by an XRPD pattern as substantially shown in FIG. 48.

In some embodiments, a solid form of Compound 1 besylate (Besylate Material A) is characterized by a DSC curve that comprises two endothermic events with onsets at about 66° C. and about 217° C. In some embodiments, a solid form of Compound 1 besylate (Besylate Material A) is characterized by a DSC curve as substantially shown in FIG. 49. In some embodiments, a solid form of Compound 1 besylate (Besylate Material A) is characterized by a TGA thermogram as substantially shown in FIG. 50.

Compound 1 Besylate Ethanol Solvate (Besylate Ethanol Solvate)

In one aspect, a solid form of Compound besylate ethanol solvate (Besylate ethanol solvate) is characterized by an XRPD pattern comprising peaks at 7.3, 9.1, and 14.8 degrees 2θ (±0.2 degrees 2θ), wherein the XRPD is made using Cu Kα radiation. In some embodiments, the solid form of Compound 1 besylate ethanol solvate (Besylate ethanol solvate) characterized by an XRPD pattern further comprises one or more peaks at 10.0, 18.1, 20.0 degrees 2θ (±0.2 degrees 2θ), wherein the XRPD is made using Cu Kα radiation. In some embodiments, the solid form of Compound 1 besylate ethanol solvate (Besylate ethanol solvate) characterized by an XRPD pattern further comprises one or more peaks at 13.5, 19.6, and 24.2 degrees 2θ (±0.2 degrees 2θ), wherein the XRPD is made using Cu Kα radiation.

In one aspect, a solid form of Compound 1 ethanol solvate (Besylate ethanol solvate) is characterized by an XRPD pattern comprising peaks at 7.3, 9.1, 10.0, 13.5, 14.8, 18.1, 19.6, 20.0, and 24.4 degrees 2θ (±0.2 degrees 2θ), wherein the XRPD is made using Cu Kα radiation.

Figure 51:
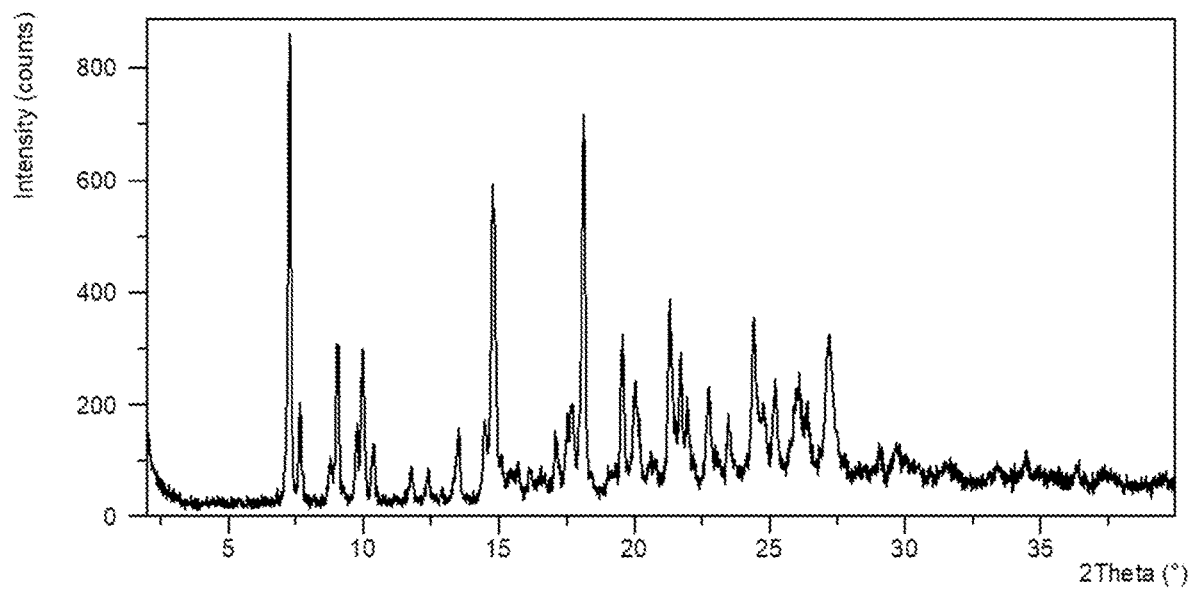
FIG. 51 shows the XRPD pattern of Compound 1 besylate ethanol solvate A.

In some embodiments, the solid form of Compound 1 besylate (Besylate Form I) is characterized by an XRPD pattern as substantially shown in FIG. 51.

Compound 1 Besylate (Besylate Form I)

In one aspect, a solid form of Compound 1 besylate (Besylate Form I) is characterized by an XRPD pattern comprising peaks at 6.8, 9.9, and 14.5 degrees 2θ (±0.2 degrees 2θ), wherein the XRPD is made using Cu Kα radiation. In some embodiments, the solid form of Compound 1 besylate (Besylate Form I) characterized by an XRPD pattern further comprises one or more peaks at 8.3, 15.5, and 17.8 degrees 2θ (±0.2 degrees 2θ), wherein the XRPD is made using Cu Kα radiation. In some embodiments, the solid form of Compound 1 besylate (Besylate Form I) characterized by an XRPD pattern further comprises one or more peaks at 16.2, 24.6, and 27.2 degrees 2θ (±0.2 degrees 2θ), wherein the XRPD is made using Cu Kα radiation.

Figure 52:
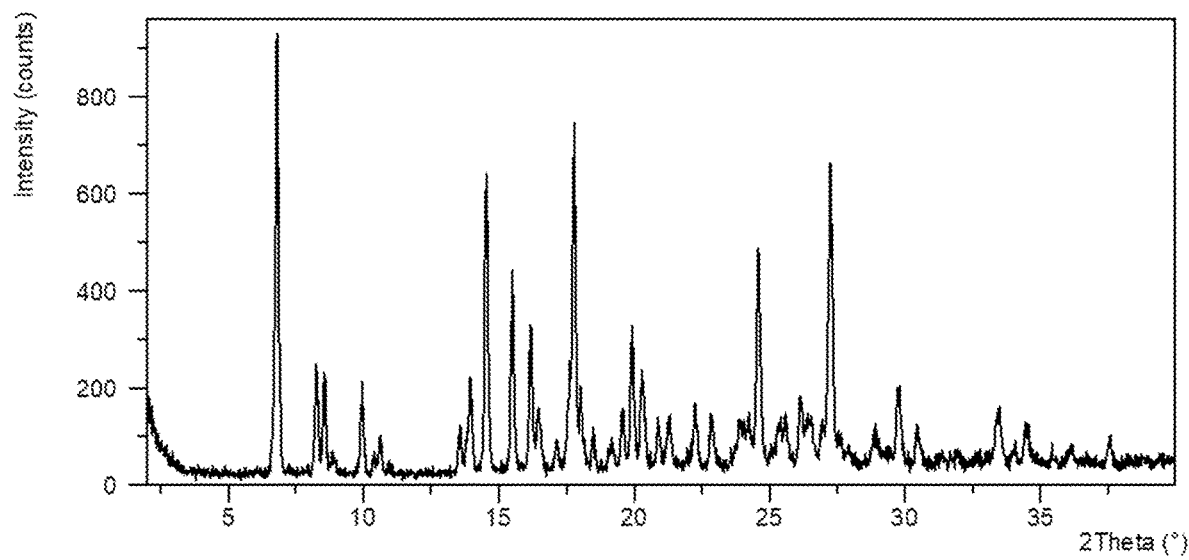
FIG. 52 shows the XRPD pattern of Compound 1 besylate Form I.

In one aspect, a solid form of Compound 1 besylate (Besylate Form I) is characterized by an XRPD pattern comprising peaks at 6.8, 8.3, 9.9, 14.5, 15.5, 16.2, 17.8, 24.6, and 27.2 degrees 2θ (±0.2 degrees 2θ), wherein the XRPD is made using Cu Kα radiation. In some embodiments, the solid form of Compound 1 besylate (Besylate Form I) is characterized by an XRPD pattern as substantially shown in FIG. 52.

In some embodiments, the solid form of Compound 1 besylate (Besylate Form I) is characterized by a DSC curve that comprises an endotherm with an onset at about 230° C. In some embodiments, the solid form of Compound 1 besylate (Besylate Form I) is characterized by a DSC curve as substantially shown in FIG. 53. In some embodiments, the solid form of Compound 1 besylate (Besylate Form I) is characterized by a TGA thermogram as substantially shown in FIG. 54.

Compound 1 Besylate (Besylate Form II)

In one aspect, a solid form of Compound 1 besylate (Besylate Form II) is characterized by an XRPD pattern comprising peaks at 6.1, 7.8, and 15.1 degrees 2θ (±0.2 degrees 2θ), wherein the XRPD is made using Cu Kα radiation. In some embodiments, the solid form of Compound 1 besylate (Besylate Form II) characterized by an XRPD pattern further comprises one or more peaks at 9.6, 16.1, and 21.3 degrees 2θ (±0.2 degrees 2θ), wherein the XRPD is made using Cu Kα radiation. In some embodiments, the solid form of Compound 1 besylate (Besylate Form II) characterized by an XRPD pattern further comprises one or more peaks at 18.7, 19.6, and 23.7 degrees 2θ (±0.2 degrees 2θ), wherein the XRPD is made using Cu Kα radiation.

In one aspect, a solid form of Compound 1 besylate (Besylate Form II) is characterized by an XRPD pattern comprising peaks at 6.1, 7.8, 9.6, 15.1, 16.1, 18.7, 19.6, 21.3, and 23.7 degrees 2θ (±0.2 degrees 2θ), wherein the XRPD is made using Cu Kα radiation. In some embodiments, the solid form of Compound 1 besylate (Besylate Form II) is characterized by an XRPD pattern as substantially shown in FIG. 55.

In some embodiments, the solid form of Compound 1 besylate (Besylate Form II) is characterized by a DSC curve that comprises an endotherm with an onset at about 229° C. In some embodiments, the solid form of Compound 1 besylate (Besylate Form II) is characterized by a DSC curve as substantially shown in FIG. 56. In some embodiments, the solid form of Compound 1 besylate (Besylate Form II) is characterized by a TGA thermogram as substantially shown in FIG. 57.

Compound 1 Esylate (Esylate Material A)

In one aspect, a solid form of Compound 1 esylate (Esylate Material A) is characterized by an XRPD pattern comprising peaks at 5.7, 9.4, and 10.3 degrees 2θ (±0.2 degrees 2θ), wherein the XRPD is made using Cu Kα radiation. In some embodiments, the solid form of Compound 1 esylate (Esylate Material A) characterized by an XRPD pattern further comprises one or more peaks at 8.9, 11.5, and 13.8 degrees 2θ (±0.2 degrees 2θ), wherein the XRPD is made using Cu Kα radiation. In some embodiments, the solid form of Compound 1 esylate (Esylate Material A) characterized by an XRPD pattern further comprises one or more peaks at 18.4, 24.9, and 31.1 degrees 2θ (±0.2 degrees 2θ), wherein the XRPD is made using Cu Kα radiation.

Figure 58:
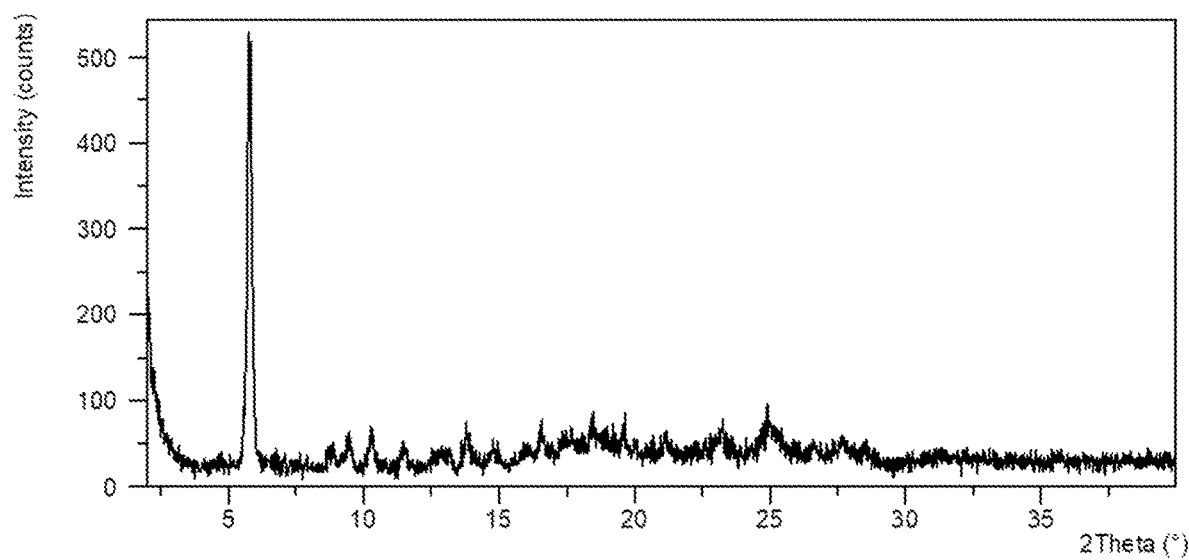
FIG. 58 shows the XRPD pattern of Compound 1 esylate Material A.

In one aspect, a solid form of Compound 1 esylate (Esylate Material A) is characterized by an XRPD pattern comprising peaks at 5.7, 8.9, 9.4, 10.3, 11.5, 13.8, 18.4, 24.9, and 31.1 degrees 2θ (±0.2 degrees 2θ), wherein the XRPD is made using Cu Kα radiation. In some embodiments, the solid form of Compound 1 esylate (Esylate Material A) is characterized by an XRPD pattern as substantially shown in FIG. 58.

In some embodiments, the solid form of Compound 1 esylate (Esylate Material A) is characterized by a DSC curve that comprises a broad endotherm at about 50° C. and another endothermic event with an onset at about 199° C. In some embodiments, the solid form of Compound 1 esylate (Esylate Material A) is characterized by a DSC curve as substantially shown in FIG. 59. In some embodiments, the solid form of Compound 1 esylate (Esylate Material A) is characterized by a TGA thermogram as substantially shown in FIG. 60.

Compound 1 Esylate (Esylate Material B)

In one aspect, a solid form of Compound 1 esylate (Esylate Material B) is characterized by an XRPD pattern comprising peaks at 5.8, 11.4, and 18.9 degrees 2θ (±0.2 degrees 2θ), wherein the XRPD is made using Cu Kα radiation. In some embodiments, the solid form of Compound 1 esylate (Esylate Material B) characterized by an XRPD pattern further comprises one or more peaks at 9.5, 18.4, and 24.9 degrees 2θ (±0.2 degrees 2θ), wherein the XRPD is made using Cu Kα radiation. In some embodiments, the solid form of Compound 1 esylate (Esylate Material B) characterized by an XRPD pattern further comprises one or more peaks at 13.8, 16.4, and 27.6 degrees 2θ (±0.2 degrees 2θ), wherein the XRPD is made using Cu Kα radiation.

In one aspect, a solid form of Compound 1 esylate (Esylate Material B) is characterized by an XRPD pattern comprising peaks at 5.8, 9.5, 11.4, 13.8, 16.4, 18.4, 18.9, 24.9, and 27.6 degrees 2θ (±0.2 degrees 2θ), wherein the XRPD is made using Cu Kα radiation. In some embodiments, the solid form of Compound 1 esylate (Esylate Material B) is characterized by an XRPD pattern as substantially shown in FIG. 61.

Compound 1 Esylate (Esylate Material C)

In one aspect, a solid form of Compound 1 esylate (Esylate Material C) is characterized by an XRPD pattern comprising peaks at 5.0, 6.3, and 7.3 degrees 2θ (±0.2 degrees 2θ), wherein the XRPD is made using Cu Kα radiation. In some embodiments, the solid form of Compound 1 esylate (Esylate Material C) characterized by an XRPD pattern further comprises one or more peaks at 17.1, 17.4, and 19.9 degrees 2θ (±0.2 degrees 2θ), wherein the XRPD is made using Cu Kα radiation. In some embodiments, the solid form of Compound 1 esylate (Esylate Material C) characterized by an XRPD pattern further comprises one or more peaks at 18.1, 22.7, and 24.6 degrees 2θ (±0.2 degrees 2θ), wherein the XRPD is made using Cu Kα radiation.

In one aspect, a solid form of Compound 1 esylate (Esylate Material C) is characterized by an XRPD pattern comprising peaks at 5.0, 6.3, 7.3, 17.1, 17.4, 18.1, 19.9, 22.7, and 24.6 degrees 2θ (±0.2 degrees 2θ), wherein the XRPD is made using Cu Kα radiation. In some embodiments, the solid form of Compound 1 esylate (Esylate Material C) is characterized by an XRPD pattern as substantially shown in FIG. 62.

Compound 1 Esylate (Esylate Material D)

In one aspect, a solid form of Compound 1 esylate (Esylate Material D) is characterized by an XRPD pattern comprising peaks at 5.8, 11.4, and 18.1 degrees 2θ (±0.2 degrees 2θ), wherein the XRPD is made using Cu Kα radiation. In some embodiments, the solid form of Compound 1 esylate (Esylate Material D) characterized by an XRPD pattern further comprises one or more peaks at 10.2, 18.8, and 19.5 degrees 2θ (±0.2 degrees 2θ), wherein the XRPD is made using Cu Kα radiation. In some embodiments, the solid form of Compound 1 esylate (Esylate Material D) characterized by an XRPD pattern further comprises one or more peaks at 18.4, 23.6, and 24.9 degrees 2θ (±0.2 degrees 2θ), wherein the XRPD is made using Cu Kα radiation.

Figure 63:
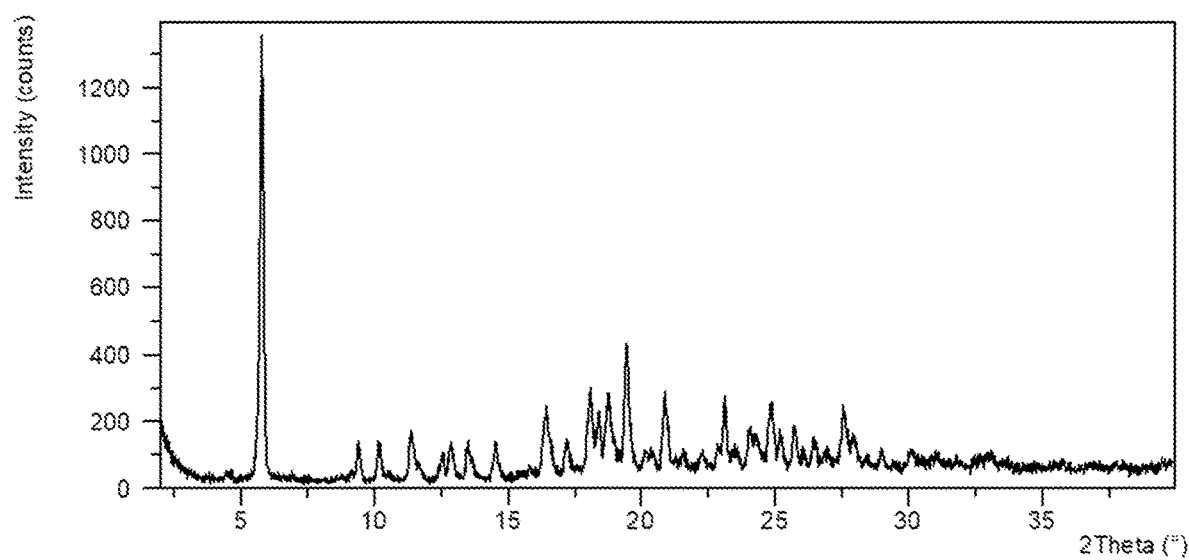
FIG. 63 shows the XRPD pattern of Compound 1 esylate Material D.

In one aspect, a solid form of Compound 1 esylate (Esylate Material D) is characterized by an XRPD pattern comprising peaks at 5.8, 10.2, 11.4, 18.1, 18.4, 18.8, 19.5, 23.6, 24.9 degrees 2θ (±0.2 degrees 2θ), wherein the XRPD is made using Cu Kα radiation. In some embodiments, the solid form of Compound 1 esylate (Esylate Material D) is characterized by an XRPD pattern as substantially shown in FIG. 63.

Methods of Treatment

The compounds disclosed herein, such as any one of the solid forms of Compound 1, are useful for the treatment of diseases or conditions mediated by Cot. Non-limiting examples of diseases or conditions mediated by Cot include, without limitation, cancer, diabetes, and inflammatory diseases such as rheumatoid arthritis (RA), multiple sclerosis (MS), inflammatory bowel disease (IBD), sepsis, psoriasis, misregulated TNF expression and graft rejection.

In further embodiments, the methods are provided for alleviating a symptom of a disease or disorder mediated by Cot. In some embodiments, the methods include identifying a mammal having a symptom of a disease or disorder mediated by Cot, and providing to the mammal an amount of a compound as described herein effective to ameliorate (i.e., lessen the severity of) the symptom.

In some embodiments, the disease or condition mediated by Cot is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease or condition mediated by Cot is diabetes, which includes any metabolic disorder characterized by impaired insulin production and glucose tolerance. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the disease or condition mediated by Cot is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated by Cot is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding). The term "wherein said symptoms are reduced" refers to a qualitative or quantitative reduction in detectable symptoms, including but not limited to a detectable impact on the rate of recovery from disease (e.g., rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods are generally applicable to a subject having IBD of any level or degree of disease activity.

In some embodiments, the disease or condition treated by the administration of a compound or a composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g., renal cell carcinoma carcinoma of the renal pelvis), cancer of the penis, cancer of the small intestine, cancer of the thyroid, cancer of the urethra, cancers of the bloodsuch as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic mueloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lynphocytic lymphomas, myofascial disorders, myositis, neuralgia, neurodegenerative disorders, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections (e.g., influenza) and wound healing.

Criteria useful for assessment of disease activity in subjects with ulcerative colitis can be found in, e.g., Truelove et al. (1955) Br Med J 2:1041-1048. Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In certain embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition. Tpl2 can mediate immune related liver diseases or conditions. (Vyrla et. al., The Journal of Immunology, 2016, 196; Perugorria et. al., Hepatology, 2013; 57:1238-1249.)

In some embodiments, the disease or condition mediated by Cot is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g., prednisolone) and phosophodiesterase inhibitors (e.g., pentoxifylline) can be used to treat alcoholic hepatitis. The compounds herein can be used as stand-alone treatments or in combination with the current treatments for alcoholic hepatitis.

In some embodiments, the disease or condition mediated by Cot is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's pheenomenon.

Improvements in any of the foregoing response criteria are specifically provided by the methods of the present disclosure.

Pharmaceutical Compositions and Modes of Administration

Compounds provided herein, such as any one of the solid forms of Compound 1, are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or isotopically-labeled analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or isotopically-labeled analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, vinylpyrrolidone-vinyl acetate copolymer (copovidone), cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or isotopically-labeled analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or isotopically-labeled analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application, such as any one of the solid forms of Compound 1, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 150 to 750 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 150 to 750 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 1500 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Process Claims for Solid Forms of Compound 1

The solid forms of Compound 1 can be prepared by a variety of methods. For example, Compound 1 can be dissolved in a single solvent system and allowed to crystallize.

Alternatively, Compound 1 can be crystallized from a two-solvent system by dissolving Compound 1 in a solvent, and then adding an anti-solvent to the mixture causing Compound 1 to crystallize.

For example, the solvent can be a polar solvent, which can be, for instance, a protic solvent. Other suitable solvents include non-polar solvents. Suitable solvents include, but are not limited to, water, alkanes such as heptanes, hexanes, and cyclohexane, petroleum ether, alcohols (methanol, ethanol, propanol, isopropanol), ethylene glycol and polyethylene glycol such as PEG400, alkanoates such as ethyl acetate, propyl acetate, isopropyl acetate, and butyl acetate, acetonitrile, alkanones such as acetone, methyl ethyl ketone (MEK), methyl propyl ketone (MPK) and methyl iso-butyl ketone (MIBK), ethers such as diethyl ether, methyl-t-butyl ether, tetrahydrofuran, 2-methyl-tetrahydrofuran, 1,2-dimethoxy ethane and 1,4-dioxane, aromatics such as benzene and toluene, halogenated solvents such as methylene chloride, chloroform and carbon tetrachloride, dimethylsulfoxide (DMSO), and dimethylformamide (DMF). Suitable solvents also include, but are not limited to halogenated alcohols (trifluoromethanol, trifluoroethanol (TFE), hexafluoroisopropanol (HFIPA)).

The methods of preparing solid forms of Compound 1 can be performed under any suitable reaction conditions. For example, the methods of preparing the solid forms of Compound 1 can be performed at any suitable temperature, such as, but not limited to, below room temperature, at room temperature, or above room temperature. In some embodiments, the temperature can be from about −78° C. to about 100° C., or from about 0° C. to about 50° C., or from about 10° C. to about 30° C. In some embodiments, the temperature can be the reflux temperature of the particular solvent used in the method. In other embodiments, solid forms of Compound 1 can be heated above at suitable temperature, such as about 100° C., such that one solid form of Compound 1 forms a second solid form of Compound 1.

The methods of preparing solid forms of Compound 1 can be performed for any suitable time. For example, the time can be for minutes, hours or days. In some embodiments, the time can be several hours, such as overnight. The methods of preparing solid forms of Compound 1 can be also be performed at any suitable pressure. For example, the pressure can be below atmospheric pressure, at about atmospheric pressure, or above atmospheric pressure.

When multiple solvents are used in the methods of the present invention, the ratio of solvents in the above methods can be any suitable ratio from about 1:1 to about 1:9, including about 1:2, 1:3, 1:4, 1:5, 1:6, 1:7 and about 1:8 by volume, The ratio of Compound 1 to solvent, can be any suitable ratio to promote crystallization. For example, the Compound I to solvent ratio can be from about 1:5 (weight/volume, or w/v) to about 1:50 (w/v), including about 1:6, 1:7, 1:8, 1:9, 1:10, 1:11, 1:12, 1:13, 1:14, 1:15, 1:20, 1:25, 1:30, 1:35, 1:40 and about 1:45 (w/v).

Crystallization can be induced by methods known in the art, for example by mechanical means such as scratching or rubbing the contact surface of the reaction vessel with, e.g., a glass rod. Optionally the saturated or supersaturated solution may be inoculated with seed crystals. The mixture for crystallizing Compound 1 can also contain a seed crystal of crystalline Compound 1.

Isolation of the desired solid form can be accomplished by removing the solvent and precipitating solvent from the crystals. Generally this is carried out by known methods, such as, filtration, suction filtration, decantation or centrifugation. Further isolation can be achieved by removing any excess of the solvent(s) from the solid form by methods known to the one skilled in the art as for example application of a vacuum, and/or by heating.

In one aspect is provided a method of preparing the solid form of Compound 1 (Freebase Form I) comprising: (i) forming a mixture comprising Compound 1 and a solvent mixture; (ii) cooling the mixture to provide a slurry; (iii) filtering the slurry to provide a wet solid; and (iv) drying the wet solid to provide the solid form of Compound 1 (Freebase Form I).

In some embodiments, the solvent mixture comprises methyl tert-butyl ether, 2-methyltetrahydrofuran, and/or acetonitrile. In some embodiments, the mixture is cooled to a temperature ranging from about −5° C. to about 5° C. to provide the slurry. In some embodiments, the mixture is cooled to about 0° C. to provide the slurry.

In one aspect is provided a method of preparing the solid form of Compound 1 oxalate (Oxalate Form I) comprising: (i) forming a mixture comprising Compound 1 (Freebase Form I), oxalic acid, and a solvent; (ii) stirring the mixture to provide a slurry; (iii) filtering the slurry to provide a wet solid; and (iv) drying the wet solid to provide the solid form of Compound 1 oxalate (Oxalate Form I).

In some embodiments, the solvent comprises acetonitrile, water, THF, methanol, ethanol, acetone, DCM or a combination thereof.

In one aspect is provided a method of preparing the solid form of Compound 1 maleate comprising: (i) forming a mixture of comprising Compound 1 (Freebase Form I), maleic acid, and a solvent; (ii) stirring the mixture to provide a slurry; (iii) centrifuging the slurry to provide a wet solid; and (iv) drying the wet solid to provide the solid form of Compound 1 maleate.

In some embodiments, the solvent comprises acetonitrile. In some embodiments, the mixture is stirred at about 20° C. to provide the slurry.

In one aspect is provided a method of preparing the solid form of Compound 1 camsylate (Camsylate Form I) comprising: (i) forming a mixture comprising Compound 1 free base, (+)-camphor-10-sulfonic acid, and a solvent; (ii) heating the mixture; (iii) cooling the mixture to provide a slurry; (iv) centrifuging the slurry to provide a wet solid; and (v) drying the wet solid to provide the solid form of Compound 1 camsylate (Camsylate Form I).

In some embodiments, the solvent comprises isopropanol. In some embodiments, the mixture is heated to about 90° C. and then cooled to about 22° C.

In one aspect is provided a method of preparing the solid form of Compound 1 camsylate (Camsylate Form II) comprising: (i) forming a mixture comprising Compound 1 camsylate (Camsylate Form I) and a solvent; (ii) filtering the slurry to provide a wet solid; and (iii) drying the wet solid to provide the solid form of Compound 1 camsylate (Camsylate Form II).

In some embodiments, the solvent comprises MEK, 2-MeTHF, MTBE, methanol/IPE mixture, MIBK, DCM/heptane mixture, EtOAc, IPAc, or toluene. In some embodiments, forming a mixture further comprises stirring at about 22° C.

In one aspect is a method of preparing the solid form of Compound 1 camsylate (Camsylate Form III) comprising: (i) forming a mixture comprising Compound 1 camsylate (Camsylate Form I) and a solvent; (ii) filtering the slurry to provide a wet solid; and (iii) drying the wet solid to provide the solid form of Compound 1 camsylate (Camsylate Form III).

In some embodiments, the solvent comprises acetonitrile. In some embodiments, forming a mixture further comprises stirring at about 22° C.

The present invention, thus generally described, will be understood more readily by reference to the following examples, which are provided by way of illustration and are not intended to be limiting of the present invention.

EXAMPLES

Equipment and Materials

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a thin layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b on the following settings: 45 kV 40 mA, Kα1=1.5406 Å, scan range 2-40°2θ, step size 0.0167°2θ. All °2θ values in this document are ±0.2°2θ.

Differential Scanning Calorimetry (DSC) thermograms were collected using a TA Instruments Q2000 differential scanning calorimeter. Temperature calibration was performed using NIST-traceable indium metal. The sample was placed into a T-zero aluminum DSC pan covered with a lid with or without a pinhole, and crimped or not crimped. The weight was then accurately recorded. A weighed aluminum pan configured as the sample pan was placed on the reference side of the cell. The sample was heated from no less than −30° C. to 200° C. or above at 10° C./minute.

Thermogravimetric Analysis (TGA) thermograms were collected using a TA Instruments Q5000 or Q500 thermogravimetric analyzer. Temperature calibration was performed using nickel and Alumel™. Typically 1-5 mg of sample was placed in a tared open aluminum pan and inserted into the TG furnace. The furnace was heated under a nitrogen purge. The sample was heated from ambient to 250° C. or above at 10° C./minute.

Example 1. Compound 1 Freebase

Compound 1 Freebase Form I

Compound 1 Freebase Form I was prepared by combining Compound A (scaling factor, 1 equiv), copper sulfate (0.1 equiv), sodium ascorbate (0.3 equiv), 2-methyltetrahydrofuran (5 volumes), and water (0.7 volumes) at about 20° C. In a second vessel, 2-azido-1,3-dimethylimidazolium hexafluorophosphate (ADMP, 1.37 equiv) and acetonitrile (2.4 volumes) are combined at about 20° C. In a third vessel, Compound B (1.26 equiv) and acetonitrile (1.8 volumes) were combined, and then diisopropylethylamine (2.33 equiv) was added at about 20° C. The ADMP and Compound B mixtures in the second and third vessels were combined in a tube reactor to form Compound C, and the resulting mixture was collected in the first vessel containing Compound A. The combined reaction mixture was agitated for about 4 hours at about 20° C., and then methyl tert-butyl ether (4 volumes) was added. The mixture was cooled to about 0° C. and the resulting slurry was filtered. The solids were rinsed sequentially with methyl tert-butyl ether (3 volumes), water (3 volumes), and methyl tert-butyl ether (3 volumes). The solids were dried under vacuum at about 40° C. to provide Compound 1 Freebase Form I. The reaction scheme is presented in FIG. 1.

Figure 2:
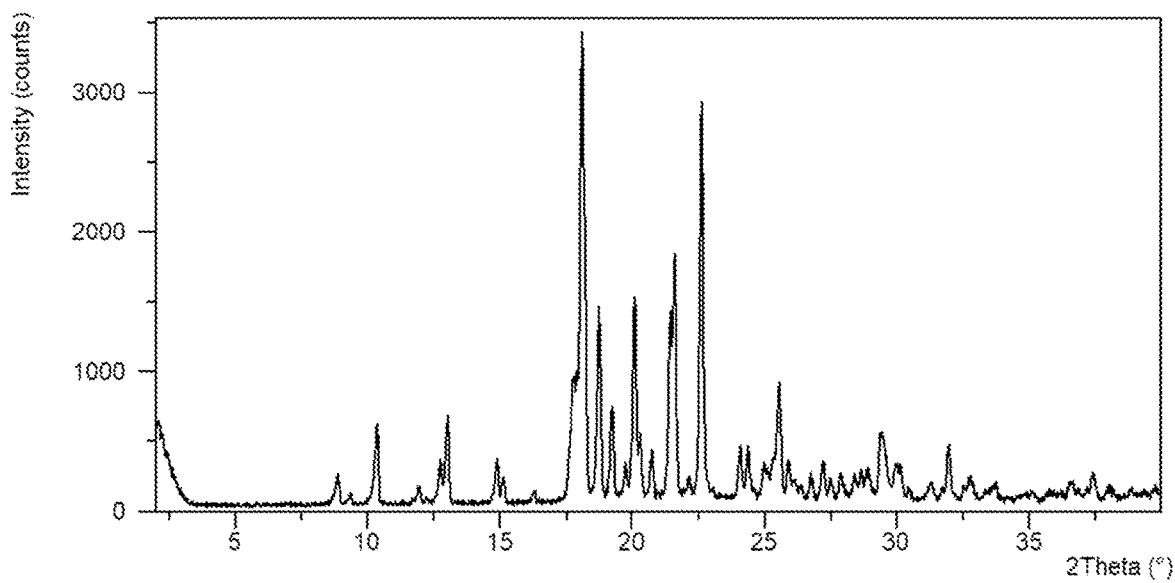
FIG. 2 shows the XRPD pattern of Compound 1 Freebase Form I.

The XRPD pattern of Compound 1 Freebase Form I is presented in FIG. 2. Table 1 summarizes the peaks in the XRPD pattern.

TABLE 1

XRPD peaks list of Compound 1 Freebase Form I

| No. | Pos. [°2Th.] | Rel. Int. [%] |
| --- | --- | --- |
| 1 | 8.9 | 5 |
| 2 | 9.4 | 2 |
| 3 | 10.4 | 16 |
| 4 | 12.0 | 3 |
| 5 | 12.7 | 9 |
| 6 | 13.0 | 18 |
| 7 | 14.9 | 9 |
| 8 | 15.1 | 5 |
| 9 | 16.3 | 2 |
| 10 | 17.8 | 25 |
| 11 | 18.1 | 100 |
| 12 | 18.3 | 44 |
| 13 | 18.8 | 42 |
| 14 | 19.2 | 20 |
| 15 | 19.8 | 8 |
| 16 | 20.1 | 43 |
| 17 | 20.3 | 14 |
| 18 | 20.7 | 11 |
| 19 | 21.4 | 40 |
| 20 | 21.6 | 53 |
| 21 | 22.1 | 5 |
| 22 | 22.6 | 84 |
| 23 | 24.1 | 11 |
| 24 | 24.4 | 11 |
| 25 | 24.9 | 7 |
| 26 | 25.6 | 25 |
| 27 | 25.9 | 8 |
| 28 | 26.7 | 4 |
| 29 | 27.2 | 8 |
| 30 | 27.5 | 4 |
| 31 | 27.9 | 5 |

TABLE 1-continued

XRPD peaks list of Compound 1 Freebase Form I

| No. | Pos. [°2Th.] | Rel. Int. [%] |
|---|---|---|
| 32 | 28.4 | 5 |
| 33 | 28.7 | 6 |
| 34 | 28.9 | 6 |
| 35 | 29.4 | 12 |
| 36 | 30.0 | 7 |
| 37 | 30.1 | 7 |
| 38 | 30.5 | 2 |
| 39 | 31.3 | 3 |
| 40 | 31.9 | 10 |

Figure 3:
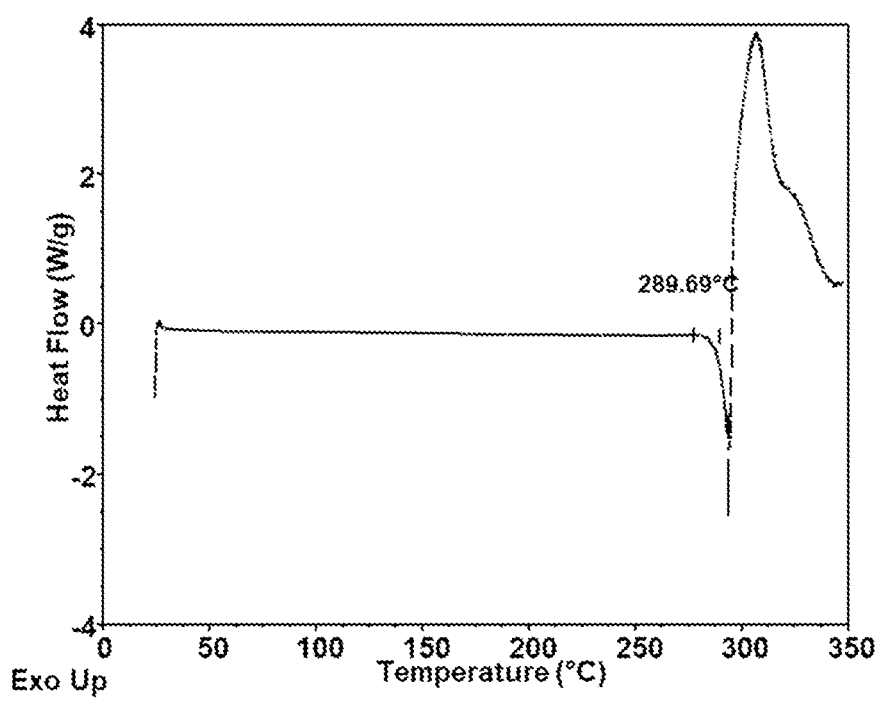
FIG. 3 shows the DSC thermogram of Compound 1 Freebase Form I.
Figure 4:
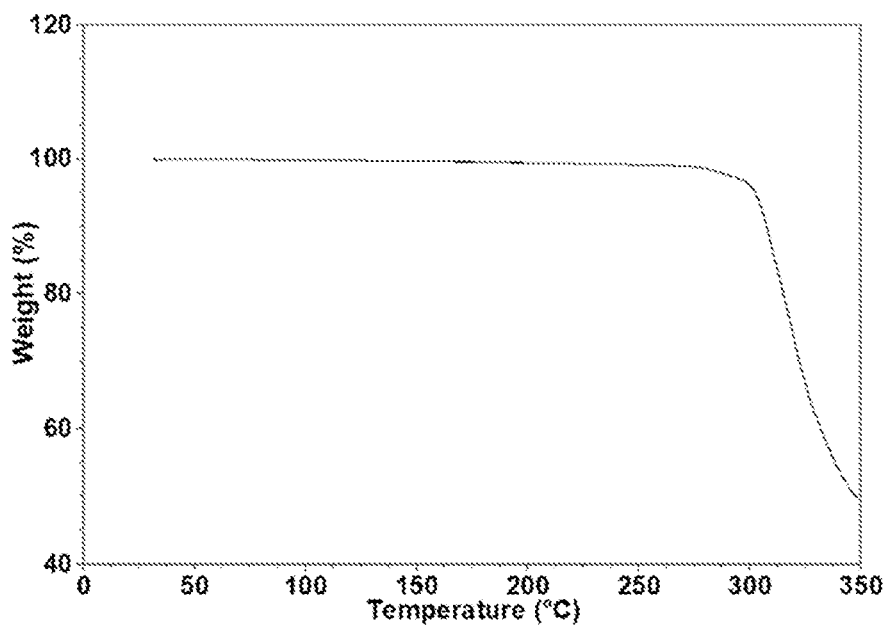
FIG. 4 shows the TGA thermogram of Compound 1 Freebase Form I.

The DSC thermogram of Compound 1 Freebase Form I is shown in FIG. 3. There is an endothermic event followed by an exothermic event at approximately 270° C. The TGA thermogram of Compound 1 Freebase Form I is shown FIG. 4.

Compound 1 Freebase Form III

Compound 1 freebase Form III was prepared by stirring Compound 1 oxalate salt Form I in water at a concentration of about 0.4 mg/mL for about 1 h at approximately 20° C. The resulting slurry was then centrifuged and filtered. The solids were analyzed by XRPD. Compound 1 Freebase Form III was also prepared by stirring Compound 1 maleate in water under the same conditions.

Figure 5:
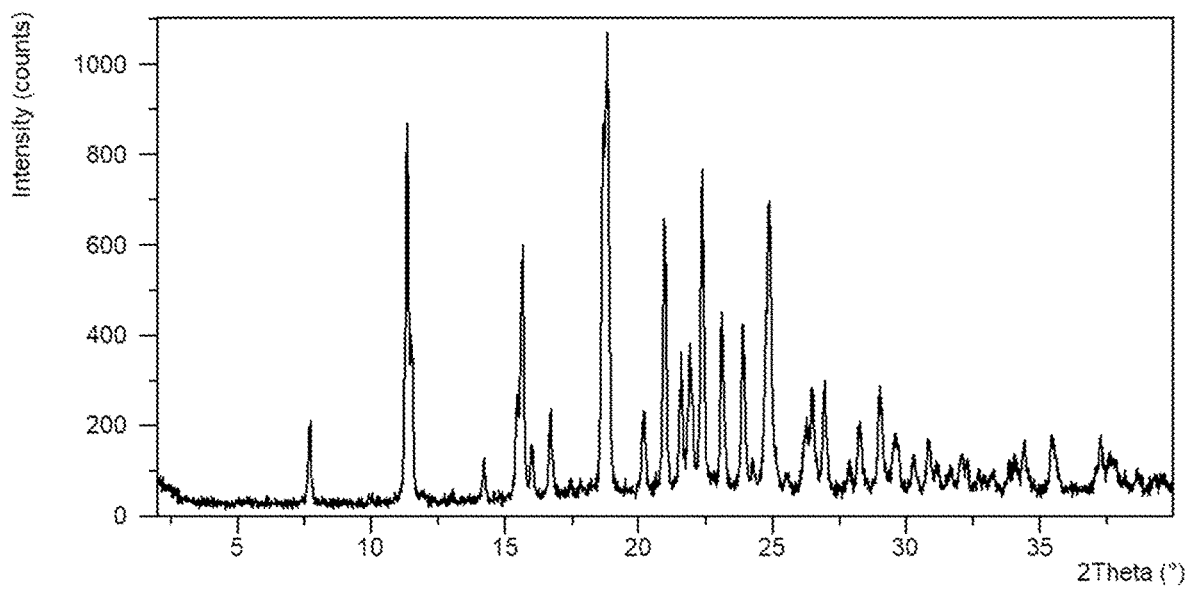
FIG. 5 shows the XRPD pattern of Compound 1 Freebase Form III.

The XRPD pattern of Compound 1 freebase Form III is presented FIG. 5. Table 2 summarizes the peaks in the XRPD pattern.

TABLE 2

XRPD peak list of Compound 1 freebase Form III

| No. | Pos. [°2Th.] | Rel. Int. [%] |
|---|---|---|
| 1 | 7.7 | 16 |
| 2 | 11.3 | 84 |
| 3 | 11.5 | 36 |
| 4 | 14.2 | 8 |
| 5 | 15.5 | 22 |
| 6 | 15.6 | 55 |
| 7 | 16.0 | 11 |
| 8 | 16.7 | 20 |
| 9 | 18.7 | 82 |
| 10 | 18.8 | 100 |
| 11 | 20.2 | 20 |
| 12 | 21.0 | 63 |
| 13 | 21.6 | 28 |
| 14 | 21.9 | 30 |
| 15 | 22.4 | 73 |
| 16 | 23.1 | 42 |
| 17 | 23.9 | 39 |
| 18 | 24.9 | 65 |
| 19 | 26.2 | 15 |
| 20 | 26.5 | 23 |
| 21 | 26.9 | 25 |
| 22 | 28.3 | 15 |
| 23 | 29.0 | 24 |
| 24 | 29.6 | 12 |
| 25 | 30.3 | 8 |
| 26 | 30.9 | 11 |
| 27 | 32.1 | 8 |
| 28 | 34.4 | 9 |
| 29 | 35.4 | 12 |
| 30 | 37.3 | 11 |

Figure 6:
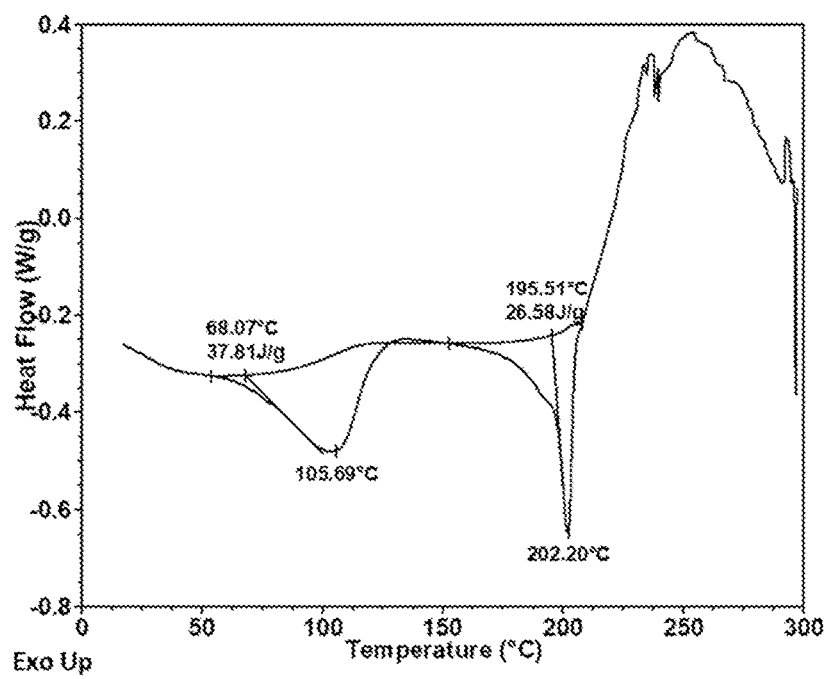
FIG. 6 shows the DSC thermogram of Compound 1 Freebase Form III.
Figure 7:
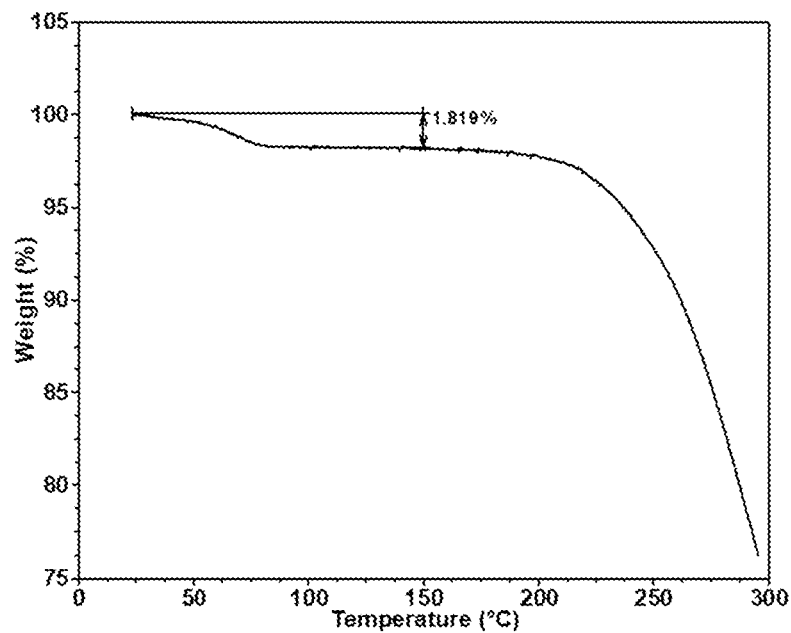
FIG. 7 shows the TGA thermogram of Compound 1 Freebase Form III.

The DSC thermogram of Compound 1 freebase Form III is presented in FIG. 6. There are two endothermic events with onsets at about 68° C. and 196° C. The TGA thermogram of Compound 1 freebase Form III is presented in FIG. 7. It indicates that the solid contains about 1.8% of residual solvent.

Example 2. Compound 1 HCl Material A

Figure 8:
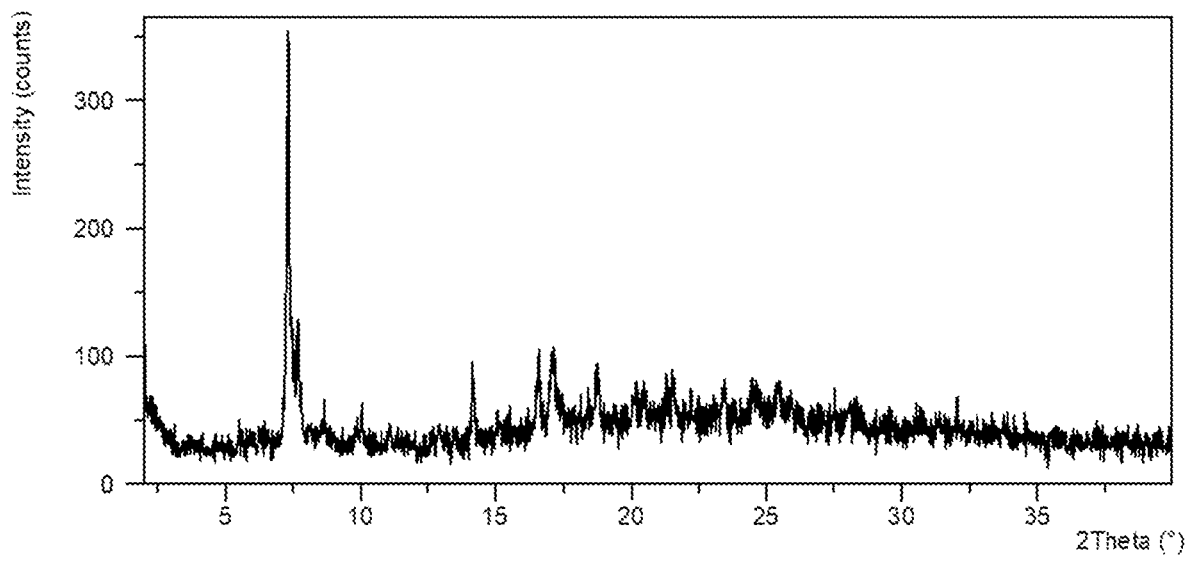
FIG. 8 shows the XRPD pattern of Compound 1 HCl Material A.

Compound 1 HCl Material A was prepared by adding one equiv. of HCl via a 12.1 M aqueous HCl solution to approximately 100 mg of Compound 1 Freebase Form I in 0.4 mL of acetonitrile. The resulting slurry was stirred for about 16 h then filtered, and dried at about 22° C. The XRPD pattern of Compound 1 HCl Material A is shown in FIG. 8. Table 3 summarizes the peaks in the XRPD pattern.

TABLE 3

XRPD peak list of Compound 1 HCl Material A

| No. | Pos. [°2Th.] | Rel. Int. [%] |
|---|---|---|
| 1 | 7.3 | 100 |
| 2 | 7.7 | 29 |
| 3 | 8.6 | 19 |
| 4 | 9.9 | 4 |
| 5 | 14.2 | 15 |
| 6 | 16.6 | 16 |
| 7 | 17.1 | 18 |
| 8 | 18.7 | 14 |
| 9 | 20.1 | 7 |
| 10 | 20.5 | 7 |
| 11 | 21.6 | 9 |
| 12 | 23.4 | 8 |
| 13 | 24.6 | 6 |
| 14 | 25.5 | 6 |

Figure 9:
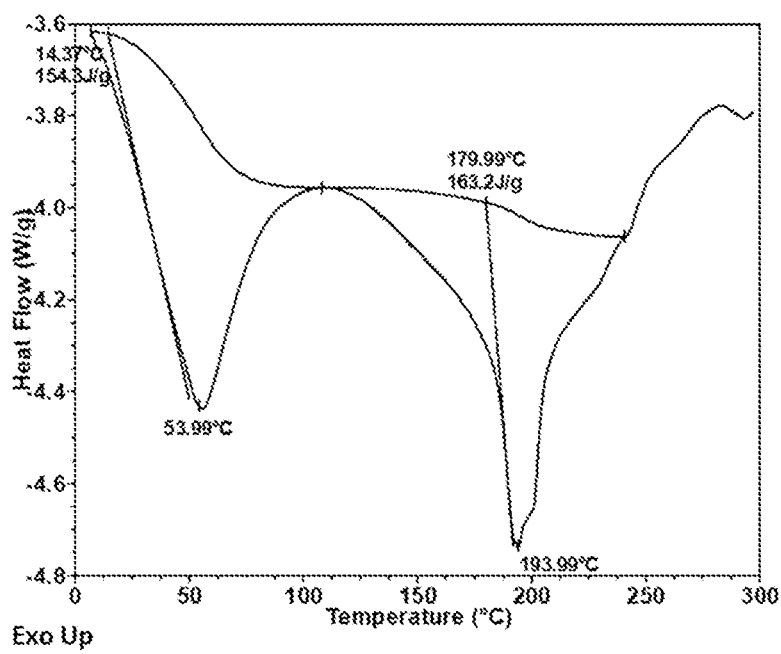
FIG. 9 shows the DSC thermogram of Compound 1 HCl Material A.
Figure 10:
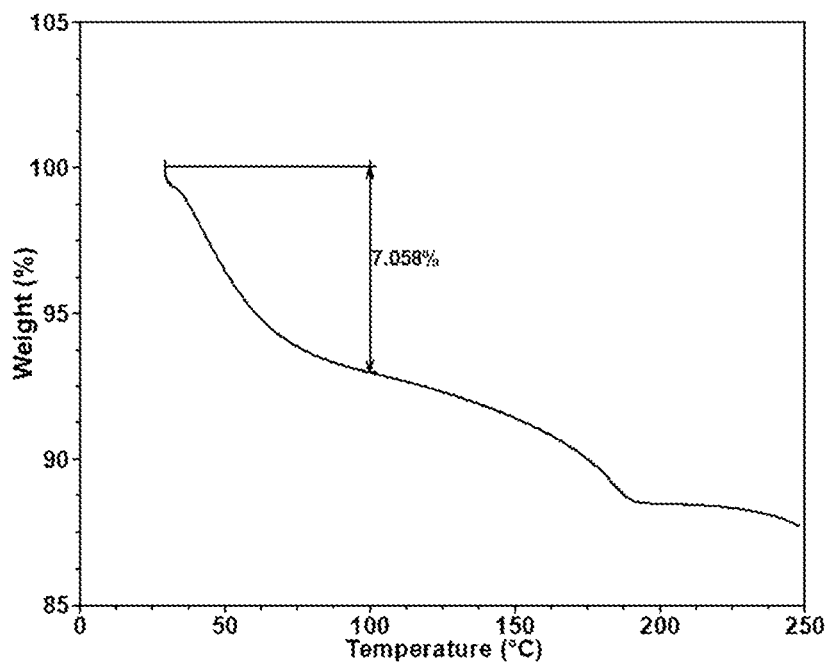
FIG. 10 shows the TGA thermogram of Compound 1 HCl Material A.

The DSC thermogram of Compound 1 HCl salt Material A is presented in FIG. 9. There are two endothermic events with onsets at approximately 14° C. and 180° C. The TGA thermogram of Compound 1 HCl salt Material A is presented in FIG. 10.

Example 3. Compound 1 Methanesulfonate

Compound 1 Methanesulfonate Material A

Compound 1 methanesulfonate Material A was prepared by adding 1.3 equiv. of methanesulfonic acid to approximately 921 mg of Compound 1 Freebase Form I suspended in about 3 mL of acetonitrile. The slurry was stirred for about 16 h. It was then filtered and dried in the vacuum oven at 50° C. for about 16 h.

Figure 11:
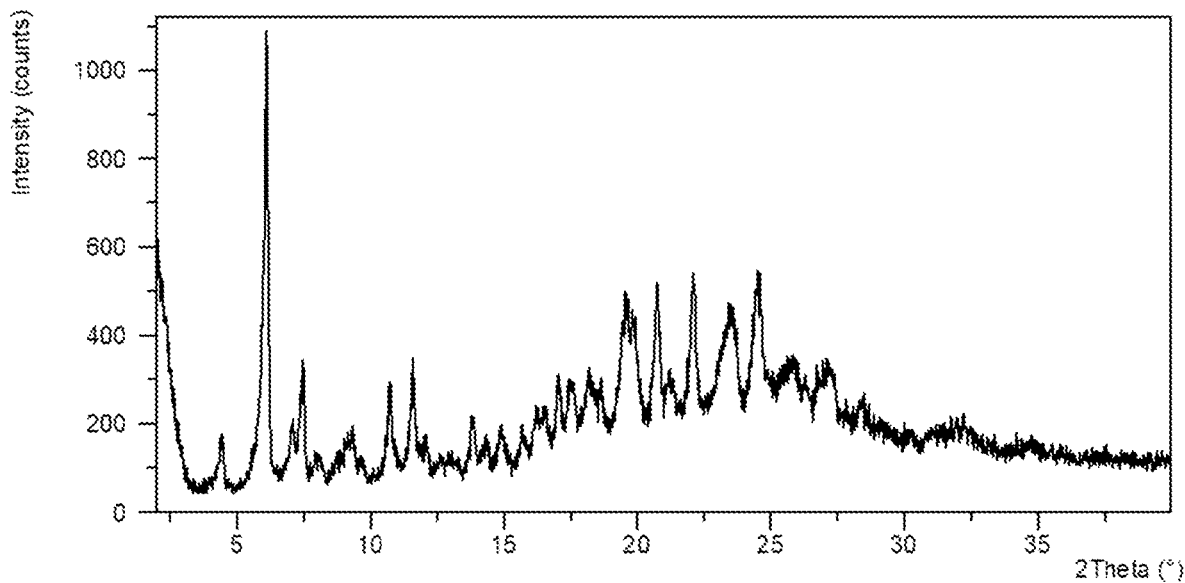
FIG. 11 shows the XRPD pattern of Compound 1 methanesulfonate Material A.

The XRPD pattern of Compound 1 methanesulfonate Material A is presented in FIG. 11. Table 4 summarizes the peaks in the XRPD pattern.

TABLE 4

XRPD peak list of Compound 1 methanesulfonate Material A

| No. | Pos. [°2Th.] | Rel. Int. [%] |
|---|---|---|
| 1 | 4.5 | 11 |
| 2 | 6.1 | 100 |
| 3 | 7.1 | 13 |
| 4 | 7.5 | 27 |
| 5 | 8.0 | 5 |
| 6 | 9.3 | 10 |
| 7 | 9.6 | 4 |
| 8 | 10.7 | 19 |
| 9 | 11.6 | 25 |
| 10 | 12.1 | 6 |
| 11 | 13.0 | 2 |
| 12 | 13.8 | 11 |
| 13 | 14.4 | 6 |

TABLE 4-continued

XRPD peak list of Compound 1 methanesulfonate Material A

| No. | Pos. [°2Th.] | Rel. Int. [%] |
|---|---|---|
| 14 | 14.9 | 8 |
| 15 | 15.7 | 9 |
| 16 | 16.2 | 9 |
| 17 | 16.5 | 11 |
| 18 | 17.1 | 18 |
| 19 | 17.5 | 17 |
| 20 | 18.2 | 19 |
| 21 | 18.6 | 16 |
| 22 | 19.6 | 35 |
| 23 | 19.9 | 31 |
| 24 | 20.7 | 39 |
| 25 | 21.2 | 17 |
| 26 | 22.1 | 37 |
| 27 | 23.6 | 29 |
| 28 | 24.5 | 37 |
| 29 | 25.9 | 18 |
| 30 | 27.3 | 14 |
| 31 | 28.4 | 7 |
| 32 | 32.0 | 2 |
| 33 | 32.3 | 3 |

Figure 12:
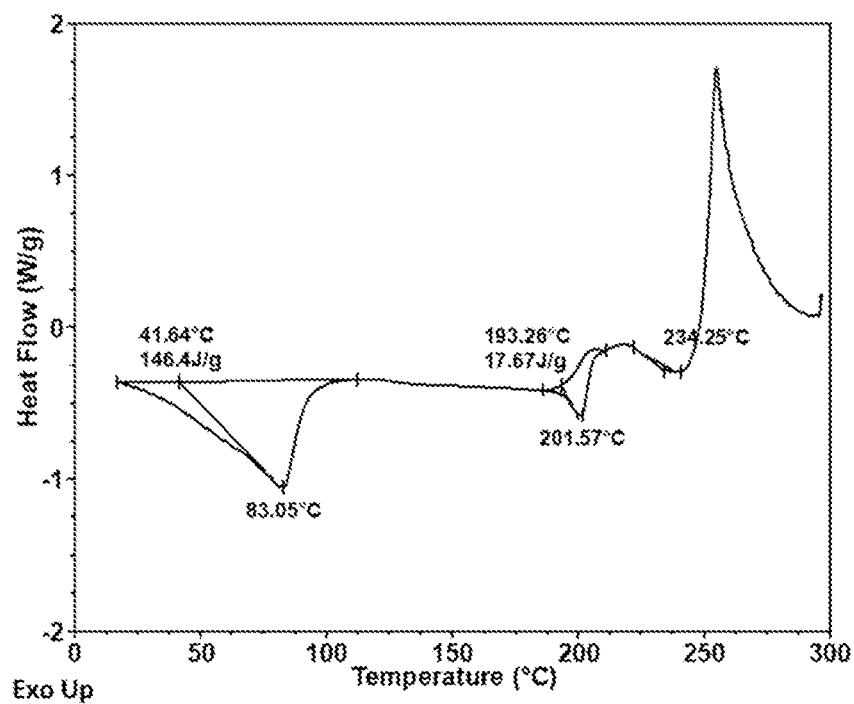
FIG. 12 shows the DSC thermogram of Compound 1 methanesulfonate Material A.
Figure 13:
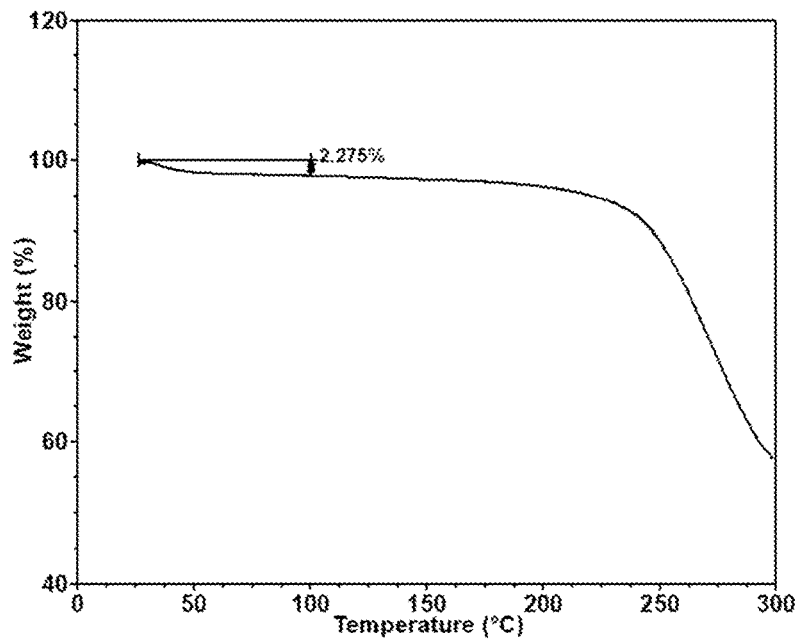
FIG. 13 shows the TGA thermogram of Compound 1 methanesulfonate Material A.

The DSC thermogram of Compound 1 methanesulfonate Material A is presented in FIG. 12. It shows three endothermic events with onsets at approximately 42° C., 193° C., and 234° C. The TGA thermogram is presented in FIG. 13. It indicates that the solid contains approximately 2% of residual solvent.

Compound 1 Methanesulfonate Material B

Figure 14:
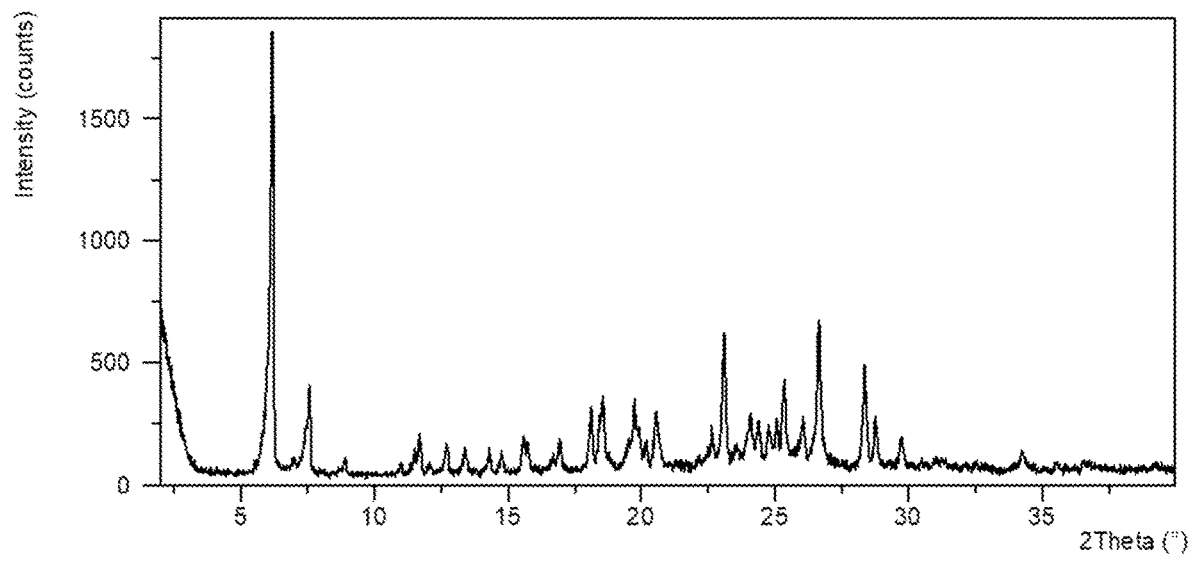
FIG. 14 shows the XRPD pattern of Compound 1 methanesulfonate Material B.

Compound 1 methanesulfonate Material B was prepared by adding 1.2 equiv. of methanesulfonic acid to about 40 mg of Compound 1 freebase Form I. 0.5 mL of dichloromethane was added and the resulting solution was stirred at 10° C. for about 16 h, then at approximately 20° C. for 14 days. The slurry was then centrifuged and air-dried. XRPD of the dry solid was then collected. FIG. 14 shows the XRPD pattern of Compound 1 methanesulfonate Material B. Table 5 summarizes the peaks in the XRPD pattern.

TABLE 5

XRPD peak list of Compound 1 methanesulfonate Material B

| No. | Pos. [°2Th.] | Rel. Int. [%] |
|---|---|---|
| 1 | 6.2 | 100 |
| 2 | 7.6 | 20 |
| 3 | 8.9 | 3 |
| 4 | 11.7 | 9 |
| 5 | 12.7 | 6 |
| 6 | 13.4 | 5 |
| 7 | 14.3 | 5 |
| 8 | 14.8 | 5 |
| 9 | 15.6 | 9 |
| 10 | 16.9 | 7 |
| 11 | 18.1 | 15 |
| 12 | 18.6 | 18 |
| 13 | 19.7 | 16 |
| 14 | 20.2 | 6 |
| 15 | 20.5 | 13 |
| 16 | 22.7 | 8 |
| 17 | 23.1 | 32 |
| 18 | 24.1 | 13 |
| 19 | 24.4 | 11 |
| 20 | 24.7 | 7 |
| 21 | 25.3 | 19 |
| 22 | 26.0 | 11 |
| 23 | 26.6 | 35 |
| 24 | 28.3 | 24 |
| 25 | 28.8 | 12 |
| 26 | 29.7 | 6 |
| 27 | 34.3 | 4 |

Figure 15:
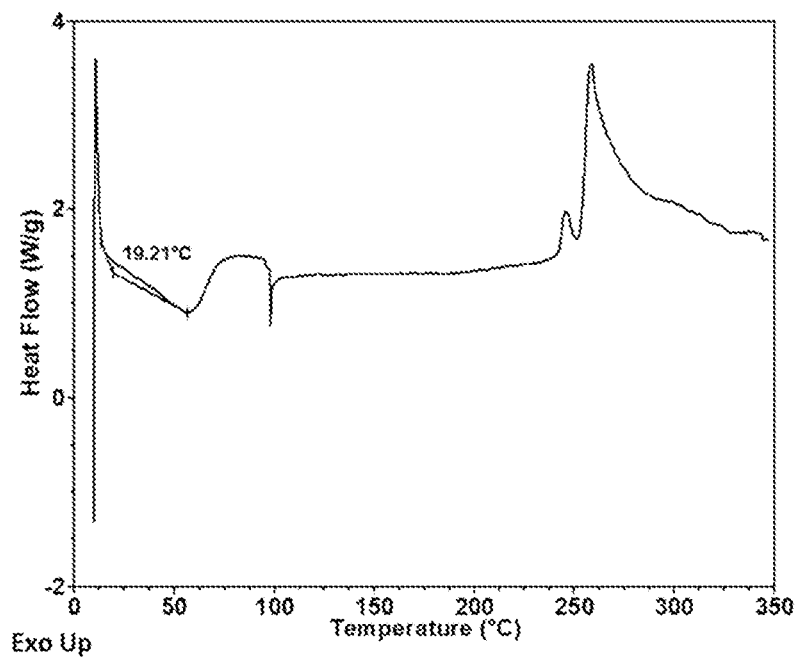
FIG. 15 shows the DSC thermogram of Compound 1 methanesulfonate Material B.
Figure 16:
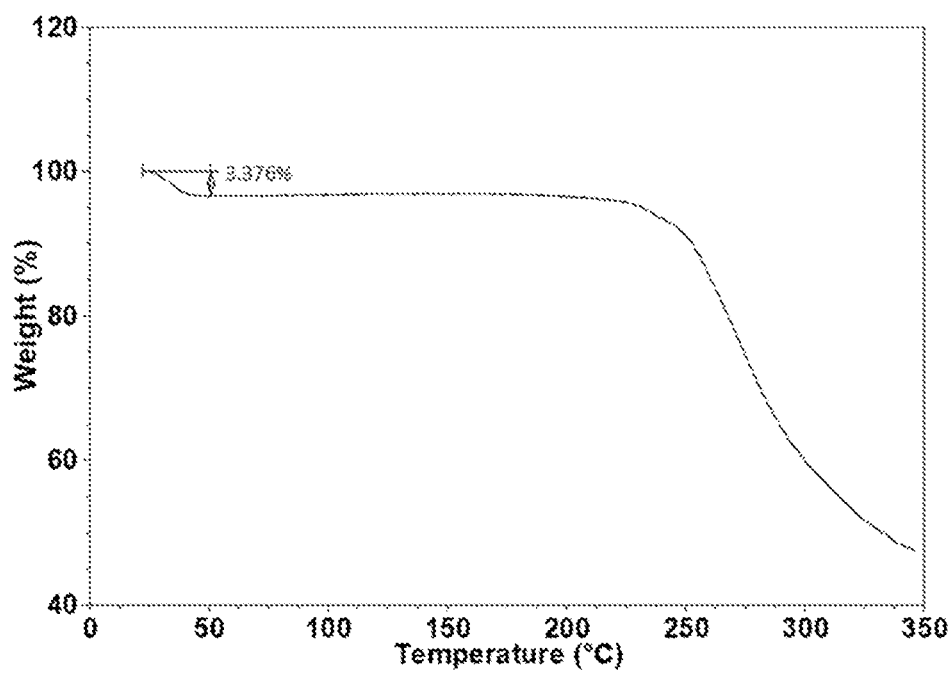
FIG. 16 shows the TGA thermogram of Compound 1 methanesulfonate Material B.

The DSC thermogram of Compound 1 methanesulfonate Material B is shown in FIG. 15. There is an endothermic event with an onset at approximately 19° C. The TGA thermogram is shown in FIG. 16. It indicates that the material contains about 3% of residual solvent.

Methanesulfonate Material C

Figure 17:
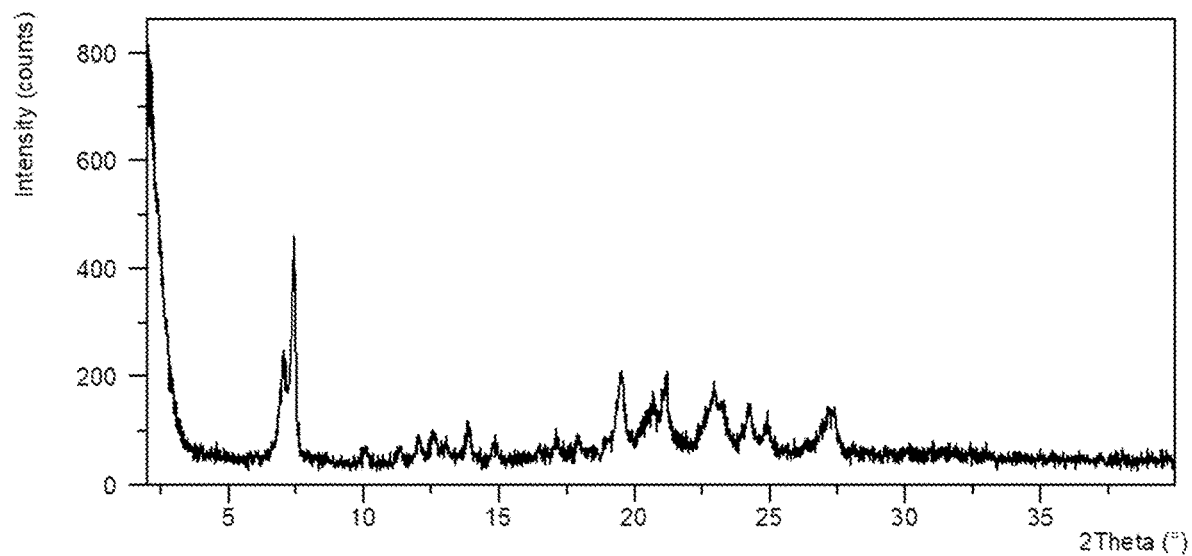
FIG. 17 shows the XRPD pattern of Compound 1 methanesulfonate Material C.

Compound 1 methanesulfonate was first prepared by adding 1.2 equiv. of methanesulfonic acid to about 37 mg of Compound 1 freebase. 0.5 mL of THF was then added. The resulting solution was stirred at 10° C. for about 3 days, then at about 20° C. for about 16 h. A slurry formed and was centrifuged. The wet-cake was dried in the vacuum oven at about 50° C. FIG. 17 is the XRPD pattern of Compound 1 methanesulfonate Material C. Table 6 summarizes the peaks in the XRPD pattern.

TABLE 6

XRPD peak list of Compound 1 methanesulfonate Material C

| No. | Pos. [°2Th.] | Rel. Int. [%] |
|---|---|---|
| 1 | 7.0 | 52 |
| 2 | 7.5 | 100 |
| 3 | 10.1 | 6 |
| 4 | 11.3 | 7 |
| 5 | 12.0 | 11 |
| 6 | 12.6 | 14 |
| 7 | 13.9 | 16 |
| 8 | 14.8 | 7 |
| 9 | 17.1 | 8 |
| 10 | 17.9 | 10 |
| 11 | 19.6 | 40 |
| 12 | 20.7 | 28 |
| 13 | 21.2 | 36 |
| 14 | 22.9 | 31 |
| 15 | 24.2 | 21 |
| 16 | 24.9 | 15 |
| 17 | 27.3 | 18 |

Figure 19:
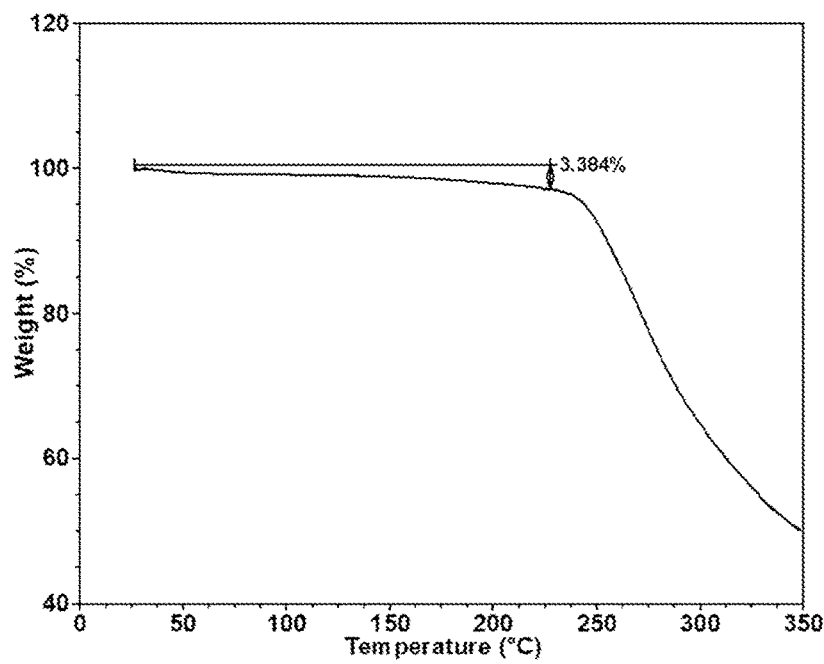
FIG. 19 shows the TGA thermogram of Compound 1 methanesulfonate Material C.

The DSC thermogram of Compound 1 methanesulfonate Material C is shown in FIG. 18. The TGA thermogram of Compound 1 methanesulfonate Material C is shown in FIG. 19. It shows that the material contains about 3% of residual solvent.

Methanesulfonate Material D

Figure 20:
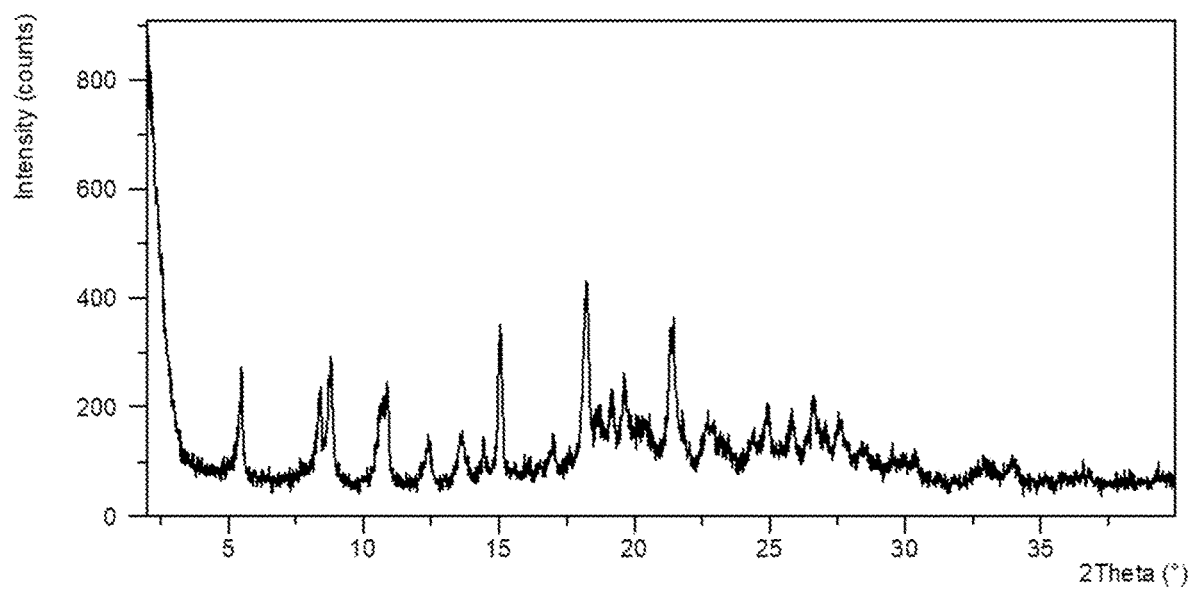
FIG. 20 shows the XRPD pattern of Compound 1 methanesulfonate Material D.

A mixture of about 850 mg of Compound 1 Freebase Form I and 1.2 equiv. of methanesulfonic acid was stirred in about 10 mL of dichloromethane for about 7 days, then vacuum-filtered. The filtered solid was then dried in the vacuum oven at about 50° C. Compound 1 methanesulfonate Material D was prepared by stirring about 30 mg of that solid in about 0.2 mL of water at approximately 20° C. The slurry was then filtered. The wet solid was then dried in the vacuum oven at approximately 50° C. The XRPD pattern of Compound 1 methanesulfonate Material is shown in FIG. 20. Table 7 summarizes the peaks in the XRPD pattern.

TABLE 7

XRPD peaks list of Compound 1 methanesulfonate Material D

| No. | Pos. [°2Th.] | Rel. Int. [%] |
|---|---|---|
| 1 | 5.5 | 50 |
| 2 | 8.4 | 47 |
| 3 | 8.8 | 60 |
| 4 | 10.6 | 36 |
| 5 | 10.9 | 47 |
| 6 | 12.4 | 20 |
| 7 | 13.6 | 22 |
| 8 | 14.4 | 17 |
| 9 | 15.0 | 80 |
| 10 | 17.0 | 20 |
| 11 | 18.2 | 100 |
| 12 | 18.6 | 34 |
| 13 | 19.2 | 40 |
| 14 | 19.6 | 53 |
| 15 | 20.3 | 29 |
| 16 | 21.4 | 76 |
| 17 | 22.6 | 28 |
| 18 | 24.4 | 22 |
| 19 | 24.9 | 33 |
| 20 | 25.8 | 33 |
| 21 | 26.6 | 41 |
| 22 | 27.5 | 33 |
| 23 | 28.5 | 16 |
| 24 | 30.1 | 10 |
| 25 | 33.0 | 9 |
| 26 | 34.0 | 10 |

Figure 22:
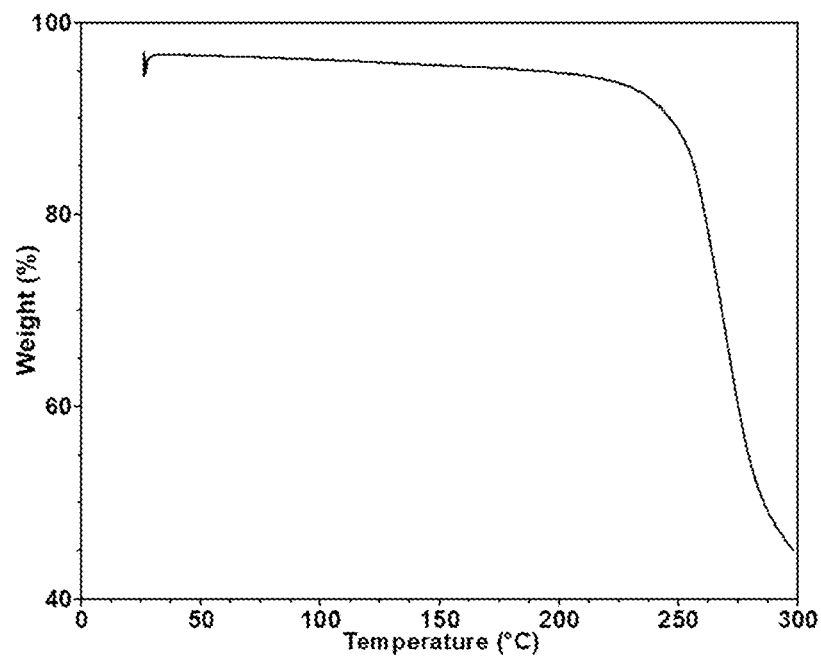
FIG. 22 shows the TGA thermogram of Compound 1 methanesulfonate Material D.

The DSC thermogram of Compound 1 methanesulfonate Material D is shown in FIG. 21. The TGA thermogram is shown in FIG. 22.

Example 4. Compound 1 Oxalate

Oxalate Material A

Compound 1 oxalate Material A was prepared by stirring about 900 mg of Compound 1 freebase Form I and about two equivs. of anhydrous oxalic acid in about 12 mL of THF for approximately 1 day. The slurry was then filtered. The wet solid was dried in the vacuum oven at about 50° C.

Compound 1 oxalate Material A can also be prepared in water/THF solvent mixtures containing between 0-2% (v/v) of water. The XRPD pattern of oxalate Material A is presented in FIG. 23. Table 8 summarizes the peaks in the XRPD pattern.

TABLE 8

XRPD peak list of Compound 1 oxalate Material A

| No. | Pos. [°2Th.] | Rel. Int. [%] |
|---|---|---|
| 1 | 2.3 | 90 |
| 2 | 4.0 | 100 |
| 3 | 4.8 | 15 |
| 4 | 6.3 | 60 |
| 5 | 6.9 | 18 |
| 6 | 8.3 | 4 |
| 7 | 11.2 | 5 |
| 8 | 11.7 | 7 |
| 9 | 12.7 | 11 |
| 10 | 13.4 | 15 |
| 11 | 14.3 | 9 |
| 12 | 15.0 | 8 |
| 13 | 16.8 | 15 |
| 14 | 17.3 | 19 |
| 15 | 18.7 | 15 |
| 16 | 21.1 | 13 |
| 17 | 21.8 | 20 |
| 18 | 22.4 | 21 |
| 19 | 23.7 | 23 |
| 20 | 25.1 | 10 |
| 21 | 26.7 | 7 |
| 22 | 27.8 | 8 |
| 23 | 30.5 | 4 |
| 24 | 31.4 | 4 |
| 25 | 32.9 | 3 |
| 26 | 34.5 | 2 |

Figure 24:
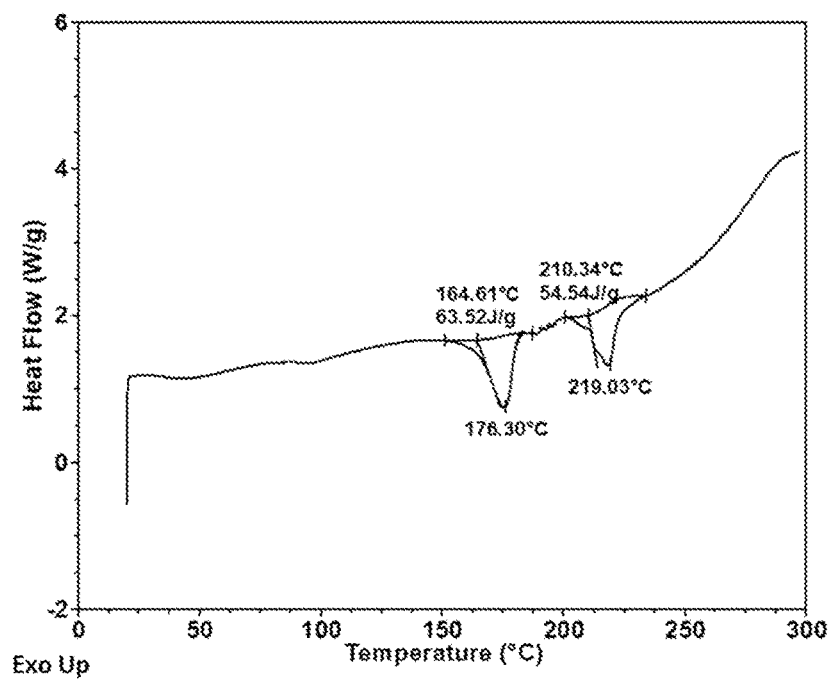
FIG. 24 shows the DSC thermogram of Compound 1 oxalate Material A.
Figure 25:
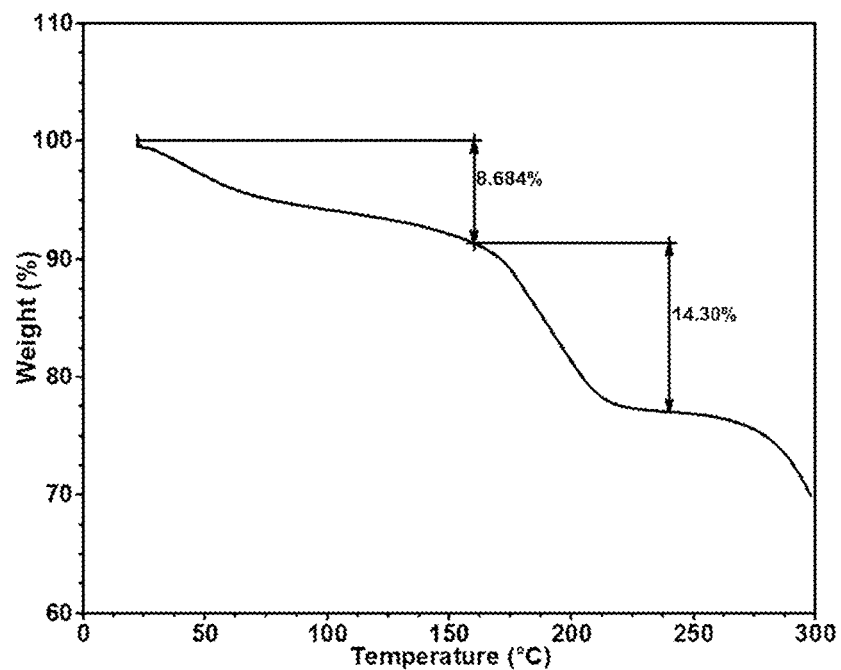
FIG. 25 shows the TGA thermogram of Compound 1 oxalate Material A.

The DSC thermogram of Compound 1 oxalate Material A is shown in FIG. 24. It shows two endothermic events with onsets at approximately 165° C. and 210° C. The TGA thermogram is shown in FIG. 25.

Oxalate Form I

Compound 1 oxalate Form I was first prepared by adding approximately 1 equiv. of anhydrous oxalic acid to about 58.5 mg of Compound 1 freebase Form I suspended in 0.2 mL of acetonitrile. The resulting slurry was stirred for approximately 16 h at about 20° C. An additional 2 mL of acetonitrile was then added to dilute the slurry. The slurry was then filtered and the solid was dried for approximately 16 h in the vacuum oven at 50° C.

Compound 1 oxalate Form I can also be prepared by stirring Compound 1 freebase Form I and up to 2 equivs. of oxalic acid in water/THF, water/methanol, water/ethanol, water/acetone, and water/DCM solvent mixtures. The resulting slurries are then filtered and dried in the vacuum oven at approximately 50° C.

Compound 1 oxalate Form I can also be prepared by stirring Compound 1 oxalate Material A in water or water/THF mixtures.

Figure 26:
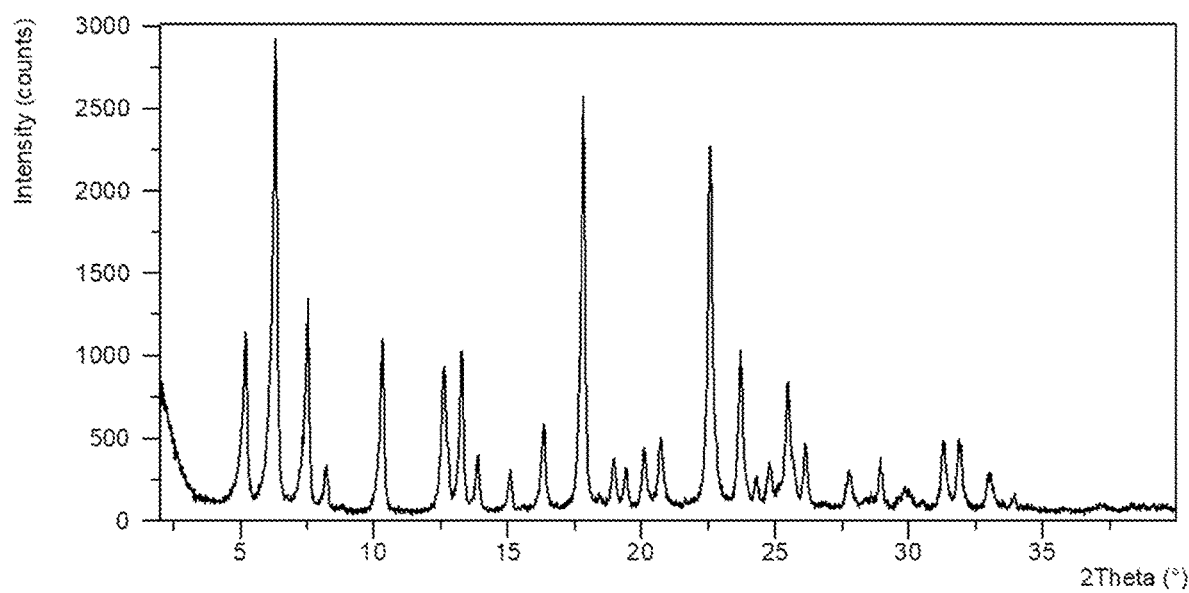
FIG. 26 shows the XRPD pattern of Compound 1 oxalate Form I.

The XRPD pattern of Compound 1 oxalate Form I is presented in FIG. 26. Table 9 summarizes the peaks in the XRPD pattern.

TABLE 9

XRPD peak list of Compound 1 oxalate Form I

| No. | Pos. [°2Th.] | Rel. Int. [%] |
|---|---|---|
| 1 | 5.2 | 36 |
| 2 | 6.3 | 100 |
| 3 | 7.5 | 43 |
| 4 | 8.2 | 8 |
| 5 | 10.3 | 37 |
| 6 | 12.6 | 32 |
| 7 | 13.3 | 36 |
| 8 | 13.9 | 13 |
| 9 | 15.1 | 9 |
| 10 | 16.4 | 19 |
| 11 | 17.9 | 91 |
| 12 | 18.5 | 3 |
| 13 | 19.0 | 11 |
| 14 | 19.4 | 10 |
| 15 | 20.1 | 14 |
| 16 | 20.7 | 17 |
| 17 | 22.6 | 81 |
| 18 | 23.7 | 33 |
| 19 | 24.3 | 8 |
| 20 | 24.8 | 10 |
| 21 | 25.5 | 29 |
| 22 | 26.1 | 14 |
| 23 | 27.8 | 8 |
| 24 | 29.0 | 11 |
| 25 | 29.8 | 5 |
| 26 | 30.5 | 2 |
| 27 | 31.3 | 15 |
| 28 | 31.9 | 16 |

TABLE 9-continued

XRPD peak list of Compound 1 oxalate Form I

| No. | Pos. [°2Th.] | Rel. Int. [%] |
|---|---|---|
| 29 | 32.9 | 7 |
| 30 | 33.3 | 3 |
| 31 | 34.0 | 3 |

Figure 27:
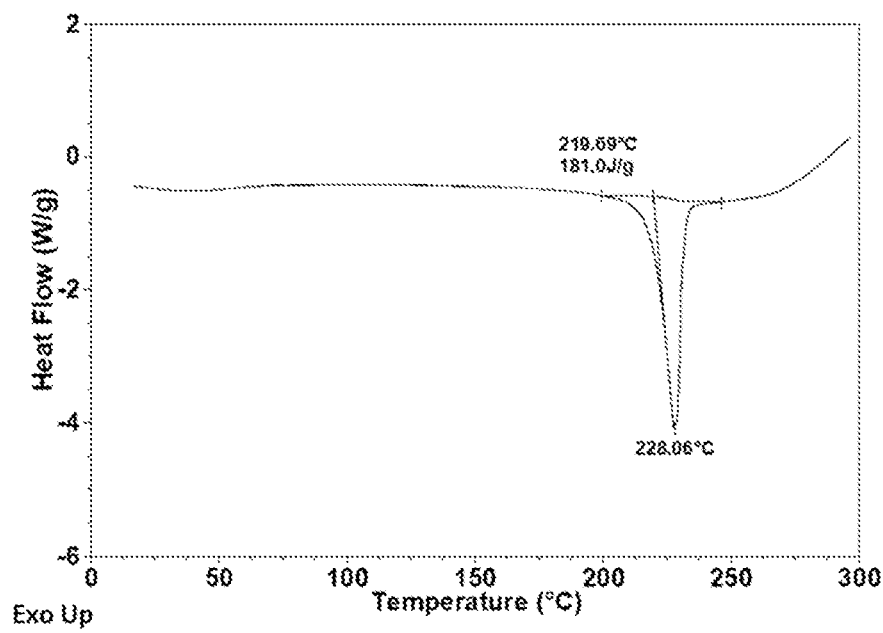
FIG. 27 shows the DSC thermogram of Compound 1 oxalate salt Form I.
Figure 28:
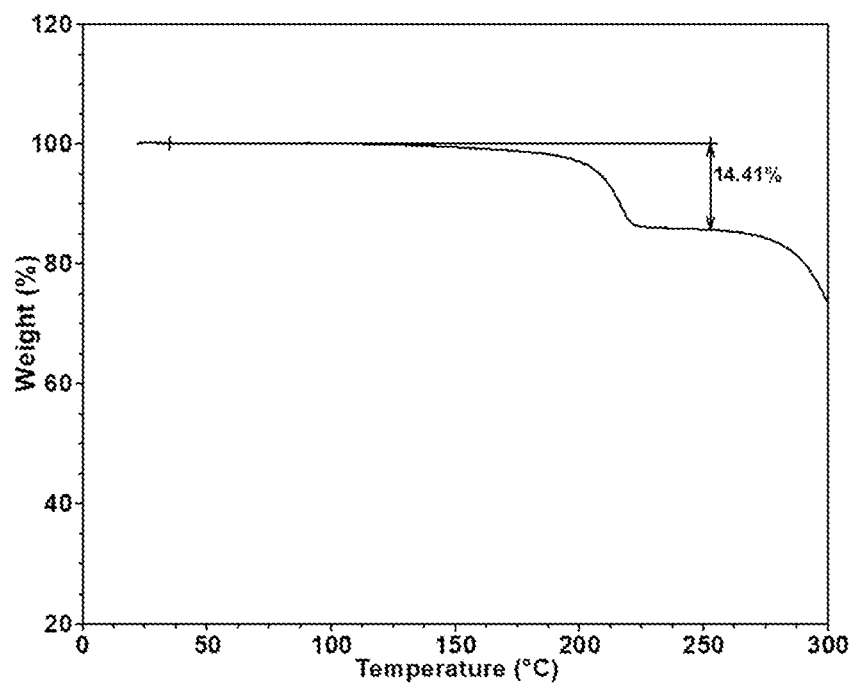
FIG. 28 shows the TGA thermogram of Compound 1 oxalate Form I.

The DSC thermogram of Compound 1 oxalate Form I is presented in FIG. 27. There is an endotherm with an onset at about 220° C. The TGA thermogram is shown in FIG. 28. The sample loses approximately 14% of its weight at a temperature of about 200° C.

Oxalate Form II

Compound 1 oxalate Form II was first prepared as a mixture of oxalate Form I and Form II. That mixture was obtained by stirring Compound 1 freebase Form I and about 3 equiv. of oxalic acid in THF at about 20° C. for approximately 16 h. The slurry was then filtered and the wet cake was dried in the vacuum oven at 50° C. XRPD of that material was collected.

Form II was then prepared as a pure phase by stirring 100 mg Compound 1 Freebase Form I and 2 equivs. of in 2 mL of 1:1 THF:water (v/v). The resulting slurry was stirred at approximately 20° C. for 16 h. The slurry was then filtered and the solid was dried in the vacuum oven at about 50° C. XRPD of the dry solids was collected.

Form II can also be prepared by stirring Compound 1 Freebase Form I in THF with 4 equivs. of oxalic acid and seeding the mixture with previously prepared Form II.

Figure 29:
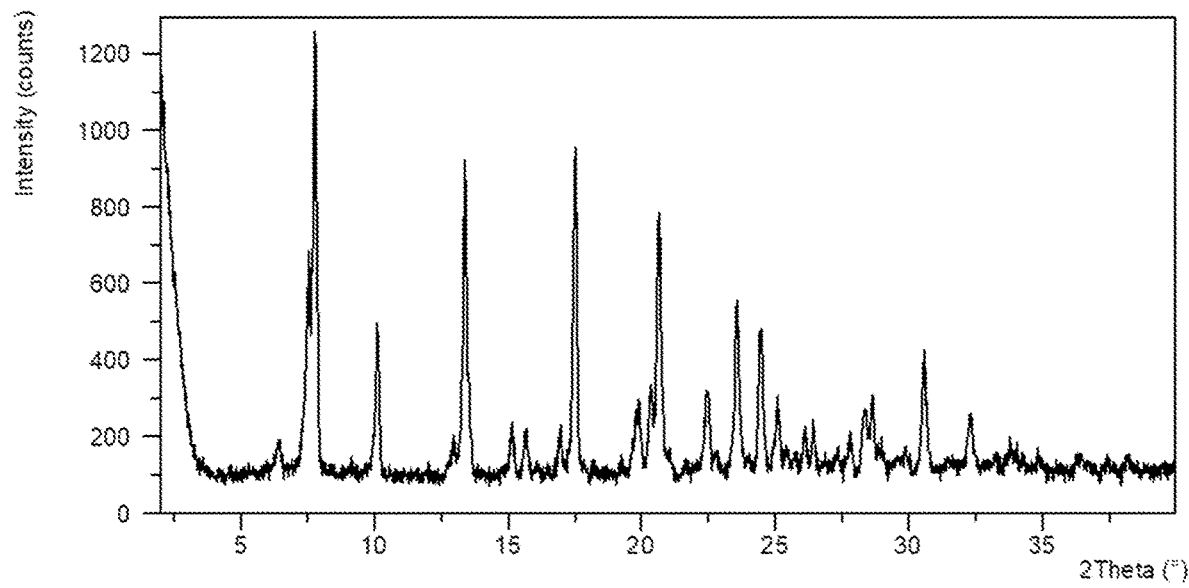
FIG. 29 shows the XRPD pattern of Compound 1 oxalate Form II.

The XRPD pattern of Compound 1 oxalate Form II is shown in FIG. 29. Table 10 summarizes the peaks in the XRPD pattern.

TABLE 10

XRPD peak list of Compound 1 oxalate Form II

| No. | Pos. [°2Th.] | Rel. Int. [%] |
|---|---|---|
| 1 | 6.4 | 7 |
| 2 | 7.6 | 49 |
| 3 | 7.8 | 100 |
| 4 | 10.1 | 32 |
| 5 | 13.0 | 9 |
| 6 | 13.4 | 72 |
| 7 | 15.1 | 11 |
| 8 | 15.7 | 10 |
| 9 | 16.9 | 10 |
| 10 | 17.5 | 69 |
| 11 | 19.9 | 16 |
| 12 | 20.4 | 20 |
| 13 | 20.7 | 60 |
| 14 | 22.5 | 19 |
| 15 | 23.6 | 38 |
| 16 | 24.5 | 33 |
| 17 | 25.1 | 15 |
| 18 | 26.1 | 9 |
| 19 | 26.4 | 10 |
| 20 | 27.8 | 8 |
| 21 | 28.4 | 14 |
| 22 | 28.7 | 16 |
| 23 | 29.9 | 4 |
| 24 | 30.6 | 28 |
| 25 | 32.4 | 12 |
| 26 | 33.8 | 5 |
| 27 | 34.9 | 3 |
| 28 | 36.5 | 3 |

Figure 30:
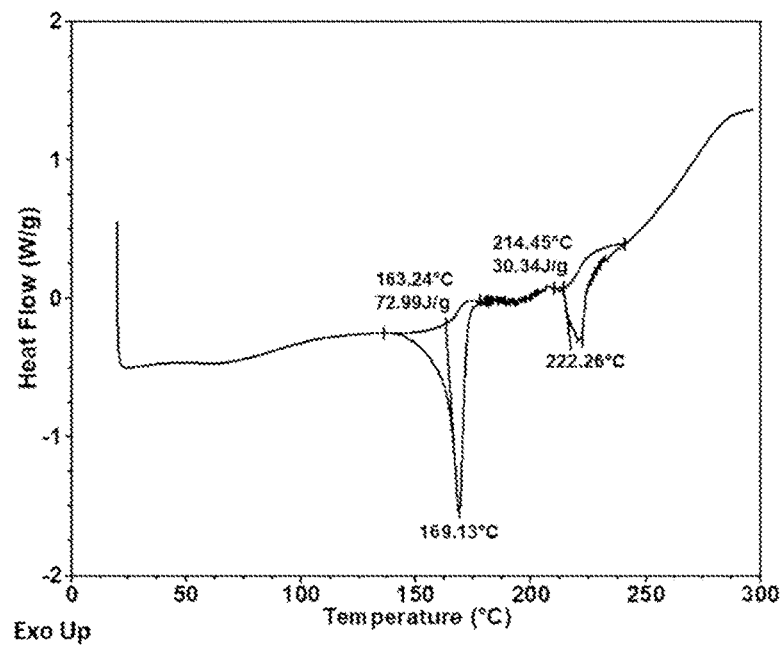
FIG. 30 shows the DSC thermogram of Compound 1 oxalate Form II.
Figure 31:
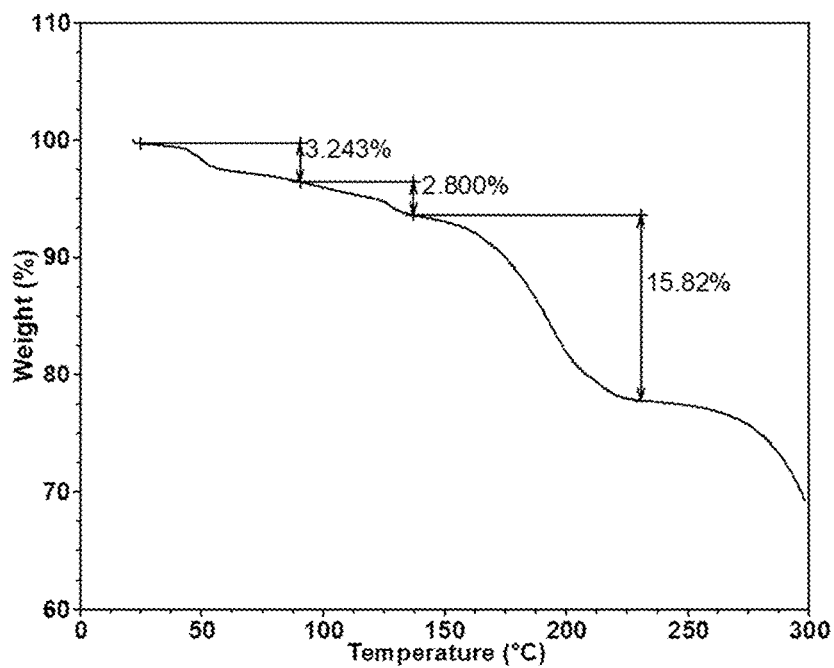
FIG. 31 shows the TGA thermogram of Compound 1 oxalate Form II.

The DSC thermogram of Compound 1 oxalate Form II is shown in FIG. 30. It has two endothermic events with onsets at approximately 163° C. and 214° C. The TGA thermogram of Compound 1 oxalate Form II is shown in FIG. 31. It shows weight losses of about 3%, 3% and 16%.

Example 5: Compound 1 Ethanedisulfonate

Figure 32:
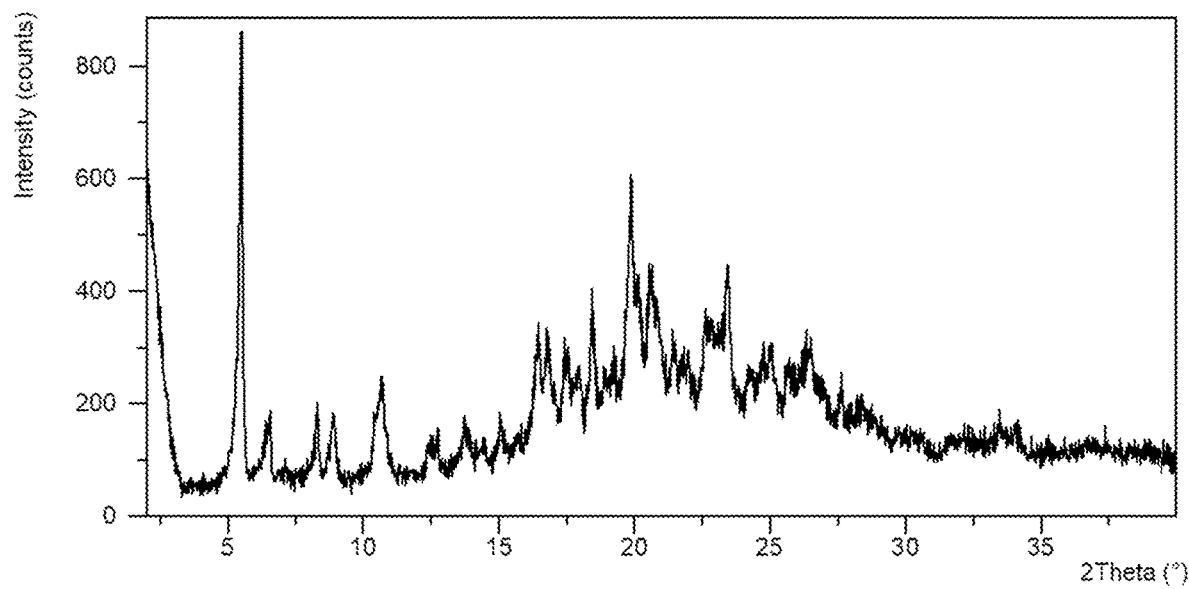
FIG. 32 shows the XRPD pattern of Compound 1 ethanedisulfonate.

Compound 1 ethanedisulfonate was first prepared by stirring about 58 mg of Compound 1 Freebase Form I and one equiv. of ethanedisulfonic acid in 0.2 mL of acetonitrile at approximately 20° C. for 2 days. The resulting slurry was then filtered and dried in the vacuum oven at about 50° C. The XRPD pattern of the solid was then obtained. FIG. 32 shows the XRPD pattern of Compound 1 ethanedisulfonate. Table 11 summarizes the peaks in the XRPD pattern.

TABLE 11

XRPD peak list of Compound 1 ethanedisulfonate

| No. | Pos. [°2Th.] | Rel. Int. [%] |
|---|---|---|
| 1 | 5.5 | 100 |
| 2 | 6.6 | 13 |
| 3 | 8.3 | 17 |
| 4 | 8.9 | 15 |
| 5 | 10.4 | 15 |
| 6 | 10.7 | 22 |
| 7 | 12.7 | 7 |
| 8 | 13.7 | 12 |
| 9 | 14.4 | 8 |
| 10 | 15.0 | 13 |
| 11 | 16.4 | 33 |
| 12 | 16.8 | 29 |
| 13 | 17.4 | 25 |
| 14 | 18.0 | 22 |
| 15 | 18.5 | 37 |
| 16 | 19.8 | 59 |
| 17 | 20.1 | 41 |
| 18 | 20.5 | 42 |
| 19 | 21.4 | 26 |
| 20 | 22.6 | 31 |
| 21 | 23.4 | 45 |
| 22 | 24.3 | 21 |
| 23 | 25.0 | 26 |
| 24 | 25.7 | 22 |
| 25 | 26.4 | 25 |
| 26 | 27.6 | 17 |
| 27 | 28.6 | 10 |
| 28 | 30.3 | 5 |
| 29 | 32.0 | 4 |
| 30 | 33.5 | 7 |
| 31 | 34.1 | 6 |

Figure 33:
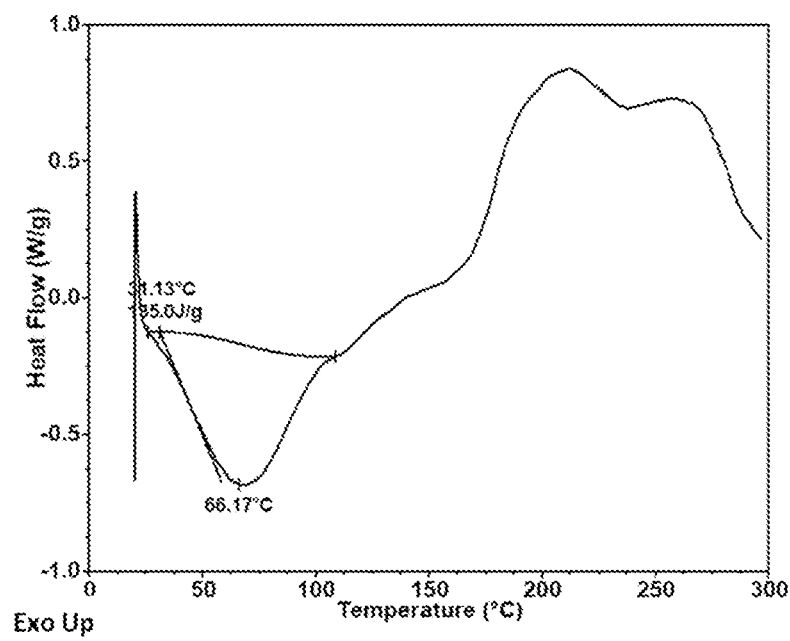
FIG. 33 shows the DSC thermogram of Compound 1 ethanedisulfonate.
Figure 34:
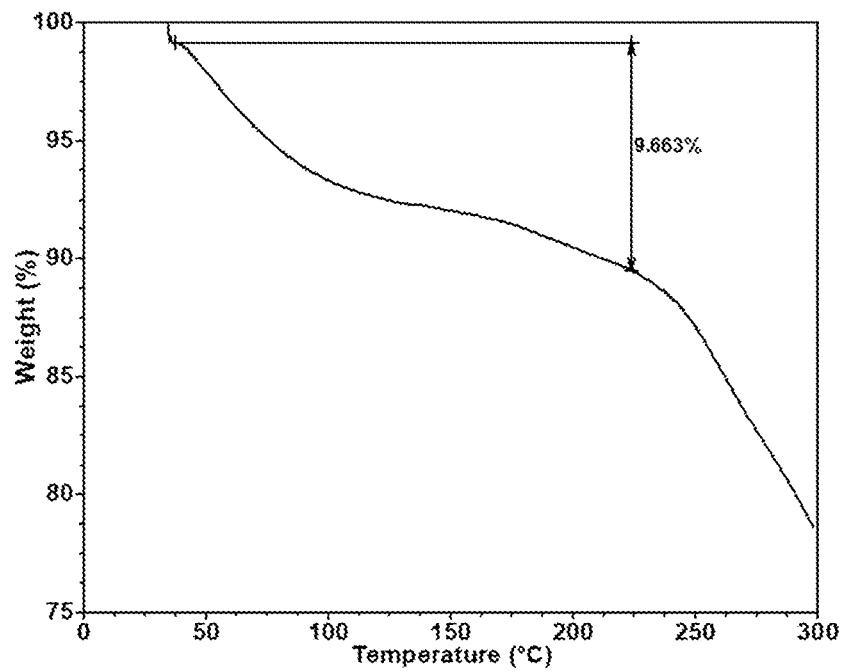
FIG. 34 shows the TGA thermogram of Compound 1 ethanedisulfonate.

The DSC thermogram of Compound 1 ethanedisulfonate is shown in FIG. 33. There is an endothermic event with an onset at 31° C. The TGA thermogram of the ethanedisulfonate is shown in FIG. 34.

Example 6: Compound 1 Maleate

Compound 1 maleate was first prepared by stirring about 60 mg of Compound 1 Freebase Form I and one equiv. of maleic acid to in 0.2 mL of acetonitrile. The slurry was stirred at approximately 20° C. for about 16 h. The slurry was then centrifuged and the XRPD of the wet solid was collected. The wet-cake was dried in the vacuum oven at approximately 50° C., and the XRPD pattern of the dry solid was obtained.

Figure 35:
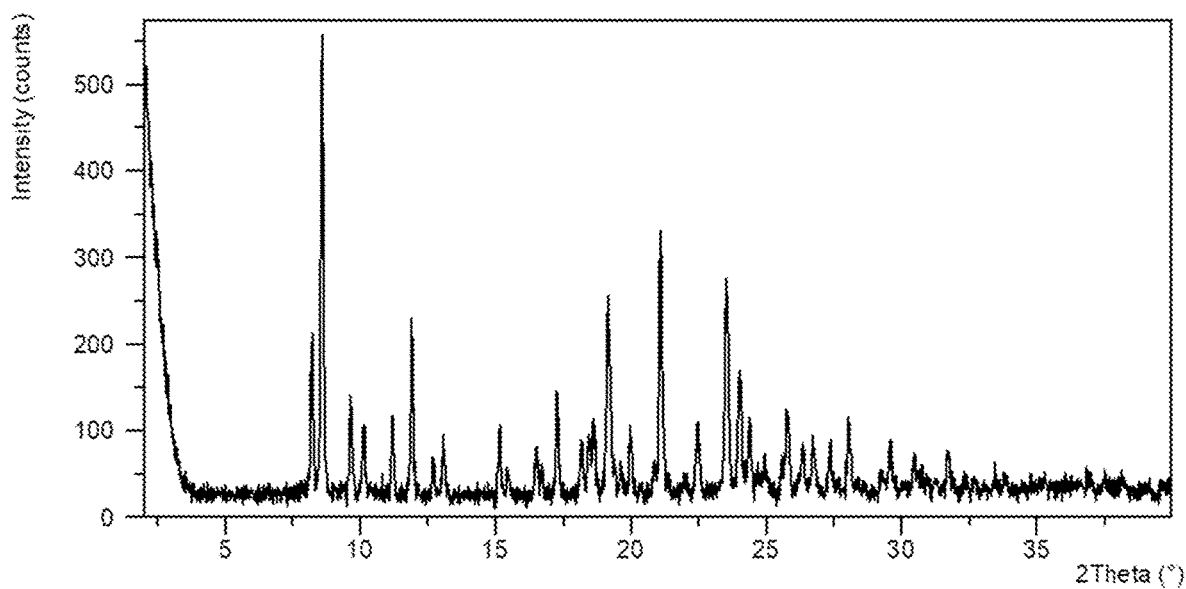
FIG. 35 shows the XRPD pattern of Compound 1 maleate.

FIG. 35 shows the XRPD pattern of Compound 1 maleate. Table 12 summarizes the peaks in the XRPD pattern.

TABLE 12

XRPD peak list of Compound 1 maleate

| No. | Pos. [°2Th.] | Rel. Int. [%] |
|---|---|---|
| 1 | 8.2 | 32 |
| 2 | 8.6 | 100 |
| 3 | 9.6 | 19 |
| 4 | 10.1 | 15 |
| 5 | 11.2 | 16 |
| 6 | 11.9 | 35 |
| 7 | 12.7 | 7 |
| 8 | 13.1 | 11 |
| 9 | 15.1 | 14 |
| 10 | 16.5 | 9 |
| 11 | 17.3 | 21 |
| 12 | 18.2 | 12 |
| 13 | 18.4 | 10 |
| 14 | 18.6 | 15 |
| 15 | 19.1 | 41 |
| 16 | 20.0 | 15 |
| 17 | 21.1 | 57 |
| 18 | 22.5 | 15 |
| 19 | 23.5 | 46 |
| 20 | 24.0 | 27 |
| 21 | 24.4 | 15 |
| 22 | 25.8 | 18 |
| 23 | 26.4 | 9 |
| 24 | 26.7 | 11 |
| 25 | 27.4 | 9 |
| 26 | 28.1 | 14 |
| 27 | 29.6 | 12 |
| 28 | 30.5 | 7 |
| 29 | 31.7 | 8 |

Figure 36:
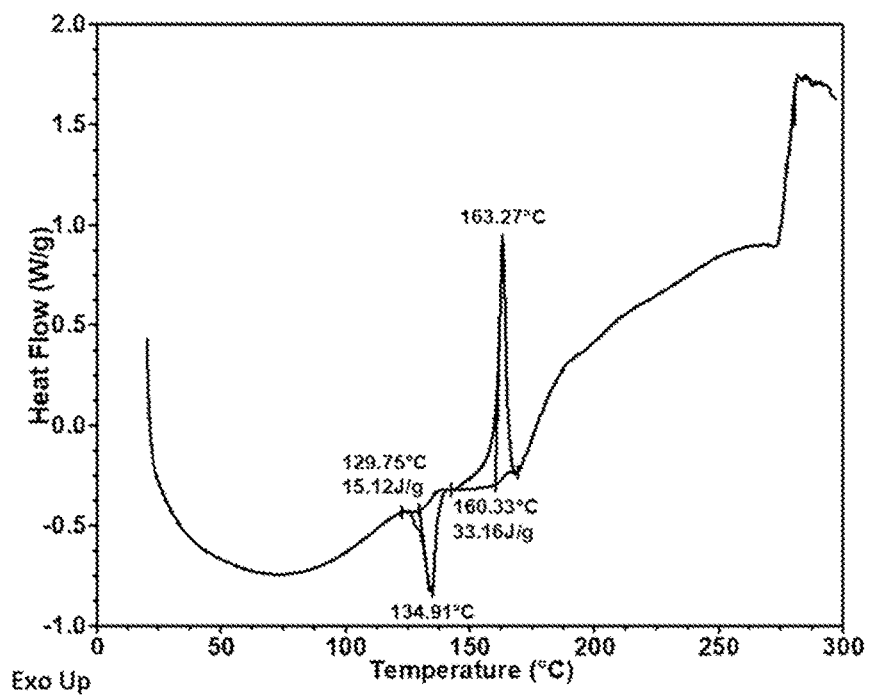
FIG. 36 shows the DSC thermogram of Compound 1 maleate.
Figure 37:
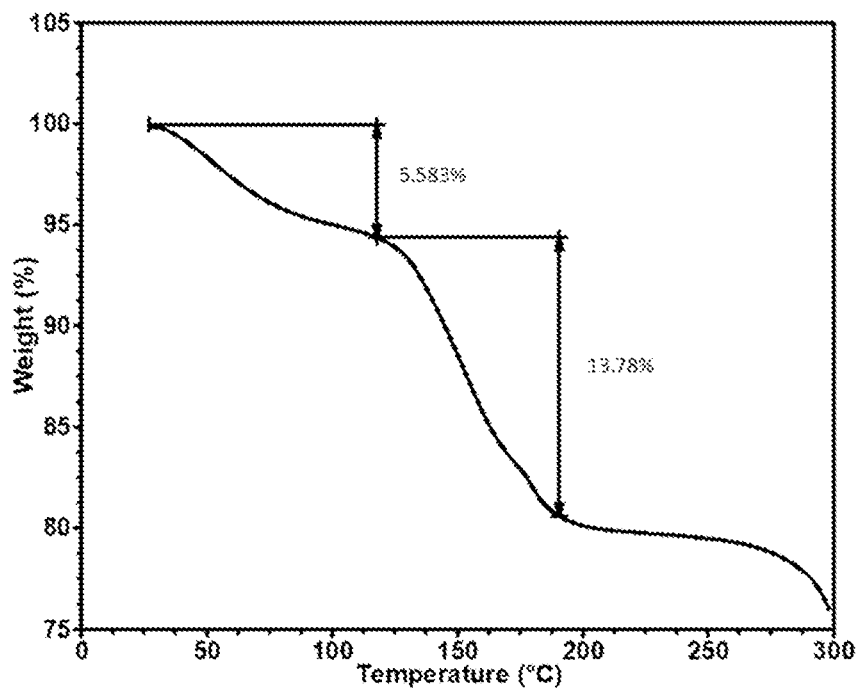
FIG. 37 shows the TGA thermogram of Compound 1 maleate.

The DSC thermogram of the maleate is shown in FIG. 36. There is an endothermic event with an onset at about 130° C. and an exothermic event with an onset at about 160° C. The TGA thermogram of Compound 1 maleate is shown in FIG. 37. There are weight losses of approximately 5.6% and 13.8%.

Example 7: Compound 1 Camsylate

Compound 1 Camsylate Form I

Figure 38:
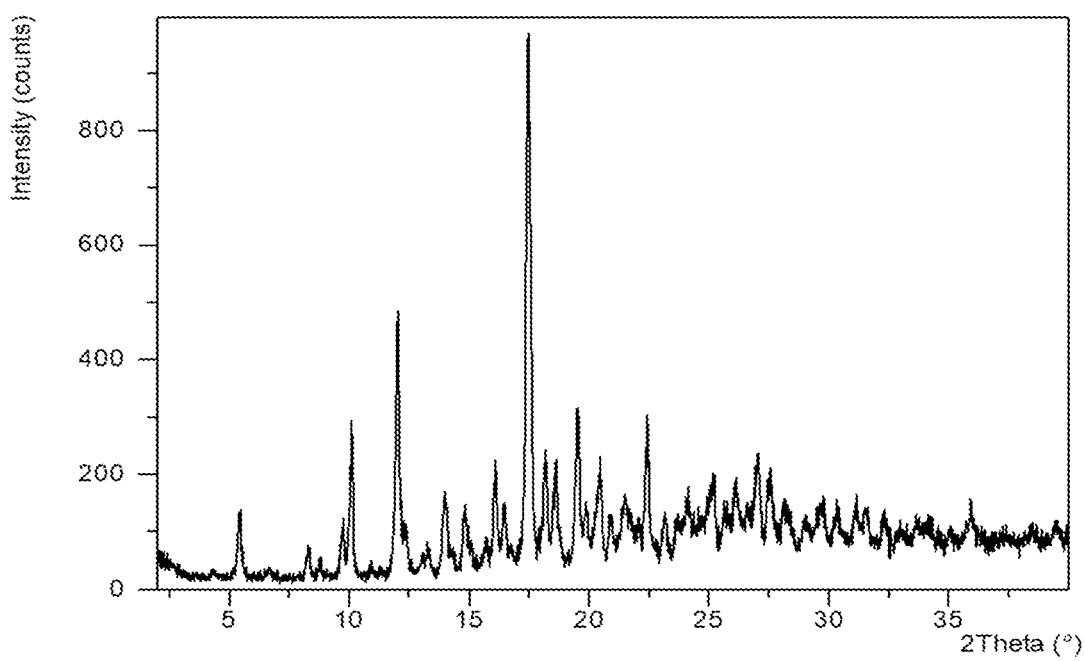
FIG. 38 shows the XRPD pattern of Compound 1 camsylate Form I.

Compound 1 camsylate Form I was prepared by mixing 100 mg Compound 1 free base with 1 equiv. of (+)-camphor-10-sulfonic acid in 1 mL of isopropanol. The sample was heated to about 90° C. briefly in a sealed vial and then cooled to 22° C. The sample was sonicated for about 1 minute, and stirred for 1 h. The solids were isolated by centrifuge and dried at 50° C. for 1 h. The XRPD pattern of Compound 1 camsylate Form I is shown in FIG. 38. Table 13 summarizes the peaks in the XRPD pattern.

TABLE 13

XRPD peak lists of Compound 1 camsylate Form I

| No. | Pos. [°2Th.] | Rel. Int. [%] |
|---|---|---|
| 1 | 5.4 | 12 |
| 2 | 6.7 | 2 |
| 3 | 8.3 | 5 |
| 4 | 8.8 | 2 |
| 5 | 9.7 | 10 |
| 6 | 10.1 | 28 |
| 7 | 12.0 | 50 |
| 8 | 12.4 | 8 |
| 9 | 13.3 | 4 |
| 10 | 14.0 | 13 |
| 11 | 14.8 | 10 |
| 12 | 16.1 | 15 |
| 13 | 16.5 | 9 |
| 14 | 17.5 | 100 |
| 15 | 18.2 | 18 |
| 16 | 18.6 | 16 |
| 17 | 19.5 | 26 |
| 18 | 19.9 | 8 |
| 19 | 20.5 | 14 |
| 20 | 20.9 | 5 |
| 21 | 21.5 | 10 |
| 22 | 22.4 | 25 |
| 23 | 23.2 | 7 |
| 24 | 24.1 | 9 |
| 25 | 25.2 | 11 |
| 26 | 26.1 | 9 |
| 27 | 27.1 | 16 |
| 28 | 27.5 | 10 |
| 29 | 28.2 | 6 |
| 30 | 29.7 | 7 |
| 31 | 30.3 | 5 |
| 32 | 31.6 | 6 |
| 33 | 36.0 | 7 |

Form I can also be isolated by desolvating solvates such as EtOH solvate, IPA solvate, and acetone solvate, and THF solvate.

Figure 39:
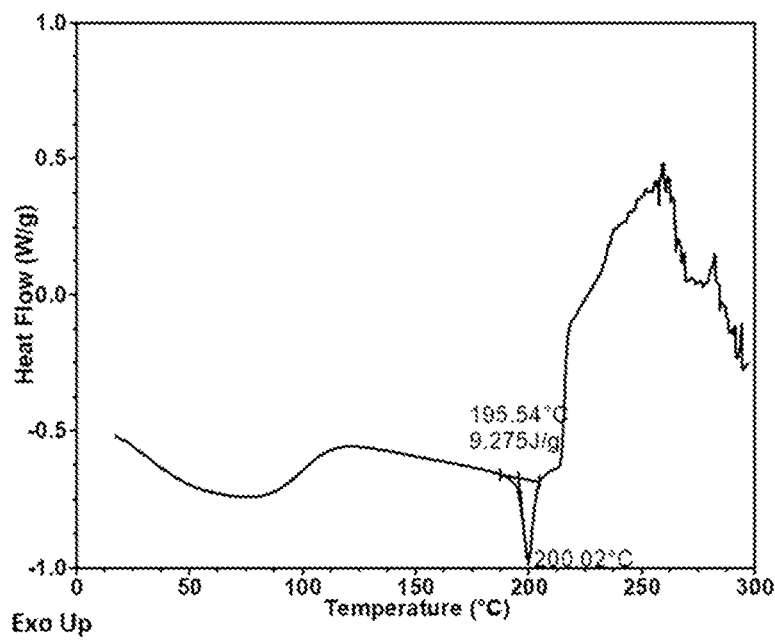
FIG. 39 shows the DSC thermogram of Compound 1 camsylate Form I.
Figure 40:
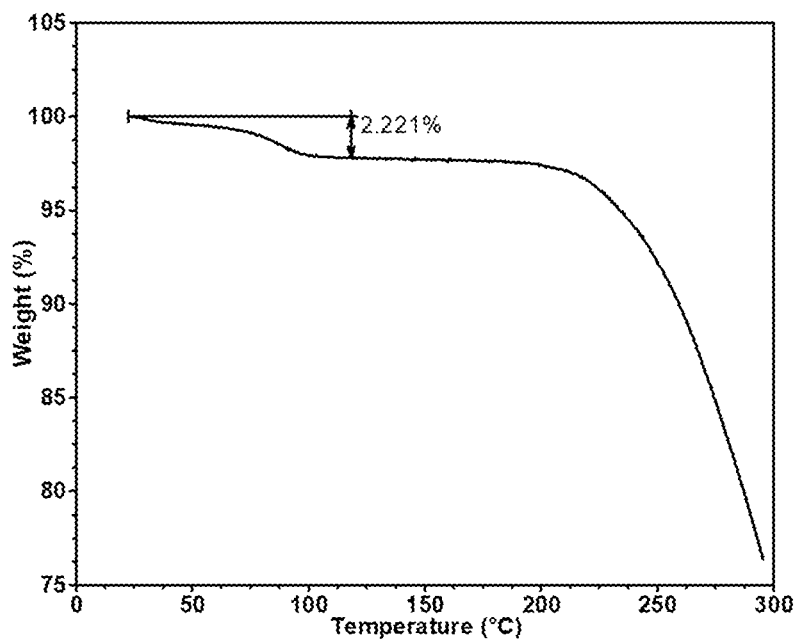
FIG. 40 shows the TGA thermogram of Compound 1 camsylate Form I.

The DSC thermogram of Compound 1 camsylate Form I is shown in FIG. 39. As is shown, there is a broad endotherm between ambient temperature and about 120° C., followed by a melting onset at about 196° C. The TGA thermogram of Compound 1 camsylate Form I is shown in FIG. 40. There is about a 2% weight loss at a temperature below 100° C.

Compound 1 Camsylate Form II

Figure 41:
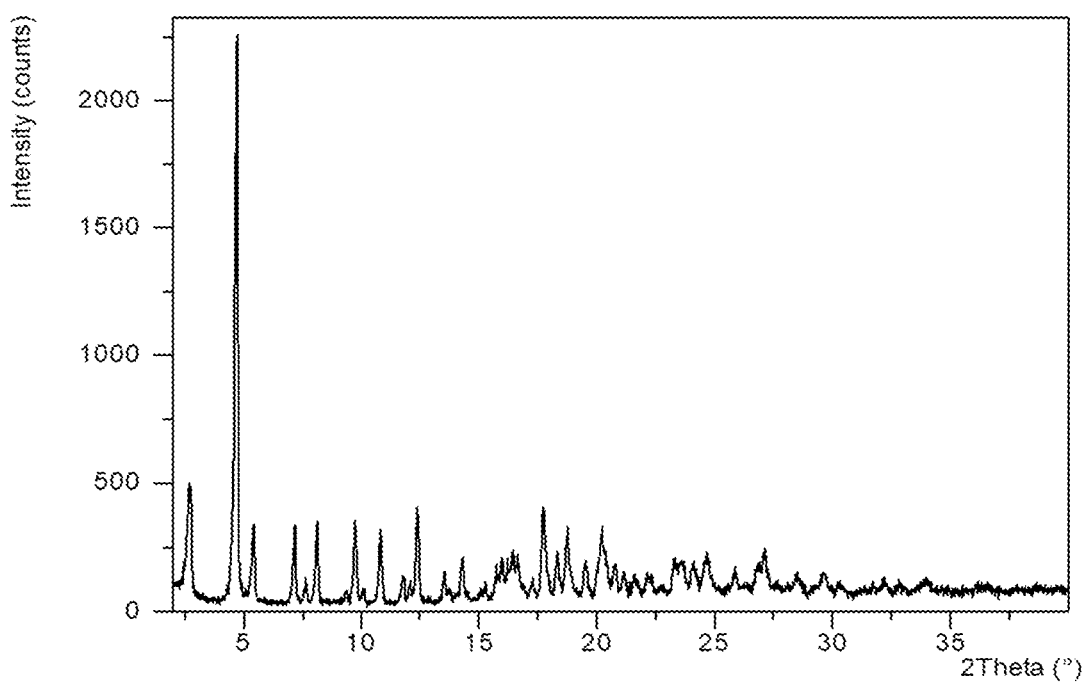
FIG. 41 shows the XRPD pattern of Compound 1 camsylate Form II.

Compound 1 camsylate Form II was prepared by stirring Compound 1 camsylate Form I at about 22° C. in solvents such as MEK, 2-MeTHF, MTBE, methanol/IPE mixture, MIBK, DCM/heptane mixture, EtOAc, IPAc, toluene for at least 1 day to form solvates of Compound 1 camsylate, and then filtering and drying them in the vacuum oven at 50° C. for 1 h. The XRPD pattern of Compound 1 camsylate Form II is shown in FIG. 41. Table 14 summarizes the peaks in the XRPD pattern.

TABLE 14

XRPD peak lists of Compound 1 camsylate Form II

| No. | Pos. [°2Th.] | Rel. Int. [%] |
|---|---|---|
| 1 | 2.8 | 18 |
| 2 | 4.7 | 100 |
| 3 | 5.4 | 13 |
| 4 | 7.2 | 13 |
| 5 | 7.6 | 3 |
| 6 | 8.1 | 15 |
| 7 | 9.8 | 12 |
| 8 | 10.8 | 13 |
| 9 | 11.8 | 4 |
| 10 | 12.1 | 3 |
| 11 | 12.4 | 16 |
| 12 | 13.5 | 4 |
| 13 | 14.3 | 7 |
| 14 | 15.7 | 4 |
| 15 | 16.0 | 6 |
| 16 | 16.4 | 8 |
| 17 | 16.7 | 6 |
| 18 | 17.7 | 15 |
| 19 | 18.3 | 7 |
| 20 | 18.7 | 10 |
| 21 | 19.5 | 5 |
| 22 | 20.2 | 11 |
| 23 | 20.8 | 4 |
| 24 | 21.1 | 3 |

TABLE 14-continued

XRPD peak lists of Compound 1 camsylate Form II

| No. | Pos. [°2Th.] | Rel. Int. [%] |
|---|---|---|
| 25 | 22.2 | 3 |
| 26 | 23.3 | 4 |
| 27 | 23.6 | 5 |
| 28 | 24.1 | 4 |
| 29 | 24.7 | 5 |
| 30 | 25.9 | 3 |
| 31 | 27.1 | 7 |
| 32 | 29.6 | 3 |

Figure 42:
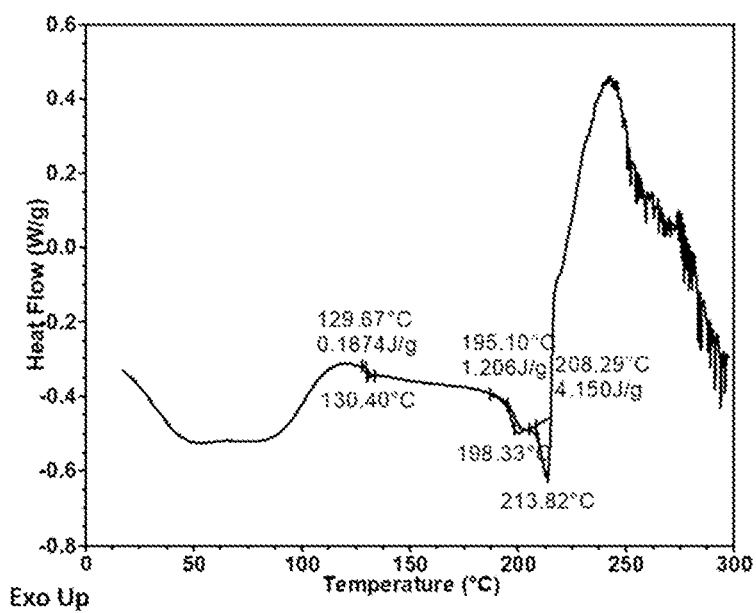
FIG. 42 shows the DSC thermogram of Compound 1 camsylate Form II.
Figure 43:
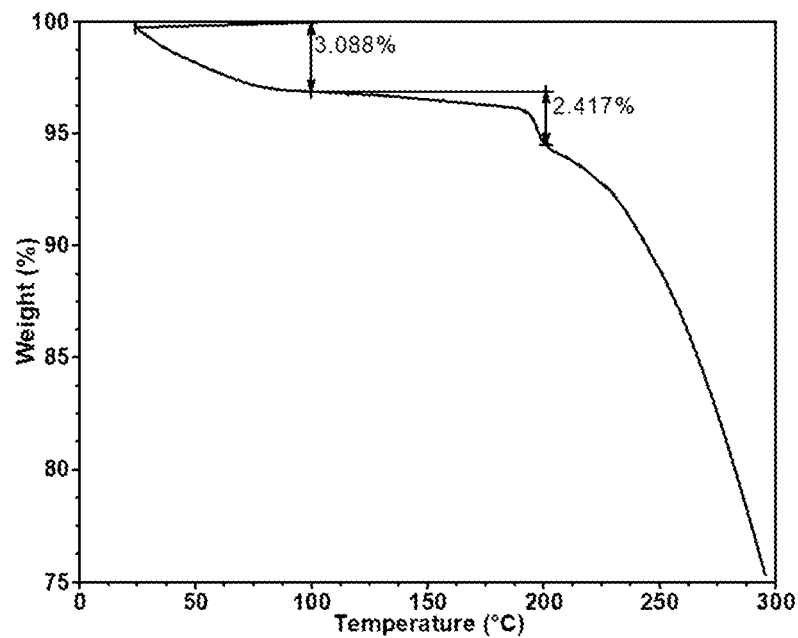
FIG. 43 shows the TGA thermogram of Compound 1 camsylate Form II.

The DSC thermogram of Compound 1 camsylate Form II is shown in FIG. 42. As shown, there is a broad endotherm between ambient temperature and about 120° C., followed by endothermic events at about 130, 198, and 214° C., respectively. The TGA thermogram of Compound 1 camsylate Form II is shown in FIG. 43. There are weight losses of about 3% at a temperature below 100° C. and of about 2.4% at a temperature of about 198° C.

Compound 1 Camsylate Form III

Figure 44:
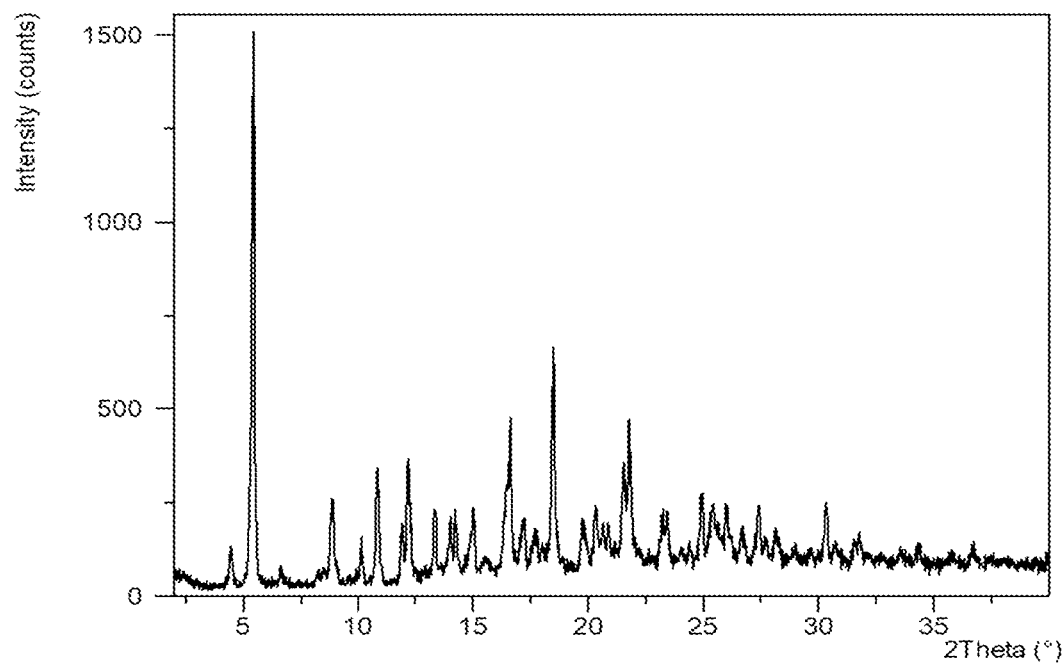
FIG. 44 shows the XRPD pattern of Compound 1 camsylate Form III.

Compound 1 camsylate Form III was prepared by stirring Compound 1 camsylate Form I at about 22° C. in acetonitrile for 1 day, and filtering and drying the solid at 70° C. It is an unsolvated form. The XRPD pattern of Compound 1 camsylate Form III is shown in FIG. 44. Table 15 summarizes the peaks in the XRPD pattern.

TABLE 15

XRPD peak list of Compound 1 camsylate Form III

| No. | Pos. [°2Th.] | Rel. Int. [%] |
|---|---|---|
| 1 | 4.5 | 7 |
| 2 | 5.5 | 100 |
| 3 | 6.6 | 3 |
| 4 | 8.9 | 15 |
| 5 | 10.1 | 9 |
| 6 | 10.9 | 21 |
| 7 | 11.9 | 10 |
| 8 | 12.2 | 22 |
| 9 | 13.3 | 11 |
| 10 | 14.0 | 10 |
| 11 | 14.2 | 10 |
| 12 | 15.0 | 11 |
| 13 | 16.6 | 22 |
| 14 | 17.2 | 7 |
| 15 | 17.7 | 5 |
| 16 | 18.5 | 38 |
| 17 | 19.7 | 8 |
| 18 | 20.3 | 9 |
| 19 | 20.8 | 5 |
| 20 | 21.5 | 17 |
| 21 | 21.8 | 21 |
| 22 | 23.2 | 8 |
| 23 | 23.4 | 9 |
| 24 | 24.9 | 11 |
| 25 | 25.4 | 9 |
| 26 | 26.0 | 9 |
| 27 | 26.7 | 5 |
| 28 | 27.4 | 9 |
| 29 | 28.2 | 4 |
| 30 | 30.3 | 11 |
| 31 | 31.8 | 4 |
| 32 | 34.4 | 3 |

Figure 45:
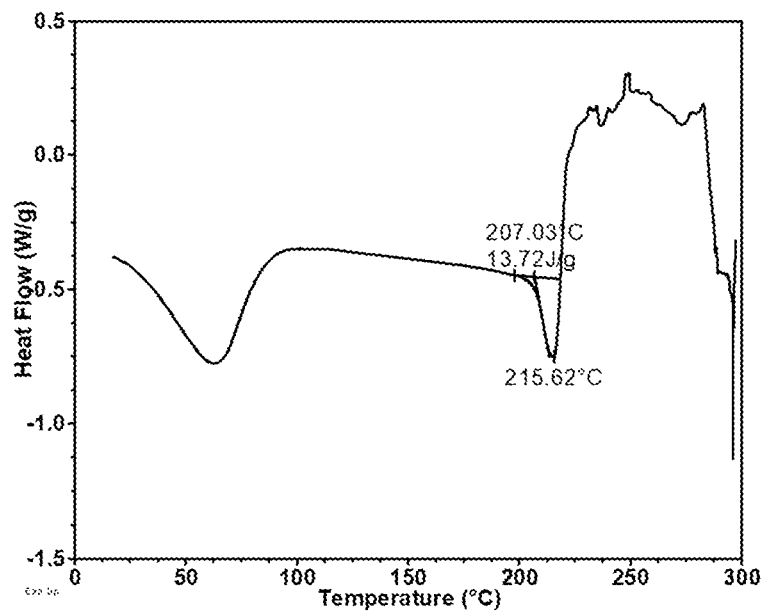
FIG. 45 shows the DSC thermogram of Compound 1 camsylate Form III.
Figure 46:
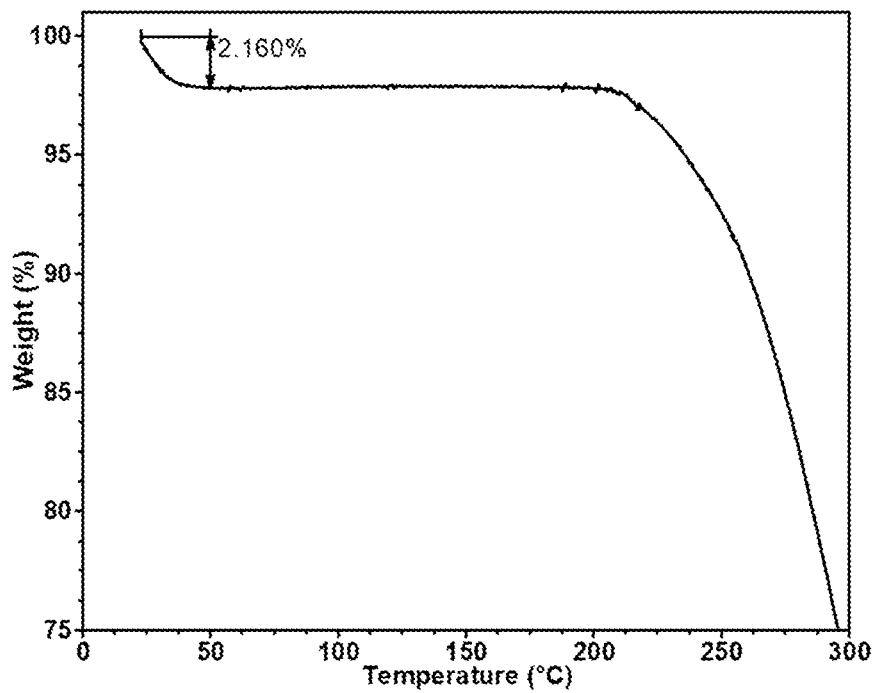
FIG. 46 shows the TGA thermogram of Compound 1 camsylate Form III.

The DSC thermogram of Compound 1 camsylate Form III is shown in FIG. 45. There is a broad endotherm between ambient temperature and about 100° C., followed by a melting endotherm with an onset at about 207° C. The TGA thermogram of Compound 1 camsylate Form III is shown in FIG. 46. There is an approximately 2% weight loss at a temperature below 50° C.

Example 8. Compound 1 Besylate

Compound 1 Besylate Hydrate A

Figure 47:
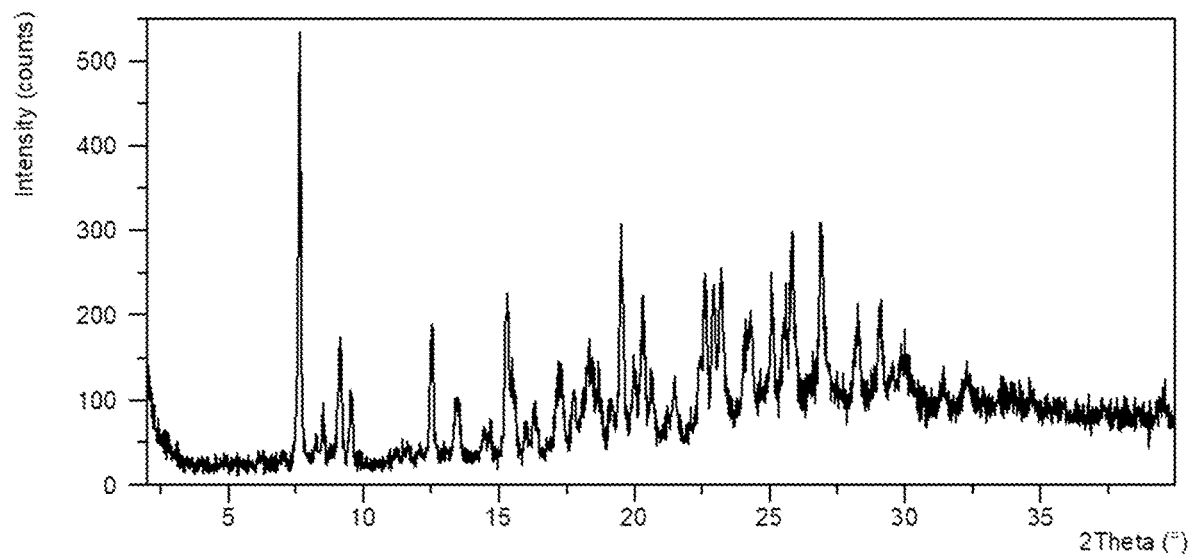
FIG. 47 shows the XRPD pattern of Compound 1 besylate Hydrate A.

Compound 1 besylate Hydrate A was first prepared by stirring approximately 50 mg of a mixture composed of Compound 1 freebase and two equivalents of benzenesulfonic acid in about 5 mL of water for about 4 days. The slurry was then centrifuged and the XRPD pattern of the wet solid, besylate Hydrate A, was collected. FIG. 47 is the XRPD pattern of Compound 1 besylate Hydrate A. Table 16 summarizes the peaks in the XRPD pattern.

TABLE 16

XRPD peaks list of Compound 1 besylate Hydrate A

| No. | Pos. [°2Th.] | Rel. Int. [%] |
|---|---|---|
| 1 | 7.7 | 100 |
| 2 | 8.5 | 12 |
| 3 | 9.2 | 27 |
| 4 | 9.6 | 18 |
| 5 | 12.5 | 30 |
| 6 | 13.5 | 14 |
| 7 | 14.7 | 8 |
| 8 | 15.3 | 36 |
| 9 | 16.3 | 10 |
| 10 | 17.3 | 19 |
| 11 | 17.8 | 13 |
| 12 | 18.4 | 21 |
| 13 | 18.7 | 16 |
| 14 | 19.2 | 9 |
| 15 | 19.5 | 41 |
| 16 | 20.0 | 18 |
| 17 | 20.3 | 35 |
| 18 | 20.7 | 15 |
| 19 | 21.5 | 13 |
| 20 | 22.6 | 36 |
| 21 | 22.9 | 35 |
| 22 | 23.2 | 38 |
| 23 | 24.3 | 25 |
| 24 | 25.1 | 34 |
| 25 | 25.6 | 26 |
| 26 | 25.8 | 48 |
| 27 | 26.9 | 50 |
| 28 | 28.3 | 23 |
| 29 | 29.1 | 24 |
| 30 | 30.0 | 13 |
| 31 | 31.4 | 6 |
| 32 | 32.3 | 7 |

Compound 1 Besylate Material A

Figure 48:
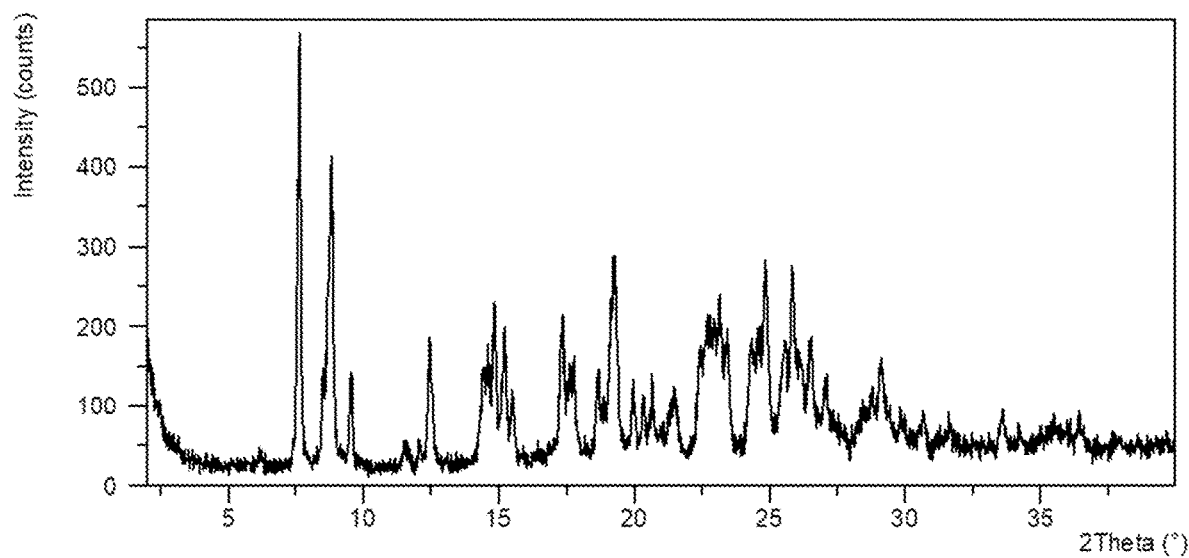
FIG. 48 shows the XRPD pattern of Compound 1 besylate Material A.

Compound 1 besylate Material A was prepared by drying besylate Hydrate A in the vacuum oven at 40° C. with a small nitrogen purge for about 16 h. The XRPD pattern of Compound 1 besylate Material A is shown in FIG. 48. Table 17 summarizes the peaks in the XRPD pattern.

TABLE 17

XRPD peaks list of Compound 1 besylate Material A

| No. | Pos. [°2Th.] | Rel. Int. [%] |
|---|---|---|
| 1 | 7.6 | 100 |
| 2 | 8.5 | 20 |
| 3 | 8.8 | 72 |
| 4 | 9.6 | 22 |
| 5 | 11.6 | 5 |
| 6 | 12.4 | 27 |
| 7 | 14.4 | 22 |

TABLE 17-continued

XRPD peaks list of Compound 1 besylate Material A

| No. | Pos. [°2Th.] | Rel. Int. [%] |
|---|---|---|
| 8 | 14.8 | 38 |
| 9 | 15.2 | 27 |
| 10 | 15.5 | 16 |
| 11 | 17.3 | 32 |
| 12 | 17.7 | 20 |
| 13 | 18.7 | 19 |
| 14 | 19.3 | 46 |
| 15 | 20.0 | 17 |
| 16 | 20.4 | 15 |
| 17 | 20.7 | 17 |
| 18 | 21.5 | 15 |
| 19 | 22.4 | 24 |
| 20 | 23.2 | 35 |
| 21 | 23.4 | 28 |
| 22 | 24.3 | 26 |
| 23 | 24.9 | 42 |
| 24 | 25.8 | 43 |
| 25 | 26.5 | 26 |
| 26 | 27.1 | 18 |
| 27 | 29.1 | 22 |
| 28 | 30.7 | 8 |
| 29 | 31.7 | 5 |
| 30 | 33.6 | 8 |
| 31 | 36.5 | 6 |

Figure 49:
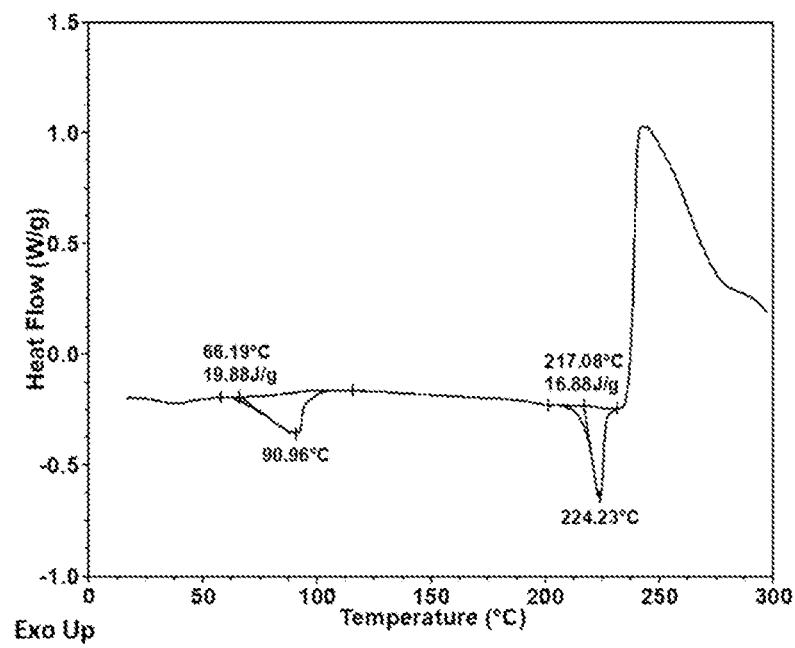
FIG. 49 shows the DSC thermogram of Compound 1 besylate Material A.
Figure 50:
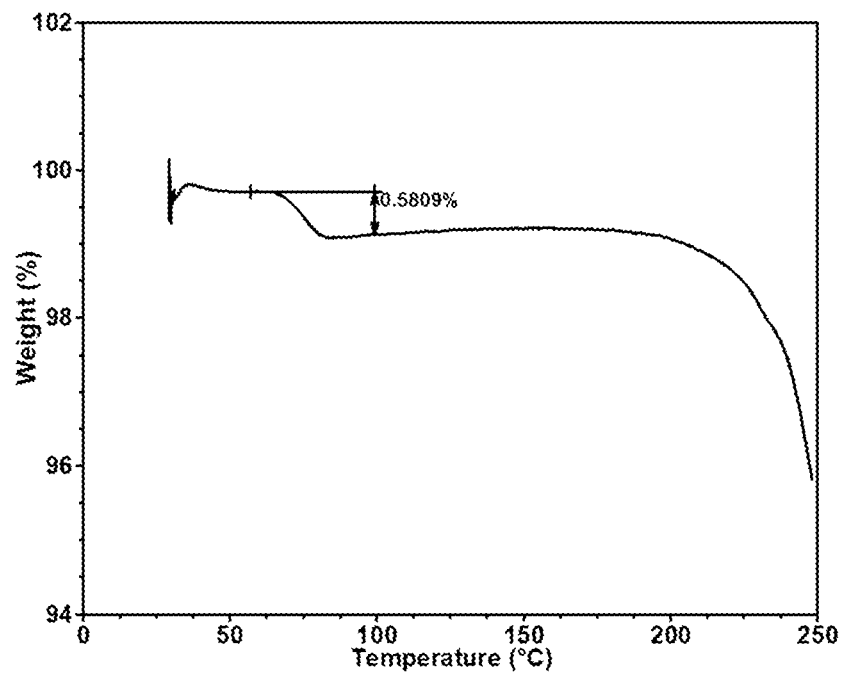
FIG. 50 shows the TGA thermogram of Compound 1 besylate Material A.

The DSC thermogram of Compound 1 besylate Material A is shown in FIG. 49. There are two endothermic events with onsets at approximately 66° C. and 217° C. The TGA thermogram of Compound 1 besylate Material A is shown in FIG. 50.

Compound 1 Besylate Ethanol Solvate A

Compound 1 ethanol solvate A was first prepared by stirring approximately 50 mg of mixture composed of Compound 1 freebase and two equivs. of benzenesulfonic acid in about 5 mL of ethanol for about 4 days. The slurry was then filtered and XRPD of the wet cake was obtained. Compound 1 besylate Ethanol solvate A is a labile solvate. The XRPD pattern of Compound 1 besylate ethanol solvate A is presented in FIG. 51. Table 18 summarizes the peaks in the XRPD pattern.

TABLE 18

XRPD peaks list of Compound 1 besylate ethanol solvate A

| No. | Pos. [°2Th.] | Rel. Int. [%] |
|---|---|---|
| 1 | 7.3 | 100 |
| 2 | 7.7 | 19 |
| 3 | 8.8 | 9 |
| 4 | 9.1 | 34 |
| 5 | 9.8 | 15 |
| 6 | 10.0 | 30 |
| 7 | 10.4 | 11 |
| 8 | 11.8 | 7 |
| 9 | 12.4 | 6 |
| 10 | 13.5 | 15 |
| 11 | 14.4 | 14 |
| 12 | 14.8 | 60 |
| 13 | 15.7 | 8 |
| 14 | 16.1 | 6 |
| 15 | 17.1 | 13 |
| 16 | 17.7 | 19 |
| 17 | 18.1 | 84 |
| 18 | 19.6 | 34 |
| 19 | 20.0 | 20 |
| 20 | 20.7 | 7 |
| 21 | 21.3 | 41 |
| 22 | 21.7 | 31 |
| 23 | 22.0 | 19 |
| 24 | 22.7 | 22 |

TABLE 18-continued

XRPD peaks list of Compound 1 besylate ethanol solvate A

| No. | Pos. [°2Th.] | Rel. Int. [%] |
|---|---|---|
| 25 | 23.5 | 15 |
| 26 | 24.4 | 38 |
| 27 | 25.2 | 24 |
| 28 | 26.0 | 22 |
| 29 | 26.4 | 19 |
| 30 | 27.1 | 31 |

Besylate Form I

Compound 1 besylate Form I was first prepared by stirring approximately 50 mg of Compound 1 freebase Form I and approximately two equivs. of benzenesulfonic acid in about 5 mL of methanol for about 4 days. The resulting slurry was then filtered and dried in the vacuum oven at 40° C. with a small nitrogen purge for about 16 h, and XRPD of the dry solid was obtained.

Form I was also prepared by drying Compound 1 besylate ethanol solvate A in the vacuum oven at 40° C. with a small nitrogen purge for about 16 h. The XRPD pattern of Compound 1 besylate Form I is shown in FIG. 51. Table 19 summarizes the peaks in the XRPD pattern.

TABLE 19

XRPD peaks list of Compound 1 besylate Form I

| No. | Pos. [°2Th.] | Rel. Int. [%] |
|---|---|---|
| 1 | 6.8 | 100 |
| 2 | 8.3 | 25 |
| 3 | 8.6 | 22 |
| 4 | 9.9 | 16 |
| 6 | 13.6 | 11 |
| 7 | 13.9 | 20 |
| 8 | 14.5 | 65 |
| 9 | 15.5 | 45 |
| 10 | 16.2 | 32 |
| 11 | 16.5 | 13 |
| 13 | 17.8 | 75 |
| 14 | 18.0 | 18 |
| 17 | 19.6 | 14 |
| 18 | 19.9 | 31 |
| 19 | 20.3 | 22 |
| 20 | 20.9 | 10 |
| 21 | 21.3 | 12 |
| 22 | 22.3 | 13 |
| 23 | 22.8 | 13 |
| 24 | 23.9 | 10 |
| 25 | 24.6 | 45 |
| 26 | 25.4 | 10 |
| 27 | 25.6 | 11 |
| 28 | 26.1 | 14 |
| 29 | 26.5 | 10 |
| 30 | 27.2 | 62 |
| 31 | 29.8 | 17 |
| 32 | 33.4 | 11 |
| 33 | 34.5 | 9 |

Figure 53:
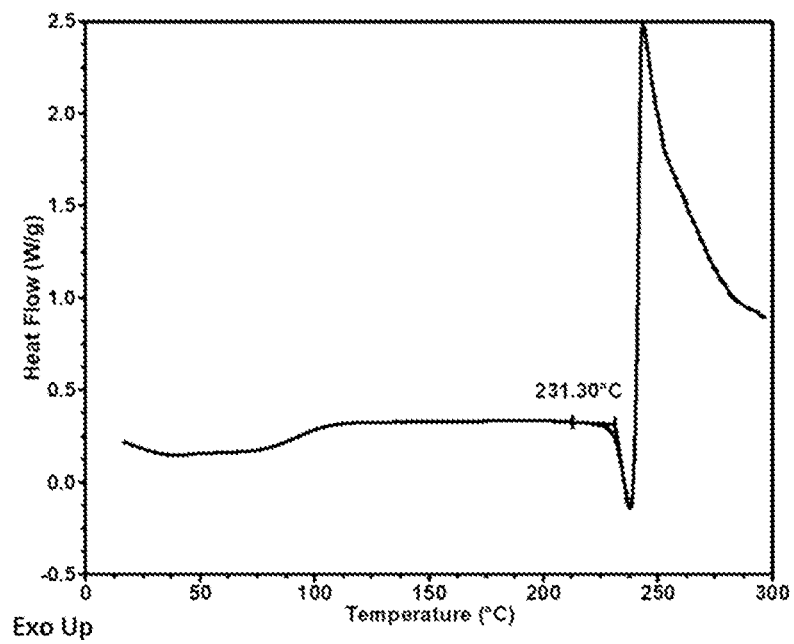
FIG. 53 shows the DSC thermogram of Compound 1 besylate Form I.
Figure 54:
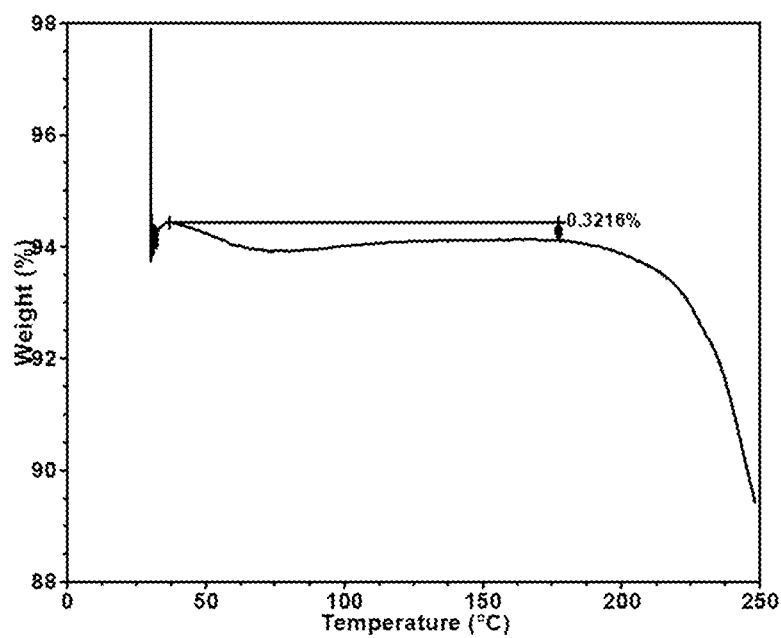
FIG. 54 shows the TGA thermogram of Compound 1 besylate Form I.

The DSC thermogram of Compound 1 besylate Form I is shown in FIG. 53. There is an endothermic event with an onset around 230° C. The TGA thermogram of Compound 1 besylate Form I is shown in FIG. 54.

Besylate Form II

Compound 1 besylate Form II was first prepared by charging about 3 g of Compound 1 freebase Form I and 10 volumes of acetonitrile in a reactor. The temperature of the mixture was adjusted to about 20° C. and 2 equivs. of benzenesulfonic acid were then added. The temperature was then heated to 50° C. for about 30 min to allow all the solids to dissolve, and then cooled to about 20° C. over approximately 1 hour. The resulting slurry was stirred for about 48 hours. The mixture was then filtered, and the wet cake was rinsed with 5 volumes of acetonitrile. The solids were dried at 50° C.

Figure 55:
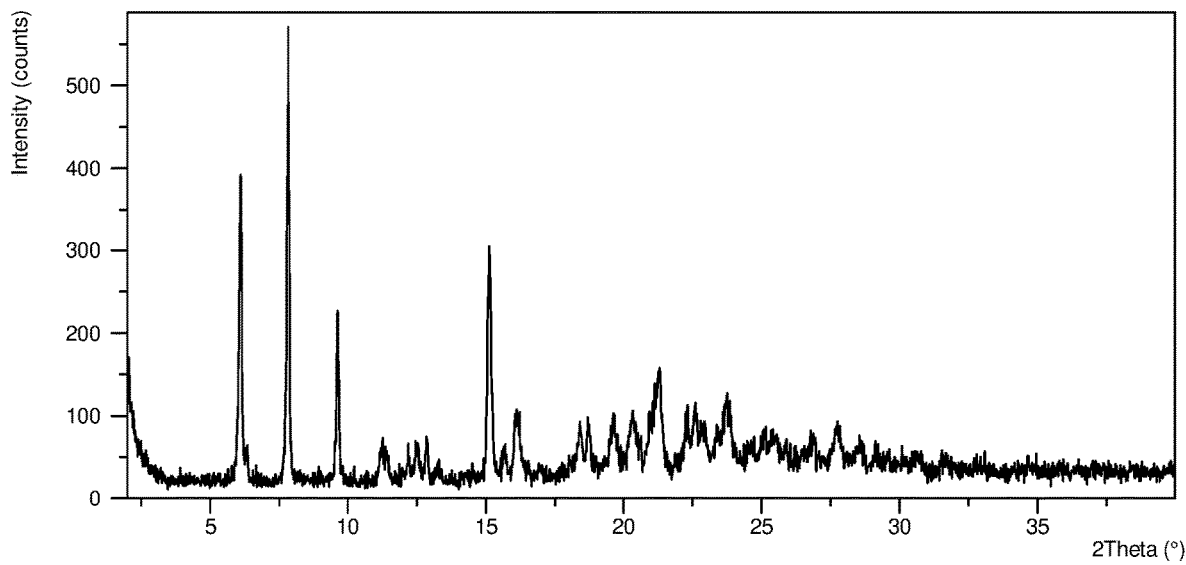
FIG. 55 shows the XRPD pattern of Compound 1 besylate Form II.

Compound 1 besylate Form II was also prepared in solvent mixture of acetonitrile and methanol. The XRPD pattern of Compound 1 besylate Form II is shown in FIG. 55. Table 20 summarizes the peaks in the XRPD pattern.

TABLE 20

XRPD peaks list of Compound 1 besylate Form II

| No. | Pos. [°2Th.] | Rel. Int. [%] |
|---|---|---|
| 1 | 6.1 | 66 |
| 2 | 7.8 | 100 |
| 3 | 9.6 | 32 |
| 4 | 11.3 | 7 |
| 5 | 12.1 | 5 |
| 6 | 12.5 | 8 |
| 7 | 12.9 | 9 |
| 8 | 15.1 | 50 |
| 9 | 16.1 | 14 |
| 10 | 18.4 | 11 |
| 11 | 18.7 | 11 |
| 12 | 19.6 | 13 |
| 13 | 20.3 | 12 |
| 14 | 20.9 | 13 |
| 15 | 21.3 | 22 |
| 16 | 22.3 | 11 |
| 17 | 22.6 | 14 |
| 18 | 22.9 | 8 |
| 19 | 23.4 | 9 |
| 20 | 23.7 | 15 |
| 21 | 24.6 | 6 |
| 22 | 25.3 | 6 |
| 23 | 26.8 | 6 |
| 24 | 27.7 | 8 |
| 25 | 28.6 | 5 |

Figure 56:
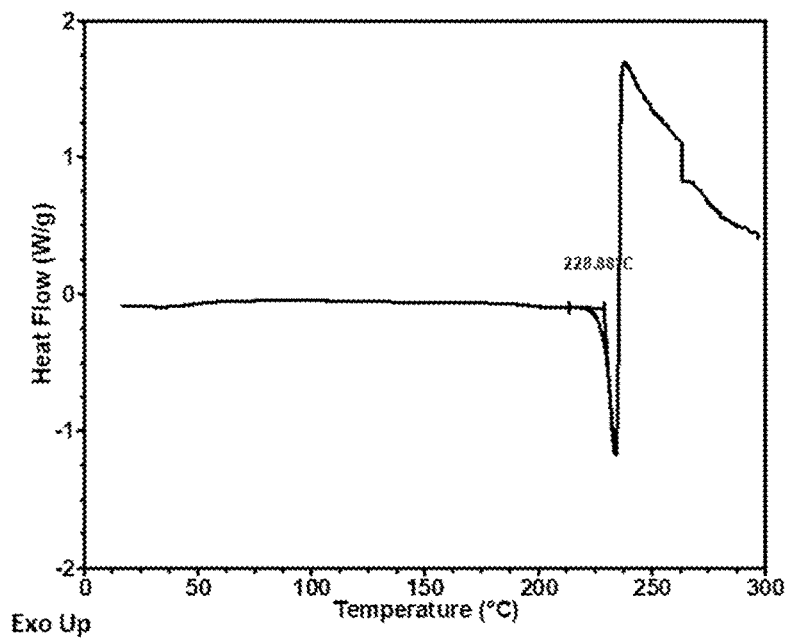
FIG. 56 shows the DSC thermogram of Compound 1 besylate Form II.
Figure 57:
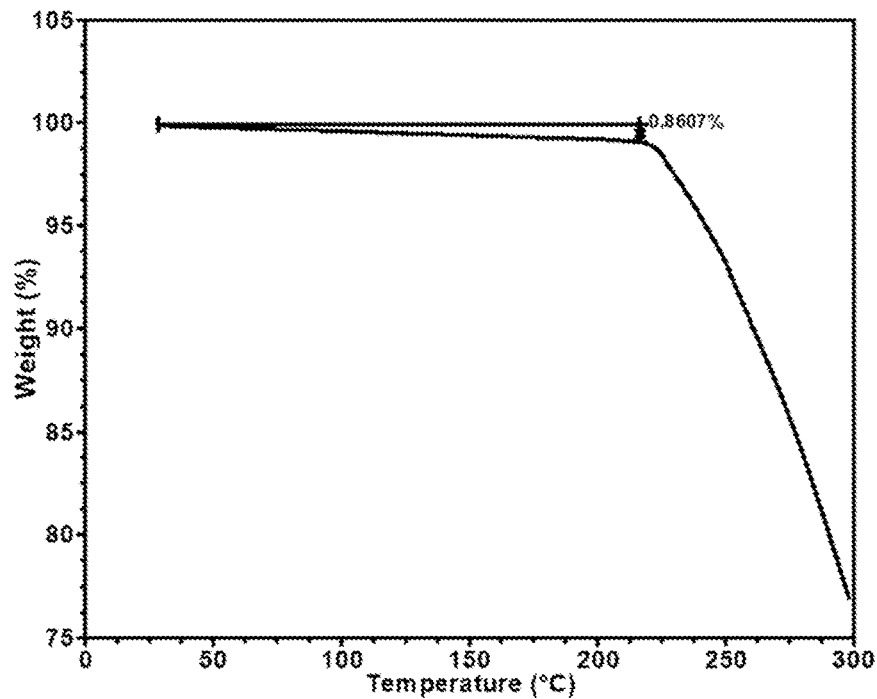
FIG. 57 shows the TGA thermogram of Compound 1 besylate Form II.

The DSC thermogram of Compound 1 besylate Form II is shown in FIG. 56. There is one endothermic event with an onset at approximately 229° C. FIG. 57 shows the TGA thermogram of Compound 1 besylate Form II.

Example 9. Compound 1 Esylate

Esylate Material A

Compound 1 esylate Material A was first prepared by stirring approximately 800 mg of Compound 1 freebase Form I and 1 equiv. of ethanesulfonic acid in about 5 mL of acetonitrile at about 22° C. for about 16 h. The resulting slurry was then filtered. The wet cake was then dried in the vacuum oven at about 50° C. XRPD of the dry solid was then collected.

Compound 1 esylate Material A was also prepared by drying solvates of Compound 1 esylate at 50° C. for 3 h or more. The XRPD pattern of Compound 1 esylate Material A is presented in FIG. 58. Table 21 summarizes the peaks in the XRPD pattern.

TABLE 21

XRPD peaks list of Compound 1 esylate Material A

| No. | Pos. [°2Th.] | Rel. Int. [%] |
|---|---|---|
| 1 | 5.7 | 100 |
| 2 | 8.9 | 6 |
| 3 | 9.4 | 6 |
| 4 | 10.3 | 9 |
| 5 | 11.5 | 5 |

TABLE 21-continued

XRPD peaks list of Compound 1 esylate Material A

| No. | Pos. [°2Th.] | Rel. Int. [%] |
|---|---|---|
| 6 | 13.0 | 3 |
| 7 | 13.8 | 9 |
| 8 | 14.8 | 3 |
| 9 | 16.0 | 3 |
| 10 | 16.6 | 2 |
| 11 | 17.7 | 4 |
| 12 | 18.4 | 5 |
| 13 | 19.7 | 5 |
| 14 | 20.7 | 4 |
| 15 | 21.2 | 4 |
| 16 | 23.2 | 6 |
| 17 | 24.9 | 8 |
| 18 | 26.7 | 3 |
| 19 | 27.6 | 5 |
| 20 | 28.5 | 5 |
| 21 | 31.1 | 8 |

Figure 59:
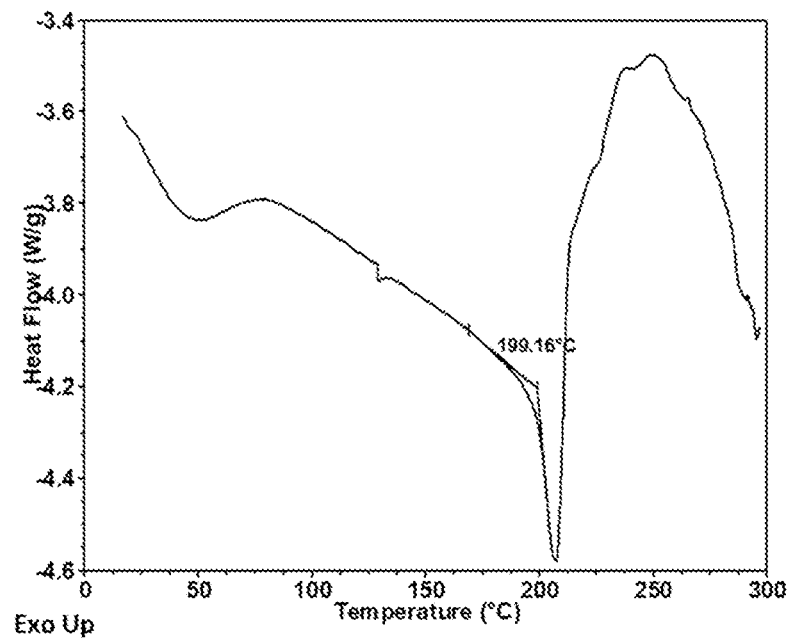
FIG. 59 shows the DSC thermogram of Compound 1 esylate Material A.
Figure 60:
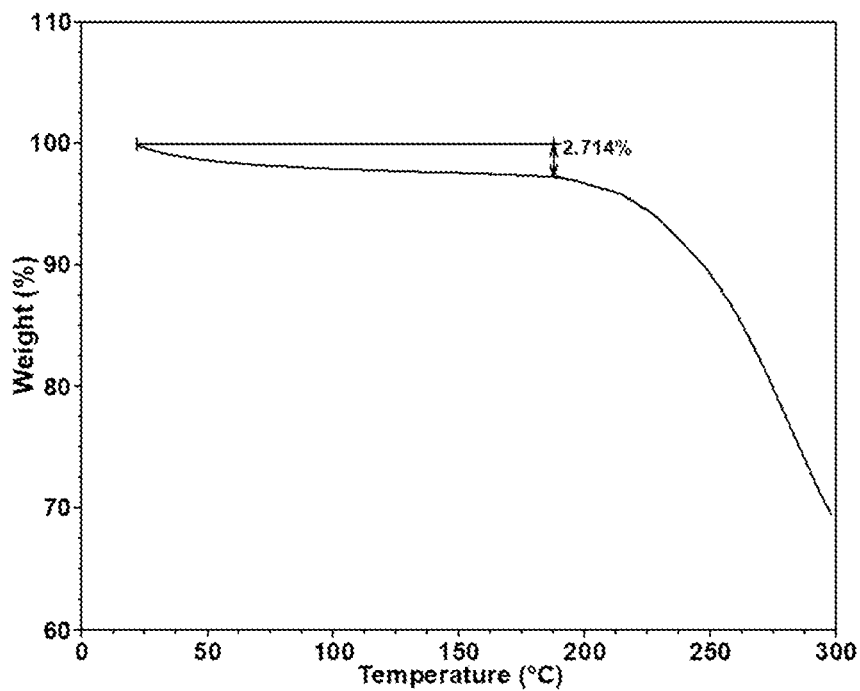
FIG. 60 shows the TGA thermogram of Compound 1 esylate Material A.

The DSC thermogram of Compound 1 esylate Material A is shown in FIG. 59. It shows a broad endotherm around 50° C. and another endothermic event with an onset around 199° C. The TGA thermogram of Compound 1 esylate Material A is shown in FIG. 60.

Esylate Material B

Compound 1 esylate Material B was prepared by stirring approximately 50 mg of esylate Material A in about 0.5 mL of isopropyl acetate for about 3 days at about 22° C. The slurry was then filtered and dried in the vacuum oven at about 50° C. for about 3 h. XRPD of the solid was then collected.

Material B was also be prepared by desolvating Compound 1 esylate salt solvates of organic solvents, including MTBE and heptane.

Figure 61:
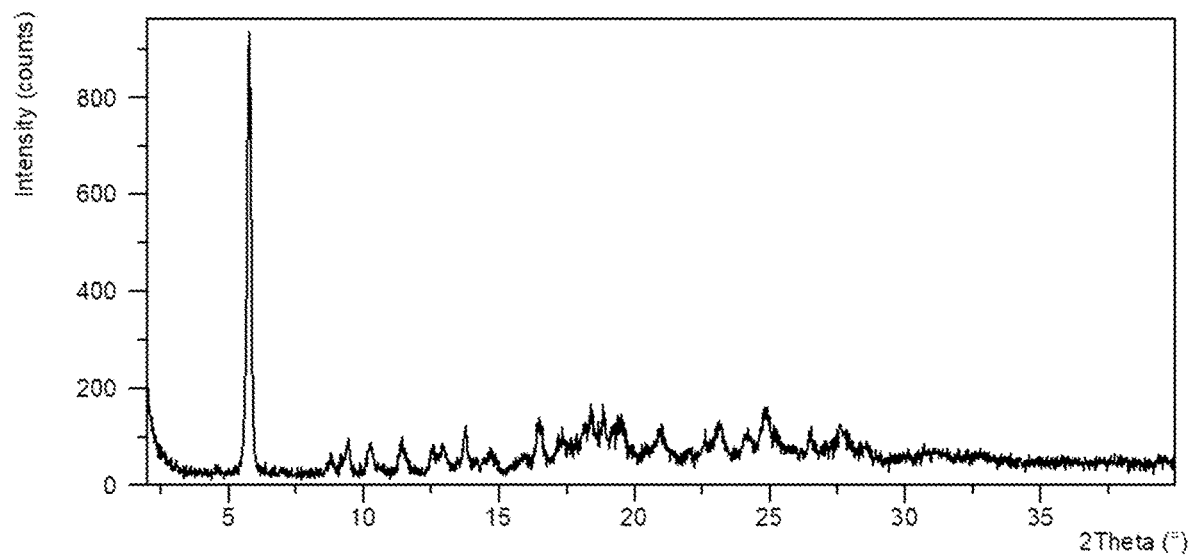
FIG. 61 shows the XRPD pattern of Compound 1 esylate Material B.

The XRPD pattern of Compound 1 esylate Material B is presented in FIG. 61. Table 22 summarizes the peaks in the XRPD pattern.

TABLE 22

XRPD peaks list of Compound 1 esylate Material B

| No. | Pos. [°2Th.] | Rel. Int. [%] |
|---|---|---|
| 1 | 5.8 | 100 |
| 2 | 8.8 | 3 |
| 3 | 9.5 | 8 |
| 4 | 10.3 | 6 |
| 5 | 11.4 | 7 |
| 6 | 12.6 | 5 |
| 7 | 13.0 | 6 |
| 8 | 13.8 | 11 |
| 9 | 14.7 | 4 |
| 10 | 16.4 | 10 |
| 11 | 17.3 | 7 |
| 12 | 18.4 | 13 |
| 13 | 18.9 | 13 |
| 14 | 19.5 | 10 |
| 15 | 21.0 | 8 |
| 16 | 22.6 | 6 |
| 17 | 23.2 | 9 |
| 18 | 24.1 | 7 |
| 19 | 24.9 | 12 |
| 20 | 26.5 | 7 |
| 21 | 27.6 | 8 |
| 22 | 31.1 | 1 |

Esylate Material C

Figure 62:
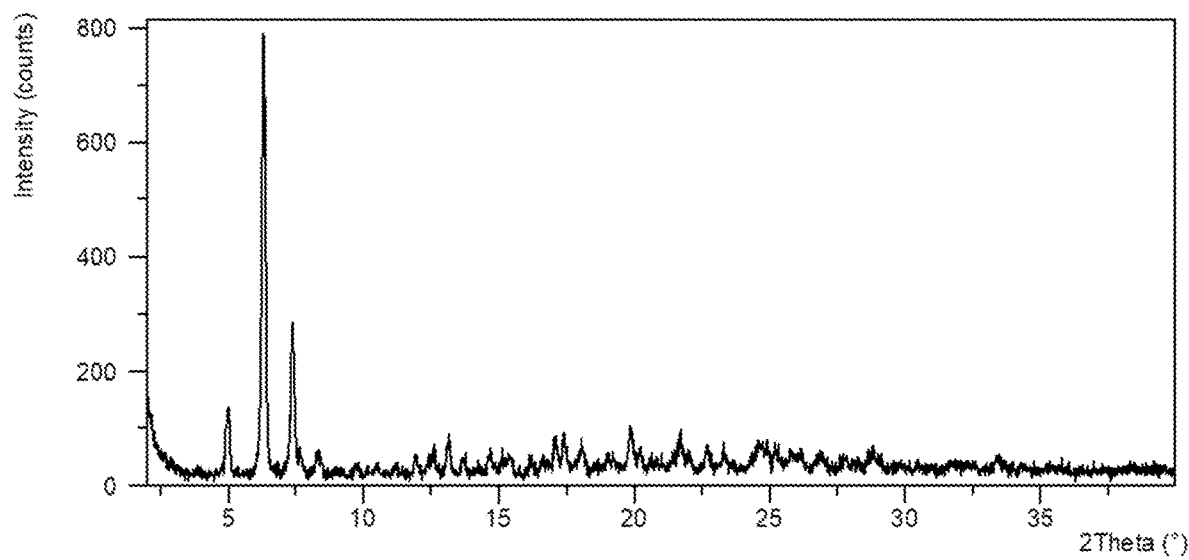
FIG. 62 shows the XRPD pattern of Compound 1 esylate Material C.

Compound 1 esylate salt Material C was first prepared by slurrying about 50 mg of Compound 1 esylate salt Material A in about 0.5 mL of isopropanol for approximately 3 days at about 22° C. The slurry was then filtered and the wet cake was dried at about 50° C. for 3 h. The XRPD pattern of Compound 1 esylate Material C is shown in FIG. 62. Table 23 summarizes the peaks in the XRPD pattern.

TABLE 23

XRPD peaks list of Compound 1 esylate Material C

| No. | Pos. [°2Th.] | Rel. Int. [%] |
|---|---|---|
| 1 | 5.0 | 15 |
| 2 | 6.3 | 100 |
| 3 | 7.3 | 33 |
| 4 | 8.4 | 4 |
| 5 | 9.8 | 2 |
| 6 | 11.9 | 4 |
| 7 | 12.6 | 5 |
| 8 | 13.1 | 7 |
| 9 | 13.7 | 4 |
| 10 | 14.7 | 5 |
| 11 | 15.1 | 3 |
| 12 | 15.4 | 3 |
| 13 | 16.2 | 3 |
| 14 | 17.1 | 8 |
| 15 | 17.4 | 8 |
| 16 | 18.1 | 5 |
| 17 | 19.1 | 3 |
| 18 | 19.9 | 10 |
| 19 | 20.2 | 4 |
| 20 | 21.7 | 7 |
| 21 | 22.0 | 3 |
| 22 | 22.7 | 5 |
| 23 | 23.3 | 4 |
| 24 | 24.6 | 6 |
| 25 | 25.2 | 4 |
| 26 | 26.0 | 3 |
| 27 | 26.9 | 3 |
| 28 | 27.6 | 3 |
| 29 | 28.9 | 3 |
| 30 | 33.4 | 2 |

Esylate Material D

Compound 1 esylate Material D was first prepared by mixing about 50 mg of Compound 1 esylate salt Material A in about 0.5 mL of methyl isobutyl ketone for approximately 3 days at about 22° C. The slurry was then centrifuged and the wet cake was dried at about 50° C. for 3 h. Material D can also be prepared in 2-methyltetrahydrofuran. The XRPD pattern of Compound 1 esylate Material D is presented in FIG. 63. Table 24 summarizes the peaks in the XRPD pattern.

TABLE 24

XRPD peaks list of Compound 1 esylate Material D

| No. | Pos. [°2Th.] | Rel. Int. [%] |
|---|---|---|
| 1 | 5.8 | 100 |
| 2 | 9.4 | 8 |
| 3 | 10.2 | 9 |
| 4 | 11.4 | 10 |
| 5 | 12.6 | 5 |
| 6 | 12.9 | 7 |
| 7 | 13.5 | 7 |
| 8 | 14.5 | 7 |
| 9 | 16.4 | 15 |
| 10 | 17.2 | 8 |
| 11 | 18.1 | 20 |
| 12 | 18.4 | 14 |
| 13 | 18.8 | 17 |
| 14 | 19.5 | 29 |
| 15 | 20.2 | 5 |
| 16 | 20.9 | 18 |
| 17 | 21.6 | 6 |
| 18 | 22.3 | 5 |
| 19 | 23.1 | 15 |
| 20 | 23.6 | 5 |
| 21 | 24.0 | 10 |
| 22 | 24.9 | 15 |
| 23 | 25.2 | 8 |
| 24 | 25.7 | 10 |
| 25 | 26.0 | 4 |
| 26 | 26.5 | 7 |
| 27 | 26.9 | 4 |
| 28 | 27.6 | 14 |
| 29 | 27.9 | 8 |
| 30 | 29.0 | 4 |
| 31 | 30.2 | 4 |
| 32 | 33.0 | 3 |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A solid form of Compound 1:

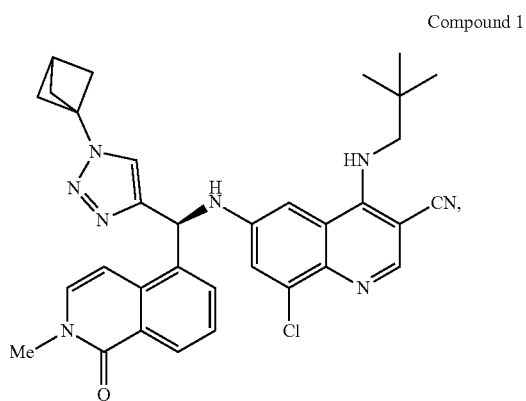 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

Compound 1 wherein the solid form is Freebase Form I characterized by an XRPD pattern comprising peaks at 10.4, 13.0, and 18.1 degrees 2θ (±0.2 degrees 2θ), wherein the XRPD is made using Cu Kα radiation.

2. The solid form of claim 1, characterized by an XRPD pattern further comprising one or more peaks at 18.8, 22.6, and 25.6 degrees 2θ (±0.2 degrees 2θ), wherein the XRPD is made using Cu Kα radiation.

3. The solid form of claim 1, characterized by an XRPD pattern further comprising one or more peaks at 19.2, 21.6, and 24.1 degrees 2θ (±0.2 degrees 2θ), wherein the XRPD is made using Cu Kα radiation.

4. The solid form of claim 1, characterized by an XRPD pattern comprising peaks at 10.4, 13.0, 18.1, 18.8, 19.2, 21.6, 22.6, 24.1, and 25.6 degrees 2θ (±0.2 degrees 2θ), wherein the XRPD is made using Cu Kα radiation.

5. The solid form of claim 1, characterized by an XRPD pattern as substantially shown in FIG. 2.

6. The solid form of claim 1, characterized by a DSC curve as substantially shown in FIG. 3.

7. The solid form of claim 1, characterized by a TGA thermogram as substantially shown in FIG. 4.

8. A solid form of an oxalate salt of Compound 1:

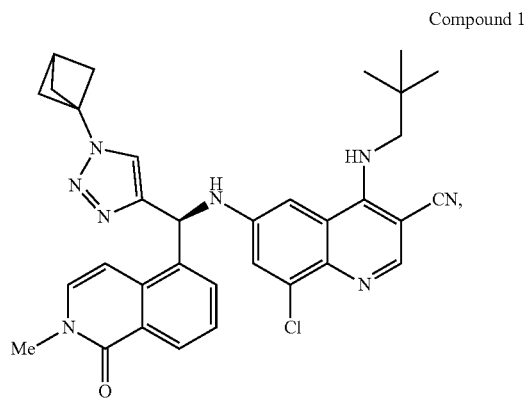 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

Compound 1 wherein the solid form is Oxalate Form I characterized by an XRPD pattern comprising peaks at 5.2, 6.3, and 7.5 degrees 2θ (±0.2 degrees 2θ), wherein the XRPD is made using Cu Kα radiation.

9. The solid form of claim 8, characterized by an XRPD pattern further comprising one or more peaks at 10.3, 13.3, and 22.6 degrees 2θ (±0.2 degrees 2θ), wherein the XRPD is made using Cu Kα radiation.

10. The solid form of claim 8, characterized by an XRPD pattern further comprising one or more peaks at 12.6, 16.4, and 17.9° 2 degrees 2θ (±0.2 degrees 2θ), wherein the XRPD is made using Cu Kα radiation.

11. The solid form of claim 8, characterized by an XRPD pattern comprising peaks at 5.2, 6.3, 7.5, 10.3, 12.6, 13.3, 16.4, 17.9, and 22.6 degrees 2θ (±0.2 degrees 2θ), wherein the XRPD is made using Cu Kα radiation.

12. The solid form of claim 8, characterized by an XRPD pattern as substantially shown in FIG. 26.

13. The solid form of claim 8, characterized by a DSC curve that comprises an endotherm with an onset at about 220° C.

14. The solid form of claim 8, characterized by a DSC curve as substantially shown in FIG. 27.

15. The solid form of claim 8, characterized by a TGA thermogram as substantially shown in FIG. 28.

16. A solid form of a maleate salt of Compound 1:

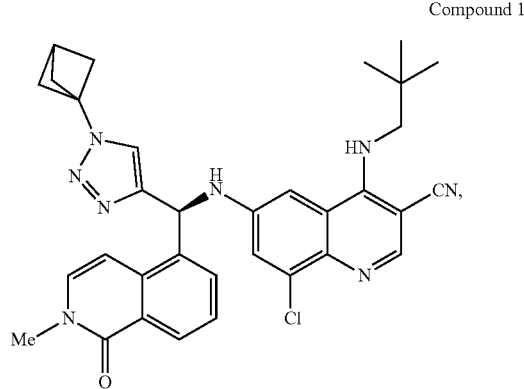

Compound 1 wherein the solid form is characterized by an XRPD pattern comprising peaks at 8.2, 8.6, and 11.9 degrees 2θ (±0.2 degrees 2θ), wherein the XRPD is made using Cu Kα radiation.

17. The solid form of claim 16, characterized by an XRPD pattern further comprising one or more peaks at 9.6, 17.3, and 19.1 degrees 2θ (±0.2 degrees 2θ), wherein the XRPD is made using Cu Kα radiation.

18. The solid form of claim 16, characterized by an XRPD pattern further comprising one or more peaks at 15.1, 21.1, and 23.5 degrees 2θ (±0.2 degrees 2θ), wherein the XRPD is made using Cu Kα radiation.

19. The solid form of claim 16, characterized by an XRPD pattern comprising peaks at 8.2, 8.6, 9.6, 11.9, 15.1, 17.3, 19.1 21.1, and 23.5 degrees 2θ (±0.2 degrees 2θ), wherein the XRPD is made using Cu Kα radiation.

20. The solid form of claim 16, characterized by an XRPD pattern as substantially shown in FIG. 35.

21. The solid form of claim 16, characterized by a DSC curve that comprises an endotherm with onset at about 130° C. and an exotherm with onset at about 160° C.

22. The solid form of claim 16, characterized by a DSC curve as substantially shown in FIG. 36.

23. The solid form of claim 16, characterized by a TGA thermogram as substantially shown in FIG. 37.

24. A solid form of a camsylate salt of Compound 1:

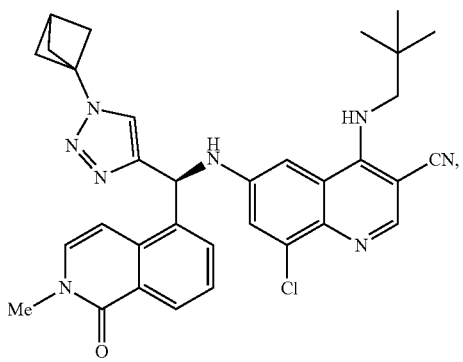

Compound 1 wherein the solid form is Camsylate Form I characterized by an XRPD pattern comprising peaks at 5.4, 12.0, and 17.5 degrees 2θ (±0.2 degrees 2θ), wherein the XRPD is made using Cu Kα radiation.

25. The solid form of claim 24, characterized by an XRPD pattern further comprising one or more peaks at 10.1, 19.5, 22.4 degrees 2θ (±0.2 degrees 2θ), wherein the XRPD is made using Cu Kα radiation.

26. The solid form of claim 24, characterized by an XRPD pattern further comprising one or more peaks at 6.7, 8.3, and 20.5 degrees 2θ (±0.2 degrees 2θ), wherein the XRPD is made using Cu Kα radiation.

27. The solid form of claim 24, characterized by an XRPD pattern comprising peaks at 5.4, 6.7, 8.3, 10.1, 12.0, 17.5, 19.5, 20.5, and 22.4 degrees 2θ (±0.2 degrees 2θ), wherein the XRPD is made using Cu Kα radiation.

28. The solid form of claim 24, characterized by an XRPD pattern as substantially shown in FIG. 38.

29. The solid form of claim 24, characterized by a DSC curve that comprises a broad endotherm between ambient temperature to about 120° C. followed by a melting onset at about 196° C.

30. The solid form of claim 24, characterized by a DSC curve as substantially shown in FIG. 39.

31. The solid form of claim 24, characterized by a TGA thermogram as substantially shown in FIG. 40.

32. A solid form of a camyslate salt of Compound 1:

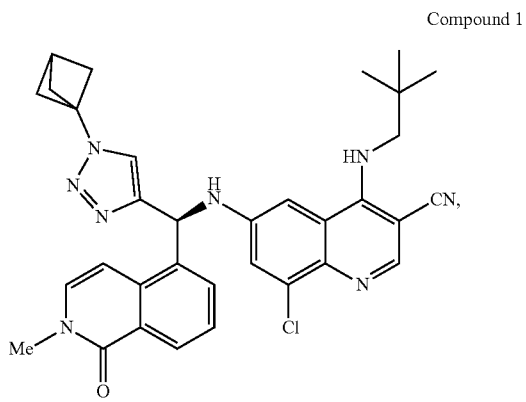 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

Compound 1 wherein the solid form is Camsylate Form II characterized by an XRPD pattern comprising peaks at 2.8, 4.7, and 5.4 degrees 2θ (±0.2 degrees 2θ), wherein the XRPD is made using Cu Kα radiation.

33. The solid form of claim 32, characterized by an XRPD pattern further comprising one or more additional peaks at 7.2, 8.1, and 10.8 degrees 2θ (±0.2 degrees 2θ), wherein the XRPD is made using Cu Kα radiation.

34. The solid form of claim 32, characterized by an XRPD pattern further comprising one or more peaks at 9.8, 12.4, and 17.7 degrees 2θ (±0.2 degrees 2θ), wherein the XRPD is made using Cu Kα radiation.

35. The solid form of claim 32, characterized by an XRPD pattern comprising peaks at 2.8, 4.7, 5.4, 7.2, 8.1, 9.8, 10.8, 12.4, and 17.7 degrees 2θ (±0.2 degrees 2θ), wherein the XRPD is made using Cu Kα radiation.

36. The solid form of claim 32, characterized by an XRPD pattern as substantially shown in FIG. 41.

37. The solid form of claim 32, characterized by a DSC curve that comprises a broad endotherm between ambient temperature to about 120° C. followed by several endotherms at about 130° C., 198° C., and 214° C., respectively.

38. The solid form of claim 32, characterized by a DSC curve as substantially shown in FIG. 42.

39. The solid form of claim 32, characterized by a TGA thermogram as substantially shown in FIG. 43.

40. A solid form of a camsylate salt of Compound 1:

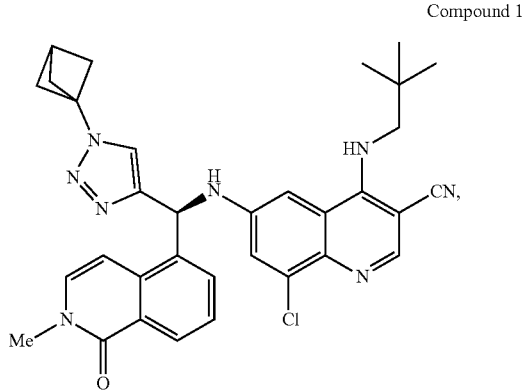 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

Compound 1 wherein the solid form is Camsylate Form III characterized by an XRPD pattern comprising peaks at 5.5, 8.9, and 18.5 degrees 2θ (±0.2 degrees 2θ), wherein the XRPD is made using Cu Kα radiation.

41. The solid form of claim 40, characterized by an XRPD pattern further comprising one or more peaks at 4.5, 10.9, and 16.6 degrees 2θ (±0.2 degrees 2θ), wherein the XRPD is made using Cu Kα radiation.

42. The solid form of claim 40, characterized by an XRPD pattern further comprising one or more peaks at 12.2, 21.5, and 21.8 degrees 2θ (±0.2 degrees 2θ), wherein the XRPD is made using Cu Kα radiation.

43. The solid form of claim 40, characterized by an XRPD pattern comprising peaks at 4.5, 5.5, 8.9, 10.9, 12.2, 16.6, 18.5, 21.5, and 21.8 degrees 2θ (±0.2 degrees 2θ), wherein the XRPD is made using Cu Kα radiation.

44. The solid form of claim 40, characterized by an XRPD pattern as substantially shown in FIG. 44.

45. The solid form of claim 40, characterized by a DSC curve that comprises a broad endotherm between ambient temperature to about 100° C. followed by a melting endotherm with an onset at about 207° C.

46. The solid form of claim 40, characterized by a DSC curve as substantially shown in FIG. 45.

47. The solid form of claim 40, characterized by a TGA thermogram as substantially shown in FIG. 46.

* * * * *